United States Patent [19]

Oka et al.

[11] Patent Number: 4,751,295

[45] Date of Patent: Jun. 14, 1988

[54] CEPHALOSPORIN DERIVATIVES

[75] Inventors: Masahisa Oka, Yokohama; Haruhiro Yamashita, Ichikawa; Jun Okumura, Yokohama; Takayuki Naito, Kawasaki, all of Japan

[73] Assignee: Bristol-Myers Company, New York, N.Y.

[21] Appl. No.: 920,933

[22] Filed: Oct. 17, 1986

Related U.S. Application Data

[63] Continuation of Ser. No. 597,941, Apr. 9, 1984, abandoned.

[51] Int. Cl.$^4$ .................. C07D 501/46; A61K 31/545
[52] U.S. Cl. ..................................... 540/222; 540/225
[58] Field of Search ................ 540/222, 225; 514/202, 514/203

[56] References Cited

U.S. PATENT DOCUMENTS 4,381,299 4/1983 Terajii et al. .......................... 544/27
4,486,586 12/1984 Narita et al. .......................... 544/022

Primary Examiner—Nicholas S. Rizzo

Attorney, Agent, or Firm—Aldo A. Algieri

[57] ABSTRACT

7-[2-(5-Amino-1,2,4-thiadiazol-3-yl)-2-(substituted)-iminoacetamido]-3-[3-(quaternaryammonio)-1-propen-1-yl]-3-cephem-4-carboxylates of the formula

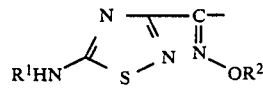

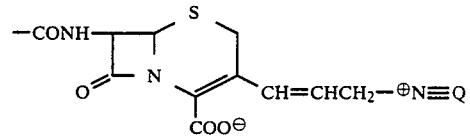

in which $R^1$ and $R^2$ are defined herein and $-{}^{\oplus}N{\equiv}Q$ is a quaternary ammonio group as defined herein, and salts, solvates, hydrates and esters thereof, are potent antibacterial agents. Processes for their preparation and intermediates in such processes are described.

7 Claims, No Drawings

CEPHALOSPORIN DERIVATIVES

This application is a continuation of application Ser. No. 597,941 filed Apr. 9, 1984, now abandoned.

SUMMARY OF THE INVENTION

This application relates to 7-[2-(5-amino-1,2,4-thiadiazol-3-yl)-2-(substituted)iminoacetamido]-3-[3-(quaternaryammonio)-1-propen-1-yl]-3-cephem-4-carboxylates of the formula

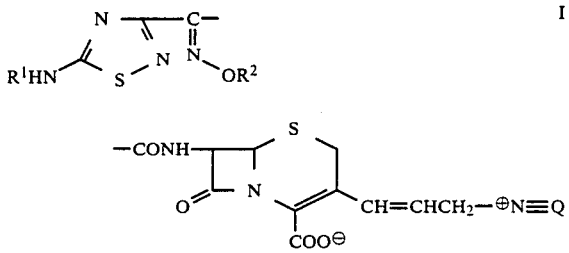

in which $R^1$ and $R^2$ are as defined herein and $—^{\oplus}N≡Q$ is a quaternary ammonio group as defined herein, and to salts and esters thereof. This invention also relates to processes for the preparation of the compounds of Formula I, to pharmaceutical compositions containing at least one compound of Formula I, and to intermediates in their preparation.

BACKGROUND AND PRIOR ART (A) U.S. Pat. No. 4,390,534, issued June 28, 1983 to Tsutomu Teraji et al., discloses cephem and cepham compounds of the formula

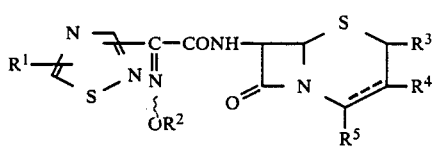

wherein $R^1$ is amino or protected amino; $R^2$ is hydrogen, acyl, optionally substituted aryl, substituted alkyl, alkenyl, alkynyl, optionally substituted cycloalkyl, cycloalkenyl or an O- or S-containing 5-membered heterocyclic ring substituted with oxo group(s); $R^3$ is hydrogen or alkyl; $R^4$ is hydrogen, acyloxyalkyl, acylthioalkyl, optionally substituted pyridinioalkyl, optionally substituted heterocyclylthioalkyl, alkyl, halogen, hydroxy or optionally substituted thiazolioalkyl; and $R^5$ is carboxy or protected carboxy; provided that $R^5$ is $COO^-$ when $R^4$ is optionally substituted pyridinioalkyl or optionally substituted thiazolioalkyl; and the dashed line indicates either a single or double bond.

European Patent Application No. 13,762, published Aug. 6, 1980 is concordant thereto and has a similar disclosure.

U.S. Pat. Nos. 4,381,299 (issued Apr. 26, 1983), 4,331,665 (issued May 25, 1982) and 4,332,798 (issued June 1, 1982) each issued on parent applications of U.S. Pat. No. 4,390,534, and have similar disclosures.

(B) European Patent Application No. 62,321, published Oct. 13, 1982, discloses cephem compounds of the formula

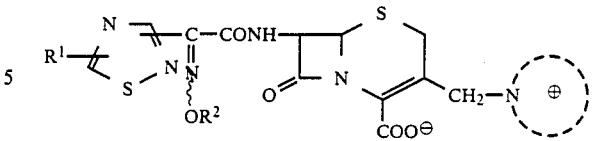

wherein $R^1$ is amino or protected amino; $R^2$ is an optionally substituted lower aliphatic hydrocarbon group, or cycloalkenyl; and the group of the formula

is an optionally substituted heterocyclic cation group containing more than one nitrogen atom; and pharmaceutically acceptable salts thereof. Also disclosed are intermediates of the formula

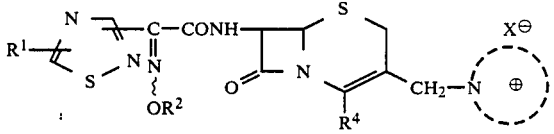

wherein $R^1$ and $R^2$ are as defined above, $R^4$ is a protected carboxyl group and $X^-$ is an acid residue.

(C) European Patent Application No. 74,653, published Mar. 23, 1983, discloses cephem compounds of the formula

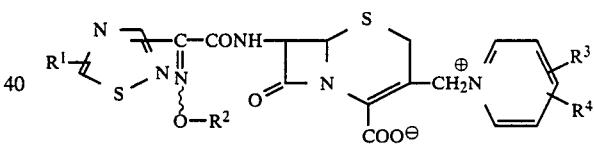

wherein $R^1$ is amino or protected amino;

$R^2$ is an optionally substituted lower aliphatic hydrocarbon group, cyclo(lower)alkyl or cyclo(lower)alkenyl;

$R^3$ is (lower)alkylamino, N-protected(lower)alkylamino, di(lower)alkylamino, sulfo(lower)alkylamino, hydroxy(lower)alkylamino, N-protected hydroxy(lower)alkylamino, acyloxy(lower)alkyl, (lower)alkoxy(lower)alkoxy(lower)alkyl, di(lower)alkylamino(lower)alkyl, (lower)alkylthio(lower)alkyl, (lower)alkylthio, (lower)alkoxy, (lower)alkoxy(lower)alkoxy, hydroxy(lower)alkoxy, acyl(lower)alkyl, hydroxy(lower)alkylthio, di(lower)alkylamino(lower)alkylthio, N-containing unsaturated 5-membered heterocyclic group, N-containing unsaturated 5-membered heterocyclicthio, or N-containing unsaturated 5 or 6-membered heterocyclicthio(lower)alkyl which may be substituted with suitable substituent(s); and $R^4$ is hydrogen or (lower)alkyl; or a salt thereof.

(D) U.S. Pat. No. 4,332,800, issued June 1, 1982 to Tsutomu Teraji et al., discloses inter alia compounds of the formula

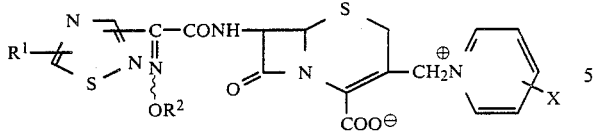

wherein R[1] is amino or protected amino; R[2] is (lower-)alkyl and X is hydrogen or carbamoyl.

(E) European Patent Application No. 47,977, published Mar. 24, 1982, discloses cephem compounds of the formula

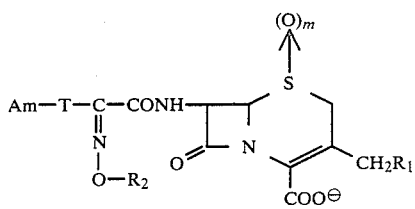

wherein m is 0 or 1; Am is optionally substituted amino; T is a thiadiazolyl moiety (attached to the other groups by two of its carbon atoms); $R_2$ is hydrogen, optionally substituted alkyl, cycloalkyl or optionally substituted carbamoyl; and $R_1$ is optionally substituted thiazolio, optionally substituted pyrazolio, tri(lower)alkylammonio or a pyridinio group of the formula

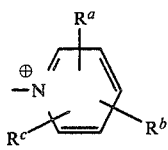

in which $R^a$ is substituted (lower)alkyl [the substituent being cycloalkyl, phenyl, hydroxy, alkoxy, halogen, cyano, carbamoyl, carboxyl or sulfo], (lower)alkenyl or carboxy-substituted (lower)alkenyl, (lower)alkylthio or carboxy-substituted (lower)alkylthio, amino or monosubstituted amino [the substituent being(lower)alkyl, (lower)alkanoyl or aminobenzenesulfonyl], di(lower)alkylamino, substituted carbamoyl [the substituent being (lower)alkyl, hydroxy(lower)alkyl, (lower)alkoxy, hydroxy or cyano], di(lower)alkylcarbamoyl, thiocarbamoyl, cycloalkyl, phenyl, hydroxy, (lower)alkoxy, halogen, (lower)alkoxycarbonyl, (lower)alkanoyloxy, (lower)alkanoyl, carboxyl, sulfo, cyano, nitro or hydroxysulfo(lower)alkyl; $R^b$ is hydrogen or carbamoyl, or has the same meaning as $R^a$; and $R^c$ is hydrogen or has the same meaning as $R^a$; and salts thereof.

Although not formally related, European Patent Application No. 25,017, published Mar. 11, 1981, has a similar disclosure.

(F) European Patent Application No. 30,630, published June 24, 1981, discloses 3-vinyl cephem compounds of the formula

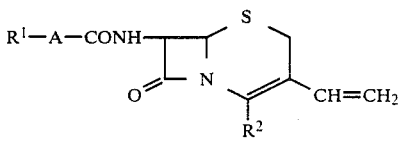

wherein R[1] is an optionally protected amino-substituted heterocyclic group which may also have halogen, or a group of the formula

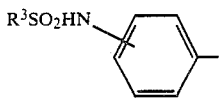

in which R[3] is (lower)alkyl; R[2] is carboxy or protected carboxy; and A is lower alkylene which may have a substituent selected from amino, protected amino, hydroxy, oxo and a group of the formula $=N\sim OR^4$, wherein R[4] is hydrogen, cyclo(lower)alkenyl, (lower-)alkynyl, (lower)alkenyl [optionally substituted by carboxy or protected carboxy], (lower)alkyl [optionally substituted by one or more of carboxy, protected carboxy, amino, protected amino, cyano, phosphono, protected phosphino and a heterocyclic group which itself may be substituted]; and salts thereof.

This application specifically discloses compounds of the formula

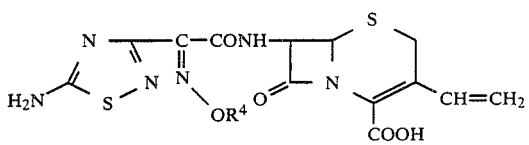

in which $OR^4$ is methoxy, carboxymethoxy, tert-butoxycarbonylmethoxy or 1-tert-butoxycarbonylethoxy.

(G) U.K. Patent Specification No. 1,399,086 published June 25, 1975, contains a generic disclosure encompassing a vast number of cephalosporins of the formula

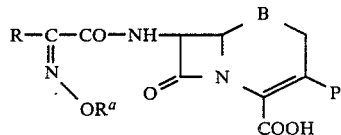

wherein R is hydrogen or an organic group, $R^a$ is an etherifying monovalent organic group linked to the oxygen through a carbon atom, B is >S or >S→O, and P is an organic group. In one embodiment, P may be inter alia a vinyl group of the formula

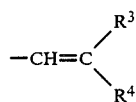

in which R[3] and R[4] independently may be hydrogen, nitrile, (lower)alkoxycarbonyl, or substituted or unsubstituted aliphatic, cycloaliphatic, araliphatic or aromatic. However, the 5-amino-1,2,4-thiadiazol-3-yl group is not identified as a possible R substituent and there is no disclosure or suggestion that P may be a quaternary ammonio-substituted propenyl group. U.S. Pat. No. 3,971,778 and its divisionals Nos. 4,024,133, 4,024,137, 4,064,346, 4,033,950, 4,079,178, 4,091,209, 4,092,477 and 4,093,803 have similar disclosures.

(H) European Patent Application No. 88,385, published Sept. 14, 1983, discloses compounds of the formula

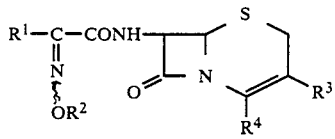

in which R¹ is (unsubstituted) thiadiazolyl; R² is carboxy(lower)alkyl or protected carboxy(lower)alkyl; R³ is hydrogen, halogen or (lower)alkenyl; and R⁴ is carboxy or protected carboxy. Although 1-propenyl is listed as one of the possible meanings of R³, the application only exemplifies compounds where R³ is hydrogen, chloro or vinyl.

(I) U.S. Pat. No. 4,307,233 issued to Daniel Farge et al. on Dec. 22, 1981, discloses inter alia, 3-vinylcephalosporin derivatives of the formula

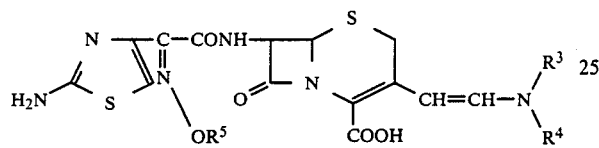

in which R⁵ inter alia may be alkyl, vinyl, cyanomethyl or a protective group such as 2-methoxyprop-2-yl, and R³ and R⁴ are alkyl groups (optionally substituted by hydroxy, alkoxy, amino, alkylamino or dialkylamino) or phenyl groups, or R³ and R⁴, taken together with the nitrogen to which they are attached, may form a saturated heterocyclic ring of 5 or 6 members, optionally containing another hetero-atom selected from N, O and S, and optionally substituted by an alkyl group. The compounds are useful as intermediates in the preparation of 3-thiovinyl cephalosporin derivatives. There is no disclosure or suggestion of a 5-amino-1,2,4-thiadiazol-3-yl moiety in place of the 2-aminothiazol-4-yl substituent or of a quaternary ammonio-substituted propenyl moiety for the 3-substituent. Published U.K. Patent Application No. 2,051,062 is concordant thereto and has a similar disclosure.

(J) European Patent Application No. 53,537, published June 9, 1982, discloses, inter alia, 3-vinylcephalosporin derivatives of the formula

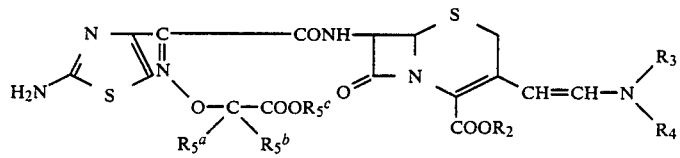

in which R₅ᵃ and R₅ᵇ are the same or different and are hydrogen or alkyl, or taken together, form an alkylene group containing 2 or 3 carbon atoms, R₅ᶜ is an acid protecting group, R₂ is an acid protecting group such as an ester, R₃ and R₄ are the same or different and are hydrogen, alkyl (optionally substituted by hydroxy, alkoxy, amino, alkylamino or dialkylamino) or phenyl groups, or R₃ and R₄, taken together with the nitrogen to which they are attached, may form a saturated heterocyclic ring of 5 or 6 members, optionally containing another hetero-atom selected from N, O and S, and optionally substituted by an alkyl group. The compounds are useful as intermediates in the preparation of 3-thiovinyl cephalosporin derivatives. There is no disclosure or suggestion of a 5-amino-1,2,4-thiadiazol-3-yl moiety in place of the 2-aminothiazol-4-yl substituent or of a quaternary ammonio-substituted propenyl group for the 3-substituent.

U.S. Pat. No. 4,423,214 is concordant thereto and has a similar disclosure.

(K) European Patent Application No. 53,074, published June 2, 1982, generically discloses a vast number of 3-vinylcephalosporin derivatives of the formula

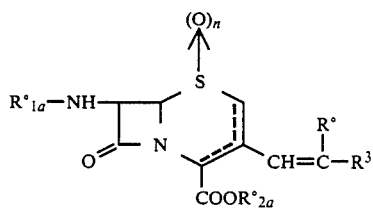

wherein R₁ₐ° (in one of several embodiments) may be

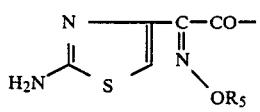

in which R₅ inter alia may be hydrogen, alkyl, vinyl, cyanomethyl, an oxime-protecting group such as trityl, etc., or a group of the formula

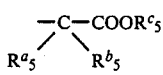

in which R₅ᵃ and R₅ᵇ are the same or different, and may be hydrogen, alkyl or, taken together, an alkylene radical of 2 or 3 carbon atoms, and R₅ᶜ is hydrogen or an acid-protecting radical;

R₂ₐ° is hydrogen or an acid-protecting radical such as methoxymethyl;

R° (in one of several embodiments) may be a methyl group substituted by a 5- or 6-membered aromatic heterocyclic ring containing a single hetero atom, such as 2- or 3-pyridyl, 2- or b 3-thienyl or 2- or 3-furyl; and R₃ is a group of the formula

R₄SO₂O— in which R₄ may be alkyl, trihalomethyl or optionally substituted phenyl.

These compounds are stated to be intermediates in the preparation of compounds in which the 3-substituent is a group of the formula

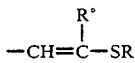

which are stated to have antibacterial activity.

Although this patent includes the possibility of R° being a methyl group substituted by an N-containing heterocyclic ring, in both the intermediates and final products (thus giving a heterocyclic-substituted propenyl moiety), it teaches only that the heterocyclic ring is attached via one of its carbon atoms. Thus, there is no suggestion of a quaternary ammonio-substituted propenyl group. The reference exemplifies R° in the intermediates and final products only as methyl. Further, in both the intermediates and final product, the propenyl group must contain a second substituent ($-O_3SR^4$ or $-SR$, respectively). Also there is no disclosure or suggestion of a 5-amino-1,2,4-thiadiazol-3-yl moiety in place of the 2-aminothiazol-4-yl substituent.

(L) European Patent Application No. 53,538, published June 9, 1982, discloses, inter alia, 3-vinylcephalosporin intermediates of the formula

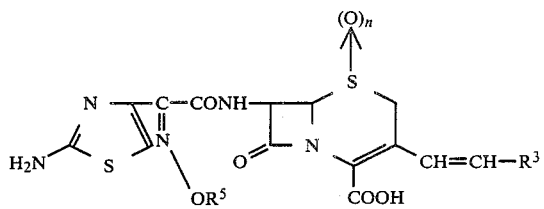

in which n is 0 or 1, $R^5$ is hydrogen, alkyl, vinyl, cyanomethyl or an oxime-protecting group, and $R^3$ is halogen. There is no disclosure or suggestion of a 5-amino-1,2,4-thiadiazol-3-yl moiety in place of the 2-aminothiazol-4-yl substituent, and no disclosure or suggestion of a 3-halo-1-propen-1-yl substituent in the 3-position.

COMPLETE DISCLOSURE

This application relates to novel cephalosporin derivatives which are potent antibacterial agents. More particularly, it relates to compounds of the formula

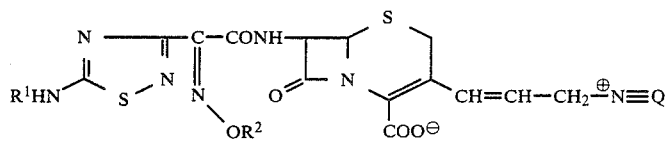

wherein $R^1$ is hydrogen or a conventional amino-protecting group, $R^2$ is hydrogen, a straight or branched chain alkyl group containing from 1 to 4 carbon atoms, a cycloalkyl or cycloalkenyl ring containing from 3 to 6 carbon atoms, or a group of the formula

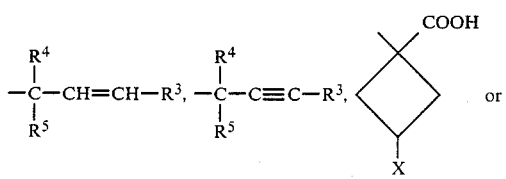

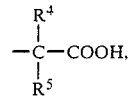

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and

is a quaternary ammonio group, and nontoxic pharmaceutically acceptable salts and physiologically hydrolyzable esters thereof. Also included within the scope of the invention are the solvates (including hydrates) of the compounds of Formula I, as well as the tautomeric forms of the compounds of Formula I, e.g. the 2-iminothiazolin-4-yl form of the 2-aminothiazol-4-yl moiety.

In another aspect, this application relates to a process for the preparation of the compounds of Formula I and to certain intermediates in their preparation.

As shown in the structural formula, the compounds of Formula I have the "syn" or "Z" configuration with respect to the alkoxyimino group. Because the compounds are geometric isomers, some of the "anti" isomer may also be present. This invention comprises compounds of Formula I containing at least 90% of the "syn" isomer. Preferably the compounds of Formula I are "syn" isomers which are essentially free of the corresponding "anti" isomers.

In addition to geometric isomers possible with respect to the alkoxyimino group, the compounds of Formula I (and the intermediates of Formulae VIII and IX) also form geometric (cis and trans) isomers about the double bond of the propenyl group. Both the cis ("Z") and trans ("E") isomers of these compounds are specifically included within the scope of this invention.

The nontoxic pharmaceutically acceptable salts of the compounds of Formula I include salts with mineral acids such as hydrochloric, hydrobromic, phosphoric and sulfuric, or with organic carboxylic acids or sulfonic acids such as acetic, trifluoroacetic, citric, formic, maleic, oxalic, succinic, benzoic, tartaric, fumaric, mandelic, ascorbic, malic, methanesulfonic, benzenesulfonic, p-toluenesulfonic and other acids known and used in the penicillin and cephalosporin arts. Preparation of these acid addition salts is carried out by conventional techniques.

Examples of physiologically hydrolyzable esters of the compounds of Formula I include indanyl, phthalidyl, methoxymethyl, acetoxymethyl, pivaloyloxymethyl, glycyloxymethyl, phenylglycyloxymethyl, 5-methyl-2-oxo-1,3-dioxolen-4-ylmethyl and other physiologically hydrolyzable esters known and used in the penicillin and cephalosporin arts. Such esters are prepared by conventional techniques known in the art.

The compounds of Formula I in which $R^1$ is hydrogen exhibit high antibacterial activity against various Gram-positive and Gram-negative bacteria, and are useful in the treatment of bacterial infections in animals, including man. The compounds of Formula I may be formulated for parenteral use in a conventional manner utilizing known pharmaceutical carriers and excipients, and may be presented in unit dosage form or in multi-dosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. The compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of Formula I. The dosage of the compounds of Formula I is dependent on such factors as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

The quaternary ammonio group of the formula

may be acyclic, cyclic, or a combination of the two, and may contain one or more additional hetero atoms selected from nitrogen, sulfur and oxygen.

An example of an acyclic quaternary ammonio group is a group of the formula:

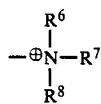

in which $R^6$, $R^7$ and $R^8$ may be the same or different and may, for example, be (lower)alkyl or substituted (lower)alkyl in which the substituents are, for example, halogen, amino with the provision that the amino group may not be on an α-carbon, hydroxy with the provision that the hydroxy group may not be on an α-carbon, (lower)alkoxy with the provision that the alkoxy group may not be on an α-carbon, (lower)alkylthio, (lower)alkylamino, di(lower)alkylamino, carbamoyl, (lower)alkenyl, phenyl(lower)alkyl, phenyl or substituted phenyl (in which the substituents may be, for example, halogen, hydroxy, amino, (lower)alkylamino, di(lower)alkylamino, acylamino, (lower)alkyl, (lower)alkylthio, (lower)alkoxy or the like).

Examples of cyclic quaternary ammonio groups are fully unsaturated monocyclic heterocyclic ring systems, and bicyclic heterocyclic ring systems in which at least one N-containing ring is fully unsaturated. Suitable cyclic quaternary ammonio ring systems include, for example, those of the formulae

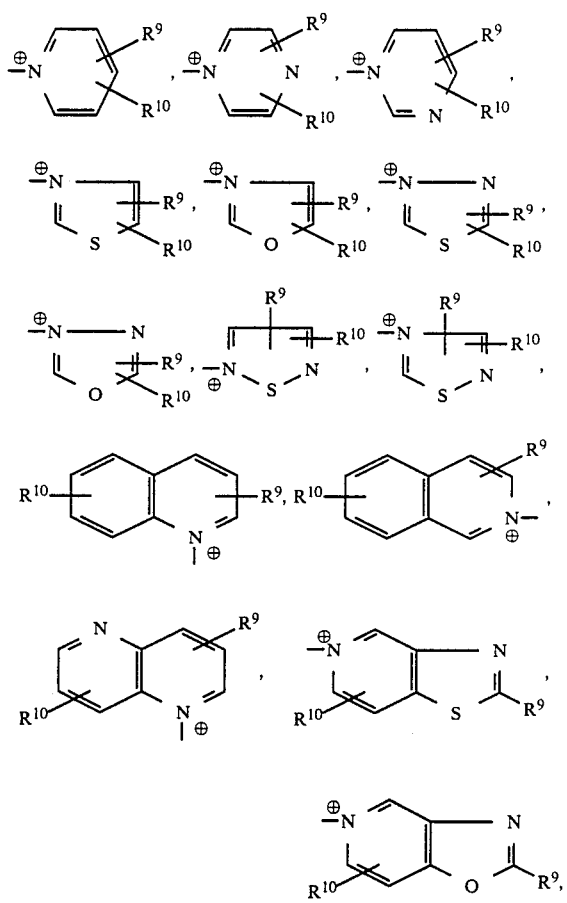

and the like, in which $R^9$ and $R^{10}$ are the same or different and may be, for example, hydrogen, halogen, amino, (lower)alkyl, (lower)alkenyl, (lower)alkylthio, carboxy, hydroxy, (lower)alkoxy, (lower)alkoxy(lower)alkyl, halo(lower)alkyl, hydroxy(lower)alkyl, amino(lower)alkyl, (lower)alkylamino(lower)alkyl, di(lower)alkylamino(lower)alkyl, (lower)alkylamino, di(lower)alkylamino, carboxy(lower)alkyl, carboxy(lower)alkylamino, carboxy(lower)alkylthio, carbamoyl, N-(lower)alkylcarbamoyl, formylamino, acylamino, acyloxy, phenyl, pyridyl, amidino, guanidino and the like. Where the structure of the heterocyclic ring permits, $R^9$ and $R^{10}$, taken together, may be an alkylene group containing from 3 to 5 carbon atoms, e.g. propylene.

Examples of combined acyclic/acyclic quaternary ammonio groups include, for example, those of the formulae

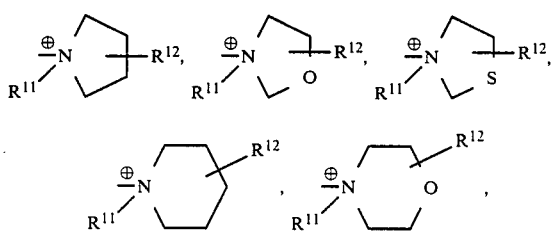

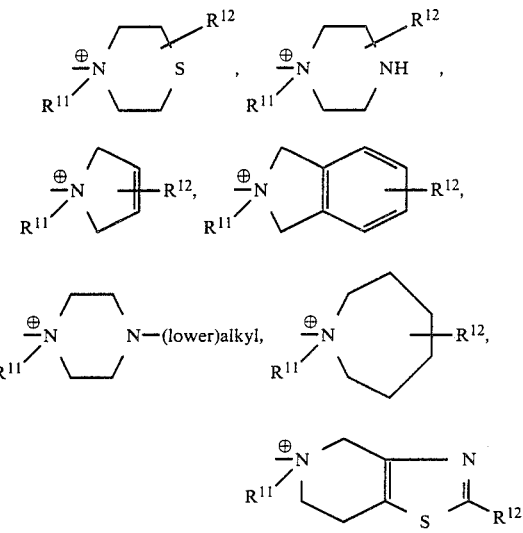

and the like, in which $R^{11}$ may be, for example, (lower)alkyl, (lower)alkoxy(lower)alkyl, hydroxy(lower)alkyl with the provision that the hydroxy may not be on an α-carbon, carboxy(lower)alkyl, amino(lower)alkyl with the provision that the amino may not be on an α-carbon, (lower)alkenyl, halo(lower)alkyl, allyl and the like, and $R^{12}$ may be, for example, hydrogen, hydroxy, halogen, (lower)alkyl, hydroxy(lower)alkyl, (lower)alkoxy(lower)alkyl, halo(lower)alkyl, amino(lower)alkyl, (lower)alkoxy, (lower)alkylthio, (lower)alkenyl, amino, (lower)alkylamino, di(lower)alkylamino, acylamino, acyloxy, carbamoyl, amidino(lower)alkyl, phenyl, pyridyl, amidino, guanidino and the like.

Preferred quaternary-ammonio groups are those of the formulae

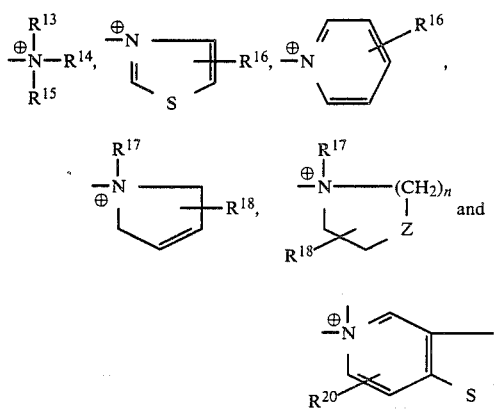

wherein $R^{13}$, $R^{14}$ and $R^{15}$ are the same or different and are (lower)alkyl, (lower)alkenyl, amino(lower)alkyl with the provision that the amino may not be on an α-carbon, or hydroxy(lower)alkyl with the provision that the hydroxy group may not be on an α-carbon;

$R^{16}$ is hydrogen, (lower)alkyl, (lower)alkoxy, (lower)alkylthio, amino, (lower)alkylamino, di(lower)alkylamino, formylamino, (lower)alkanoylamino, carboxy, hydroxy, carboxy(lower)alkyl, carboxy(lower)alkylthio, hydroxy(lower)alkyl, halo(lower)alkyl, amino(lower)alkyl, (lower)alkoxy(lower)alkyl, carbamoyl or N-(lower)alkylcarbamoyl, or $R^{16}$ may represent a divalent alkylene group having 3 to 5 carbon atoms;

$R^{17}$ is (lower)alkyl, (lower)alkoxy(lower)alkyl, halo(lower)alkyl, allyl, hydroxy(lower)alkyl with the provision that the hydroxy group is not on the α-carbon, amino(lower)alkyl with the provision that the amino group is not on the α-carbon, or phenyl(lower)alkyl;

$R^{18}$ is hydrogen, (lower)alkyl, (lower)alkoxy, (lower)alkoxy(lower)alkyl, (lower)alkylthio, amino, (lower)alkylamino, di(lower)alkylamino, carboxy, hydroxy, carboxy(lower)alkyl, hydroxy(lower)alkyl, amino(lower)alkyl, formylamino, (lower)alkanoylamino, carbamoyl or N-(lower)alkylcarbamoyl;

n is an integer of from 1 to 3, inclusive;

Z is $CH_2$ or, when n is 2, Z also may be S, O or N—$R^{19}$, in which $R^{19}$ is hydrogen or (lower)alkyl; and $R^{20}$ and $R^{21}$ are the same or different and are hydrogen, (lower)alkyl, (lower)alkoxy, (lower)alkylthio, amino, (lower)alkylamino, di(lower)alkylamino, carboxy, hydroxy, hydroxy(lower)alkyl, amino(lower)alkyl, (lower)alkoxy(lower)alkyl, carboxy(lower)alkyl, carboxy(lower)alkylamino, (lower)alkanoylamino, carboxy(lower)alkanoylamino, carbamoyl or N-(lower)alkylcarbamoyl.

Particularly preferred quaternary ammonio groups are N-(lower)alkylpyrrolidinio (and especially N-methylpyrrolidinio), tri(lower)alkylammonio (and especially trimethylammonio), pyridinio, aminopyridinio, formylaminopyridinio, carbamoylpyridinio, amino(lower)alkylpyridinio, carboxypyridinio, hydroxy(lower)alkylpyridinio, N-(lower)alkylcarbamoylpyridinio, (lower)alkylenepyridinio, 2-methylthiazolio and 2-amino-5-thiazolo[4,5-c]pyridinio.

In the compounds of Formula I, particularly preferred values of $R^2$ are (lower)alkyl (and especially methyl), cycloalkyl containing from 3 to 5 carbon atoms, 1-carboxycycloalk-1-yl containing from 3 to 5 carbon atoms, allyl, propargyl and carboxy(lower)alkyl (and especially 2-carboxyprop-2-yl). The most preferred compounds of the invention are (1) 7-[2-(5-amino-1,2,4-thiadiazol-3-yl)-2-methoxyiminoacetamido]-3-[3-(trimethylammonio)-1-propen-1-yl]-3-cephem-4-carboxylate, (2) 7-[2-(5-amino-1,2,4-thiadiazol-3-yl)-2-methoxyiminoacetamido]-3-[3-(1-methylpyrrolidinio)-1-propen-1-yl]-3-cephem-4-carboxylate, (3) 7-[2-(5-amino-1,2,4-thiadiazol-3-yl)-2-methoxyiminoacetamido]-3-[3-pyridinio-1-propen-1-yl]-3-cephem-4-carboxylate, (4) 7-[2-(5-amino-1,2,4-thiadiazol-3-yl)-2-methoxyiminoacetamido]-3-[3-(3-aminopyridinio)-1-propen-1-yl]-3-cephem-4-carboxylate, (5) 7-[2-(5-amino-1,2,4-thiadiazol-3-yl)-2-methoxyiminoacetamido]-3-[3-(3-formylaminopyridinio)-1-propen-1-yl]-3-cephem-4-carboxylate, (6) 7-[2-(5-amino-1,2,4-thiadiazol-3-yl)-2-methoxyiminoacetamido]-3-[3-(3-aminomethylpyridinio)-1-propen-1-yl]-3-cephem-4-carboxylate, (7) 7-[2-(5-amino-1,2,4-thiadiazol-3-yl)-2-methoxyiminoacetamido]-3-[3-(3-carbamoylpyridinio)-1-propen-1-yl]-3-cephem-4-carboxylate, (8) 7-[2-(5-amino-1,2,4-thiadiazol-3-yl)-2-methoxyiminoacetamido]-3-[3-(4-carbamoylpyridinio)-1-propen-1-yl]-3-cephem-4-carboxylate, (9) 7-[2-(5-amino-1,2,4-thiadiazol-3-yl)-2-methoxyiminoacetamido]-3-[3-(2-methylthiazolio)-1-propen-1-yl]-3-cephem-4-carboxylate,

(10) 7-[2-(5-amino-1,2,4-thiadiazol-3-yl)-2-methoxyiminoacetamido]-3-[3-(2-amino-5-thiazolo[4,5-c]pyridinio)-1-propen-1-yl]-3-cephem-4-carboxylate,

(11) 7-[2-(5-amino-1,2,4-thiadiazol-3-yl)-2-methoxyiminoacetamido]-3-[3-(4-hydroxymethylpyridinio)-1-propen-1-yl]-3-cephem-4-carboxylate,

(12) 7-[2-(5-amino-1,2,4-thiadiazol-3-yl)-2-methoxyiminoacetamido]-3-[3-(3-hydroxymethylpyridinio)-1-propen-1-yl]-3-cephem-4-carboxylate,

(13) 7-[2-(5-amino-1,2,4-thiadiazol-3-yl)-2-methoxyiminoacetamido]-3-[3-(4-{N-methylcarbamoyl}pyridinio)-1-propen-1-yl]-3-cephem-4-carboxylate,

(14) 7-[2-(5-amino-1,2,4-thiadiazol-3-yl)-2-methoxyiminoacetamido]-3-[3-(2,3-propylenepyridinio)-1-propen-1-yl]-3-cephem-4-carboxylate,

(15) 7-[2-(5-amino-1,2,4-thiadiazol-3-yl)-2-ethoxyiminoacetamido]-3-[3-(4-carbamoylpyridinio)-1-propen-1-yl]-3-cephem-4-carboxylate,

(16) 7-[2-(5-amino-1,2,4-thiadiazol-3-yl)-2-cyclopentyloxyiminoacetamido]-3-[3-(4-carbamoylpyridinio)-1-propen-1-yl]-3-cephem-4-carboxylate,

(17) 7-[2-(5-amino-1,2,4-thiadiazol-3-yl)-2-allyloxyiminoacetamido]-3-[3-(4-carbamoylpyridinio)-1-propen-1-yl]-3-cephem-4-carboxylate,

(18) 7-[2-(5-amino-1,2,4-thiadiazol-3-yl)-2-propargyloxyiminoacetamido]-3-[3-(4-carbamoylpyridinio)-1-propen-1-yl]-3-cephem-4-carboxylate,

(19) 7-[2-(5-amino-1,2,4-thiadiazol-3-yl)-2-methoxyiminoacetamido]-3-[3-(4-carboxypyridinio)-1-propen-1-yl]-3-cephem-4-carboxylate,

(20) 7-[2-(5-amino-1,2,4-thiadiazol-3-yl)-2-ethoxyiminoacetamido]-3-[3-(4-carboxypyridinio)-2-propen-1-yl]-3-cephem-4-carboxylate,

(21) 7-[2-(5-amino-1,2,4-thiadiazol-3-yl)-2-methoxyiminoacetamido]-3-[3-(3-carboxymethylpyridinio)-1-propen-1-yl]-3-cephem-4-carboxylate and

(22) 7-[2-(5-amino-1,2,4-thiadiazol-3-yl)-2-methoxyiminoacetamido]-3-[3-(4-carboxymethylthiopyridinio)-1-propen-1-yl]-3-cephem-4-carboxylate.

The numbering system utilized herein for the various reactants, intermediates and final products is as follows:

[Roman Numeral] − [Arabic Numeral (if appropriate)] [Letter (if appropriate)].

The Roman Numeral designates whether the compound is a final product [I] or an intermediate or other reactant [all other Roman Numerals]. The Arabic Numerals and Letters are not used in those instances where the overall class (genus) of compounds is meant.

The Arabic Numeral designates the particular meaning of substituent $R^2$. If the particular $R^2$ group contains a carboxyl group which is protected by a conventional carboxyl-protecting group, a "prime" (') is used after the Arabic Numeral to indicate this fact. No "prime" is used if the carboxyl-group is unprotected. A "prime" also is used with the generic $R^2$ substituent (i.e. $R^{2'}$) when generically referring to an $R^2$ group containing a protected carboxyl group.

The Letter at the end of the compound number refers to the particular meaning of the quaternary ammonio group

For convenience, the Arabic Numerals and Letters assigned to some of the preferred $R^2$ groups and quaternary ammonio groups are set forth below.

| Arabic Numeral | | $R^2$ |
|---|---|---|
| 1 | = | methyl |
| 2 | = | ethyl |
| 3 | = | allyl |
| 4 | = | propargyl |
| 5 | = | cyclopentyl |

| Letter | | $-^\oplus N\equiv Q$ |
|---|---|---|
| A | = | 1-methylpyrrolidinio |
| B | = | pyridinio |
| C | = | 2-amino-5-thiazolo[4,5-c]pyridinio |
| D | = | trimethylammonio |
| E | = | 3-aminopyridinio |
| F | = | 3-formylaminopyridinio |
| G | = | 3-carbamoylpyridinio |
| H | = | 4-carbamoylpyridinio |
| I | = | 3-aminomethylpyridinio |
| J | = | 2-methylthiazolio |
| K | = | 3-hydroxymethylpyridinio |
| L | = | 4-hydroxymethylpyridinio |
| M | = | 4-(N—methylcarbamoyl)pyridinio |
| N | = | 4-carboxypyridinio |
| O | = | 2,3-propylenepyridinio |
| P | = | 3-carboxymethylpyridinio |
| Q | = | 4-carboxymethylthiopyridinio |

In the primary evaluation of the compounds of this invention, the Minimum Inhibitory Concentrations (MIC's) of the compounds were determined by the two-fold serial agar dilution method in Mueller-Hinton agar against 32 strains of test organisms in six groups. The geometric means of the MIC's determined in these tests are shown in Table 1.

TABLE 1

| Cmpd. No. | Config. at double bond | Geometric Mean of MIC (mcg/ml) | | | | | |
|---|---|---|---|---|---|---|---|
| | | (G+)-Ia (5) | (G+)-Ib (5) | (G−)-Ia (5) | (G−)-Ib (5) | (G−)-II (5) | (G−)-III (7) |
| I-1A | E/Z = 1/1 | 0.26 | 0.70 | 0.05 | 0.15 | 0.23 | 2.4 |
| I-1A | E/Z = 7/1 | 0.13 | 0.35 | 0.029 | 0.05 | 0.17 | 1.4 |
| I-1B | E | 0.20 | 0.40 | 0.016 | 0.044 | 0.11 | 1.6 |
| I-1B | E/Z = 1/4 | 0.35 | 0.80 | 0.05 | 0.11 | 0.35 | 3.5 |
| I-1C | E | 0.10 | 0.20 | 0.0071 | 0.033 | 0.087 | 3.8 |
| I-1D | E/Z = 1/1 | 0.61 | 1.4 | 0.10 | 0.26 | 0.46 | 2.4 |
| I-1D | E/Z = 10/1 | 0.30 | 0.53 | 0.05 | 0.076 | 0.26 | 1.3 |
| I-1E | E | 0.20 | 0.40 | 0.0094 | 0.029 | 0.10 | 1.4 |
| I-1F | E | 0.15 | 0.40 | 0.0094 | 0.033 | 0.099 | 1.2 |
| I-1G | E | 0.20 | 0.35 | 0.0094 | 0.033 | 0.10 | 1.4 |
| I-1H | E | 0.20 | 0.40 | 0.013 | 0.043 | 0.10 | 0.97 |
| I-1I | E | 0.80 | 1.6 | 0.10 | 0.20 | 0.69 | 3.1 |
| I-1J | E | 0.17 | 0.35 | 0.025 | 0.076 | 0.15 | 1.6 |

TABLE 1-continued

| Cmpd. No. | Config. at double bond | Geometric Mean of MIC (mcg/ml) | | | | | |
|---|---|---|---|---|---|---|---|
| | | (G+)-Ia (5) | (G+)-Ib (5) | (G−)-Ia (5) | (G−)-Ib (5) | (G−)-II (5) | (G−)-III (7) |
| I-1K | E | 0.35 | 0.80 | 0.029 | 0.044 | 0.20 | 3.5 |
| I-1L | E | 0.26 | 0.61 | 0.029 | 0.088 | 0.15 | 2.6 |
| I-1M | E | 0.35 | 0.70 | 0.029 | 0.10 | 0.17 | 2.3 |
| I-1N | E/Z = 7/1 | 1.2 | 1.6 | 0.013 | 0.066 | 0.30 | 5.7 |
| I-1O | E | 0.17 | 0.35 | 0.029 | 0.033 | 0.11 | 14 |
| I-2H | E | 0.20 | 0.40 | 0.014 | 0.057 | 0.15 | 1.4 |
| I-2N | E | 1.2 | 2.1 | 0.016 | 0.11 | 0.35 | 4.7 |
| I-2N | Z | 1.4 | 3.1 | 0.044 | 0.15 | 0.69 | 10 |
| I-3H | E | 0.23 | 0.40 | 0.057 | 0.10 | 0.52 | 1.9 |
| I-4H | E | 0.26 | 0.46 | 0.066 | 0.11 | 0.60 | 2.6 |
| I-5H | E | 0.13 | 0.40 | 0.20 | 0.46 | 2.1 | 4.2 |
| I-1P | E | 0.8 | 1.6 | 0.013 | 0.087 | 0.34 | 14 |
| I-1Q | E | 0.7 | 0.92 | 0.0095 | 0.044 | 0.23 | 14 |

(G+)-Ia: Penicillin-sensitive *S. aureus* (5 strains)
(G+)-Ib: Penicillin-resistant *S. aureus* (5 strains)
(G+)-Ia: Cephalothin-sensitive *E. coli* (2 strains), *Kl. pneumoniae* (1 strain) and *Pr. mirabilis* (2 strains)
(G−)-Ib: Cephalothin-resistant *E. coli* (3 strains) and *Kl. pneumoniae* (2 strains)
(G−)-II: *M. morganii* (1 strain), *Ent. cloacae* (2 strains) and *Ser. marcescens* (2 strains)
(G−)-III: *Ps. aeruginosa* (7 strains)

Table 2, below, gives the Protective Dose$_{50}$ (PD$_{50}$) in mice for a number of the compounds of Formula I against selected microorganisms. Table 3 gives blood levels of various compounds of Formula I upon intramuscular administration of the test compounds to mice at a dosage of 20 mg/kg.

TABLE 2

| Cmpd. No. | PD$_{50}$ (mg/kg) | | |
|---|---|---|---|
| | *S. aureus* Smith | *E. coli* Juhl | *P. aeruginosa* A9843A |
| I-1B | 0.44 | 0.028 | 7.7 |
| I-1B | 0.65 | 0.072 | NT |
| I-1C | 0.22 | 0.013 | NT |
| I-1G | 0.96 | 0.021 | 5.92 |
| I-1H | 0.39 | 0.015 | 3.9 |
| I-1J | 0.35 | 0.029 | NT |
| I-1K | 0.53 | NT | NT |
| I-1M | 0.96 | NT | NT |
| I-1N | 2.0 | NT | NT |
| I-1O | 0.26 | 0.17 | NT |
| I-2N | 5.0 | NT | NT |

NT = Not Tested

TABLE 3

| Cmpd. No. | C$_{max}$ (mcg/ml) | T$_{\frac{1}{2}}$ (min) | AUC (mcg hr/ml) |
|---|---|---|---|
| I-1B | 17 | 21 | 11 |
| I-1C | 21 | 32 | 18 |
| I-1D | 20 | 19 | 11 |
| I-1H | 23 | 16 | 14 |
| I-1J | 19 | 16 | 9.7 |
| I-1K | 24 | 14 | 14 |
| I-1M | 20 | 23 | 14 |
| I-1N | 24 | 19 | 18 |
| I-1O | 28 | 32 | 17 |
| I-2N | 22 | 20 | 12 |
| I-3H | 19 | 47 | 25 |
| I-4H | 27 | 22 | 16 |
| I-5H | 22 | 32 | 18 |

In another aspect, this invention relates to processes for the preparation of the compounds of Formula I. The preferred procedures are shown below in Reaction Schemes 1a, 1b and 1c, while an alternative procedure is shown in Reaction Scheme 2. The abbreviation "Ph" represents the phenyl group. Thus, the —CH(Ph)$_2$ moiety is the benzhydryl group, which is a preferred carboxyl-protecting group. When R$^2$ contains a carboxyl group, it is desirable to protect the carboxyl group with a conventional carboxyl-protecting group such as the t-butyl moiety. Y represents chloro, bromo or iodo.

Reaction Scheme 1a

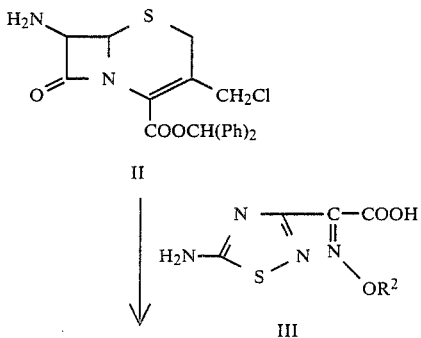

-continued
Reaction Scheme 1a
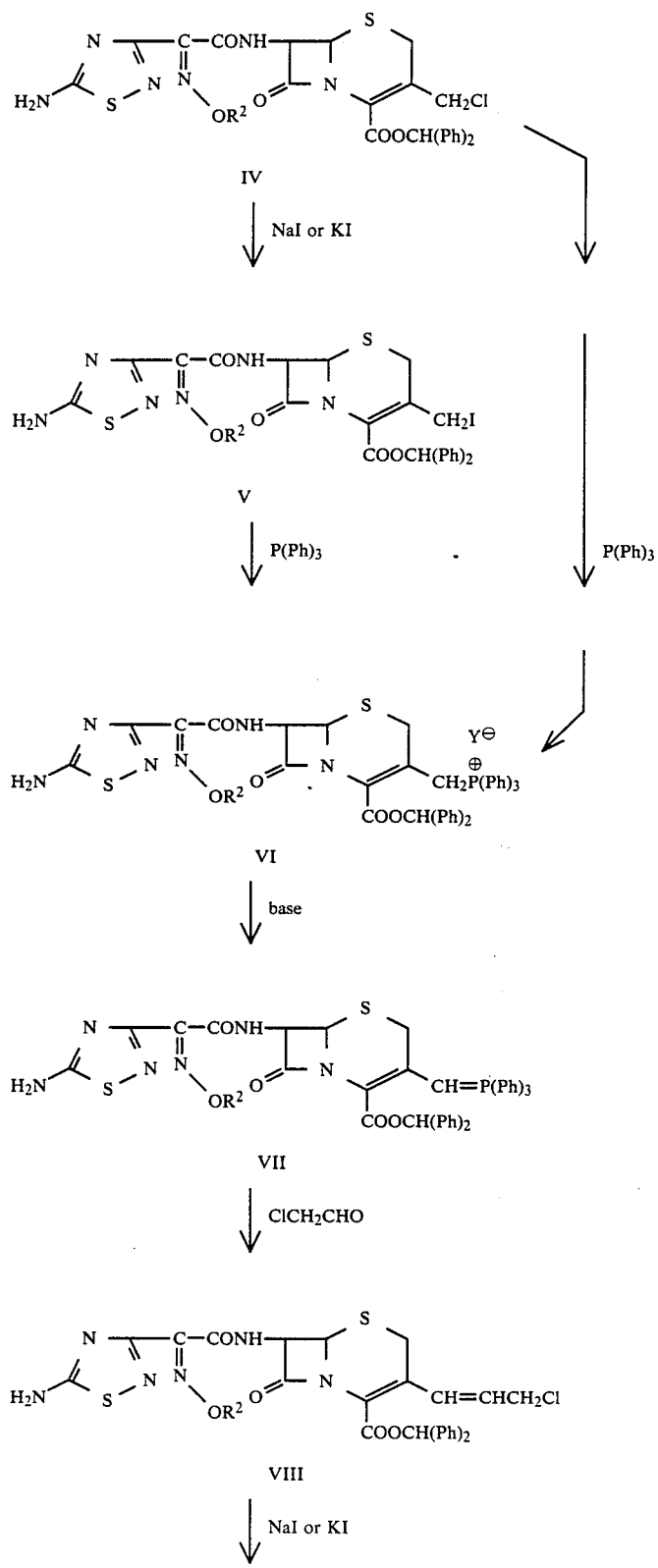

-continued
Reaction Scheme 1a

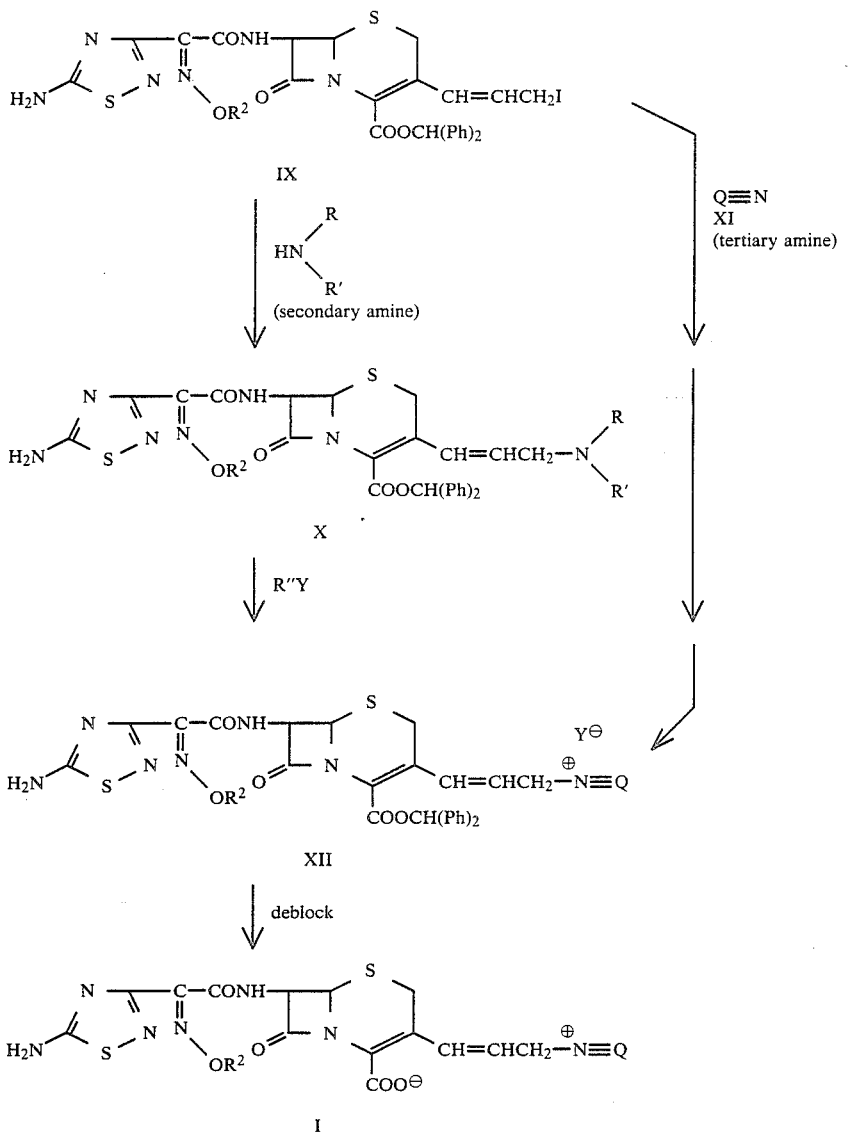

Reaction Scheme 1a shows two alternate means of going from Compound IX to Compound XII. The direct route, utilizing a tertiary amine (XI), is applicable for the preparation of all compounds of Formula I. The indirect route, via Compound X, utilizes a secondary amine as reactant, and is quaternized in the following step. The secondary amine RR'NH may be acyclic (e.g. dimethylamine) or cyclic (e.g. pyrrolidine), and this indirect procedure therefore is suitable for the preparation of compounds of Formula I in which the quaternary ammonio group is acyclic or "mixed" acyclic/cyclic. This indirect route is not suitable for the preparation of compounds of Formula I wherein the quaternary nitrogen is in a fully unsaturated heterocyclic ring (e.g. pyridinio, thiazolio, 2-amino-5-thiazolo[4,5-c]pyridinio, and the like).

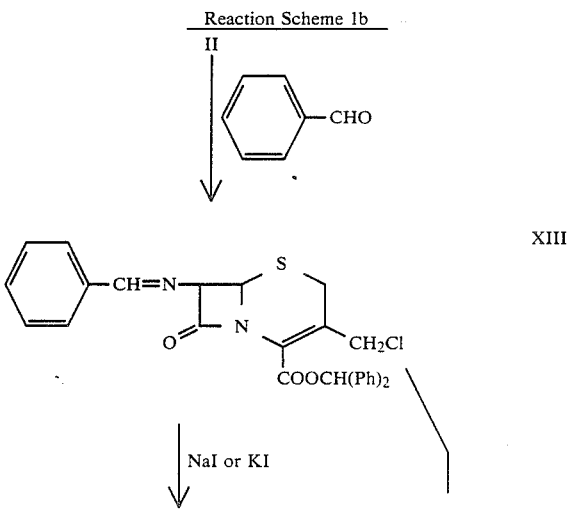

Reaction Scheme 1b -continued
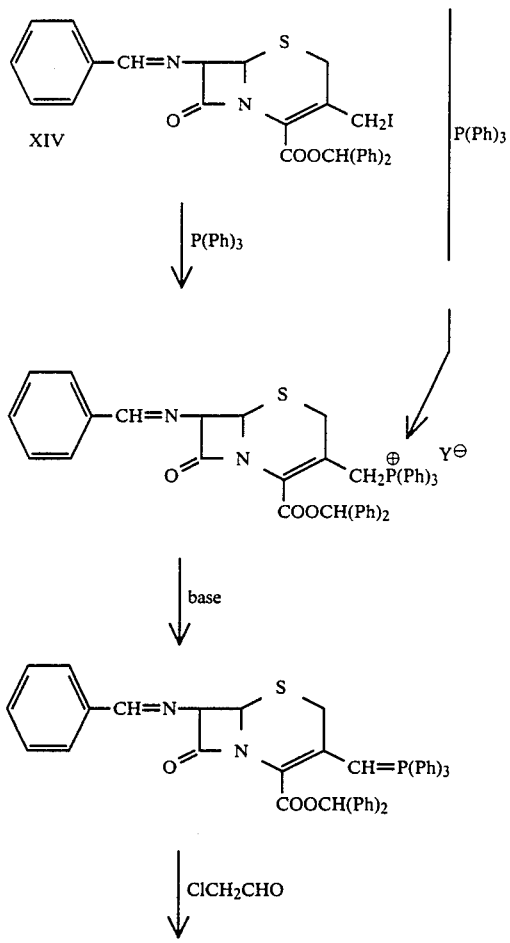
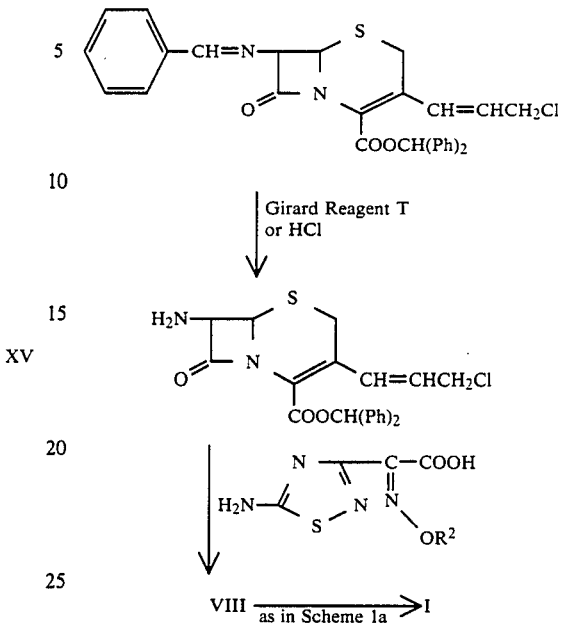
Reaction Scheme 1b is a variation of Reaction Scheme 1a in that the 7-amino group of the starting material (II) is protected as a Schiff base during most of the reaction steps, and the desired 7-side chain acid is added later in the synthesis. Otherwise, the general procedure is similar.
Reaction Scheme 1c
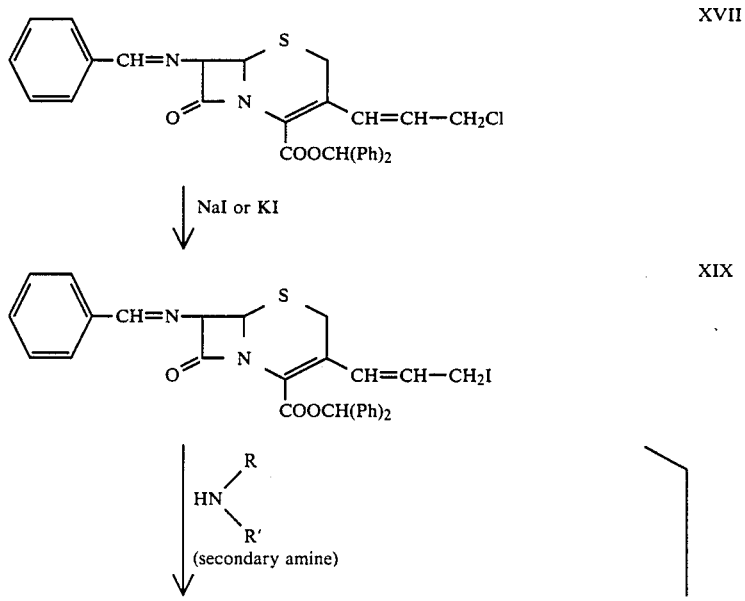

Reaction Scheme 1c
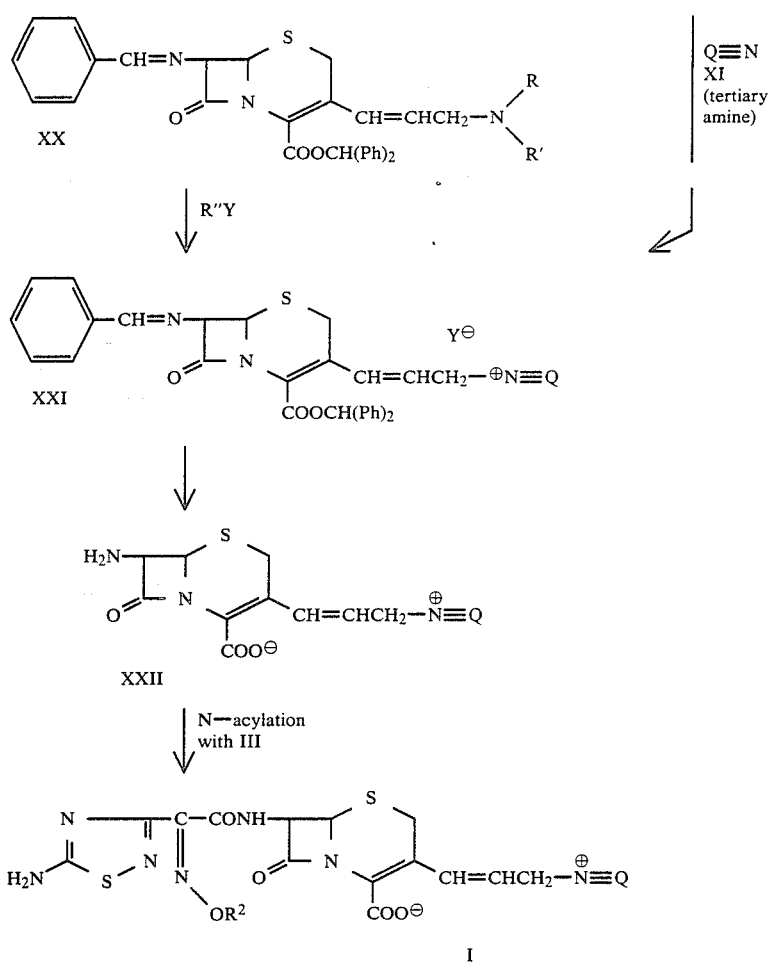
Reaction Scheme 1c is a further variation of Reaction Scheme 1b. In Reaction Schemes 1a and 1b, quaternization of the 3-side chain is the last step, but in Reaction Scheme 1c the last step is acylation of the 7-amino group. The relationship between Reaction Schemes 1a, 1b and 1c is shown in the following flowchart.
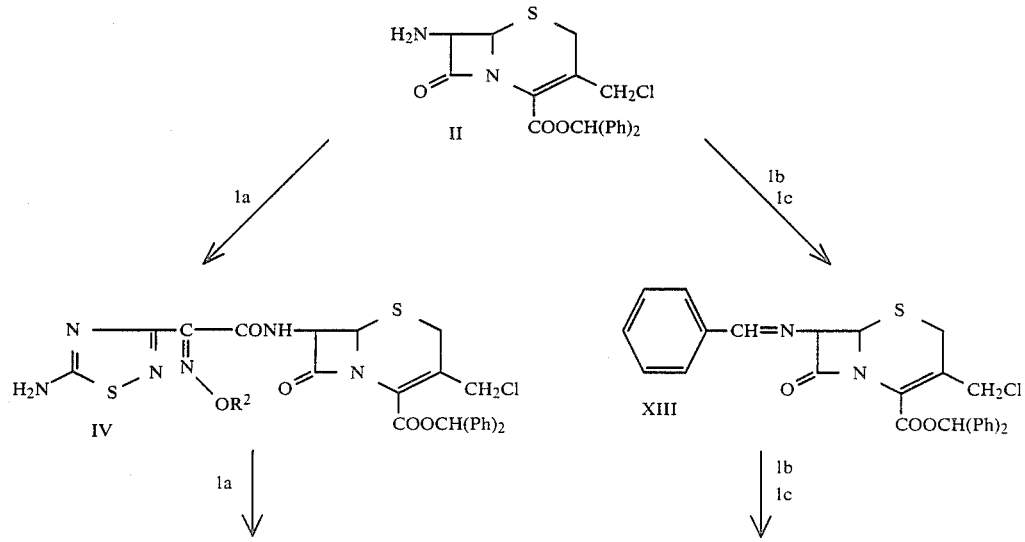

-continued

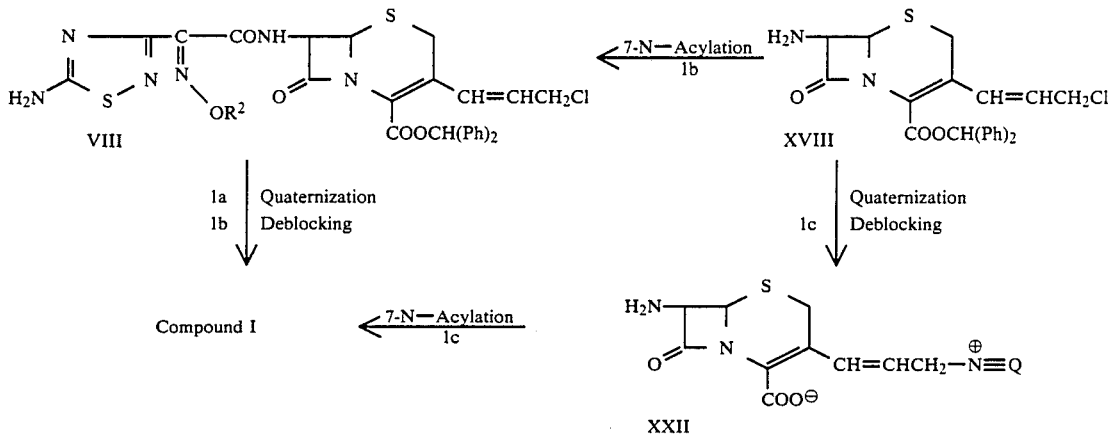

In Reaction Schemes 1a, 1b and 1c, the benzhydryl group was shown as the preferred carboxyl-protecting group. It will be appreciated by those skilled in the art that other carboxyl-protecting groups, well-known in the art, may be used. The acylating acid III may be used in the form of a derivative such as its acid halide, activated ester, mixed acid anhydride, etc., all of which are well-known in the art. We prefer to utilize it in the form of its acid chloride. Acylating acid III also may have its amino group protected by any of the common amino-protecting groups, e.g. N-trityl, N-formyl, or the like. The base used to convert the phosphonium iodide (VI or XV) to give the phosphorylide (VII or XVI) may be NaOH, $Na_2CO_3$, IRA-410 ($OH^-$) resin, IRA($CO_3^=$) resin, or the like, or a mixture thereof. The chloroacetaldehyde used to convert the phosphorylide VII to the 3-chloropropenyl-3-cephem compound VIII (or Compound XVI to Compound XVII) may be the commercially available 40–50% aqueous solution, a distilled solution (e.g. 70%) or the anhydrous aldehyde.

We have found that Compound VIII prepared from Compound VII (Scheme 1a) typically had a Z:E ratio of about 2:1 at the propenyl double bond. Compound VIII prepared from Compound XVIII (Scheme 1b), on the other hand, typically was almost exclusively the Z isomer. The difference may not be in the route used, but in the conditions utilized in the Wittig reaction (VII to VIII or XVI to XVII). We have also found that the use of an appropriate silyl reagent such as N,O-bis(trimethylsilyl)acetamide in the Wittig reaction (VII to VIII in Scheme 1a and XVI to XVII in Scheme 1b) caused improvement of the yields and purity of VIII and XVII. The reaction is preferably carried out with 2–5 equivalents of the silyl reagent. When the chloropropenyl cephem (VIII) was reacted with NaI in acetone to give the iodopropenyl cephem (IX), the double bond in the propenyl group was isomerized from Z to E during the iodination. A short reaction period retained the configuration of the parent Compound VIII to a large extent, while a long reaction period gave primarily the E isomer of Compound IX. However, an excessive reaction time at high temperature gives a lower purity compound IX. We find that about 10 minutes at 25° C. and 2 hours at 5° C. gives pure IX in good yield. When utilizing Reaction Scheme 1c, we have found that, when iodinating compound XIV with NaI, a purer compound is obtained if the acetone solution is diluted with $CCl_4$ when iodination is essentially completed, and the isomerization portion of the reaction is conducted in the acetone-$CCl_4$ mixture. When iodination of the chloropropenyl cephem (XVII) to the iodopropenyl cephem (XIX) was performed with KI in DMF, the isomerization of the double bond from Z to E proceeded as fast as the iodination did. The whole reaction completed within 45 minutes at room temperature to give pure XIX without dilution with $CCl_4$ in the course of the reaction.

Compound XII normally was deblocked without purification, and the final product (I) was purified by reverse phase column chromatography utilizing a glass column containing the packing removed from a Waters' Associates PrepPAK-500/$C_{18}$ cartridge.

Reaction Scheme 2

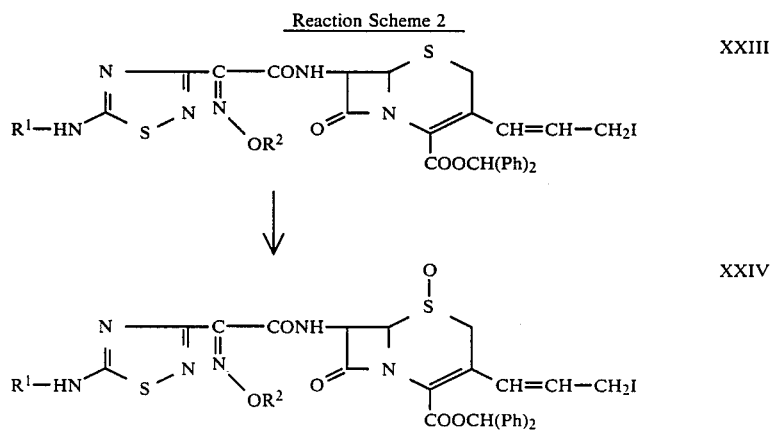

Reaction Scheme 2

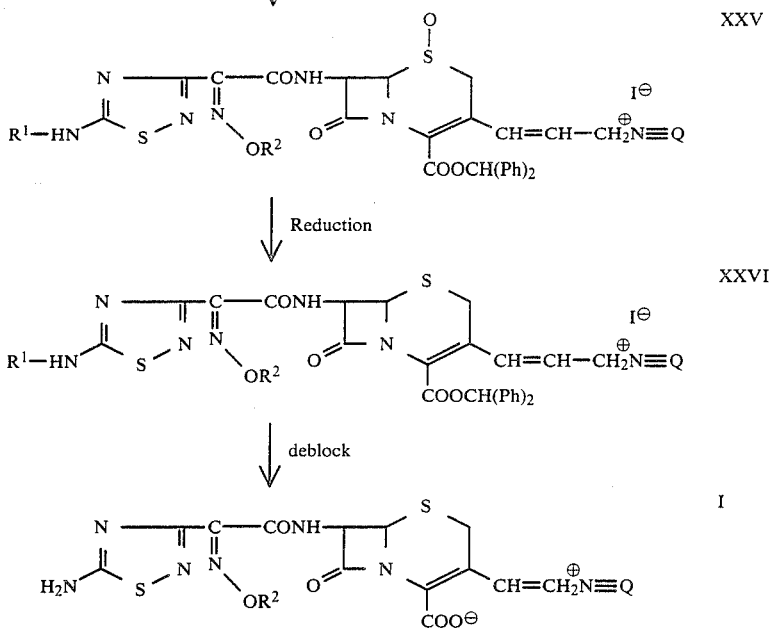

Reaction Scheme 2, shown in brief outline form above, is similar to Reaction Scheme 1a except that Compound XXIII (equivalent to Compound IX of Reaction Scheme 1a) is converted to its S-oxide prior to quaternization. Compound XXV is subsequently reduced, and the remainder of Reaction Scheme 2 is as Reaction Scheme 1a. In Reaction Scheme 2, it is preferred to protect the amino group of the 7-side chain with a known amino-protecting group such as the trityl group.

The acylating acids of Formula III herein are either known compounds or are readily prepared by published procedures. European Patent Specification No. 7,470 published Oct. 12, 1983 (application published Feb. 6, 1980) exemplifies the preparation of compounds of Formula III wherein $R^2$ is methyl, ethyl, propyl and isopropyl. U.S. Pat. No. 4,390,534, referred to in the Prior Art Section, above, exemplifies the preparation of a wide variety of compounds of Formula III wherein $R^2$ is, for example, cyclopentyl, 2-cyclopenten-1-yl, allyl, 2-propynyl, 1-tert. butyloxycarbonyl-1-methylethyl, 1-tert. butyloxycarbonyl-1-cyclopentyl, 1-ethoxycarbonyl-1-methylethyl, tert. butyloxycarbonylmethyl, 1-tert. butyloxycarbonyl-2-methylpropyl, trityl, and the like.

Compound II herein (7-amino-3-chloromethyl-3-cephem-4-carboxylate), used as a starting material in Reaction Schemes 1a, 1b and 1c, is a known compound.

The tertiary amines of Formula XI (and the secondary amines RR'NH) utilized in preparing the quaternary ammonio compounds of this invention are either known compounds or are readily prepared by those of ordinary skill in the art. Many of the amines are commercially available.

The present invention also provides a process for the preparation of compounds of the formula

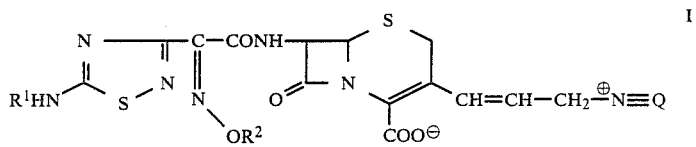

wherein $R^1$ is hydrogen or a conventional amino-protecting group, $R^2$ is hydrogen, a straight or branched chain alkyl group containing from 1 to 4 carbon atoms, a cycloalkyl or cycloalkenyl ring containing from 3 to 6 carbon atoms, or a group of the formula

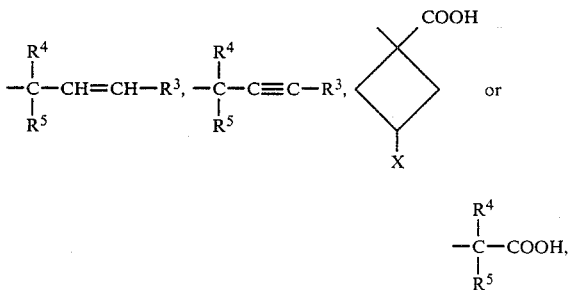

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and

is a quaternary ammonio group, and nontoxic pharmaceutically acceptable salts and physiologically hydrolyzable esters thereof, which process comprises reacting a compound of the formula

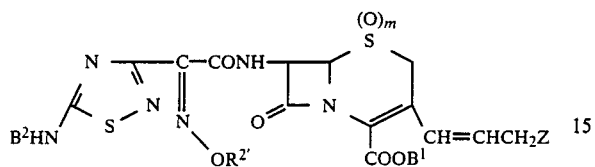

wherein $R^{2'}$ is the same as $R^2$ or is a group of the formula

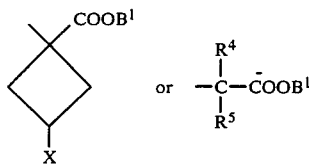

in which X, $R^4$ and $R^5$ are as defined above, $B^1$ is a conventional carboxyl-protecting group, $B^2$ is hydrogen or a conventional amino-protecting group, Z is chloro, bromo or iodo, and m is zero or one, with a tertiary amine Q≡N (or sequentially with a secondary amine RR'NH and a compound of the formula R''Z), and, if m is 1, reducing the sulfoxide by conventional means, and subsequently removing all blocking groups by conventional means.

The present invention also provides a process for the preparation of compounds of the formula

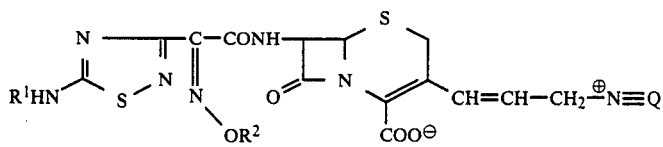

wherein $R^1$ is hydrogen or a conventional amino-protecting group, $R^2$ is hydrogen, a straight or branched chain alkyl group containing from 1 to 4 carbon atoms, a cycloalkyl or cycloalkenyl ring containing from 3 to 6 carbon atoms, or a group of the formula

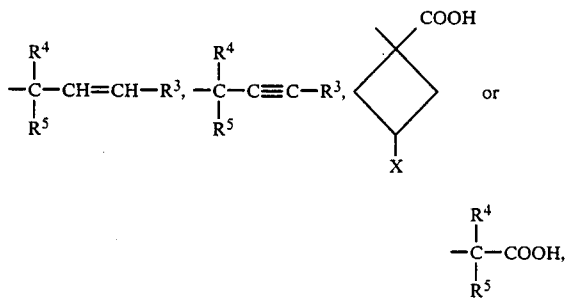

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and

is a quaternary ammonio group, and nontoxic pharmaceutically acceptable salts and physiologically hydrolyzable esters thereof, which process comprises acylating a compound of the formula

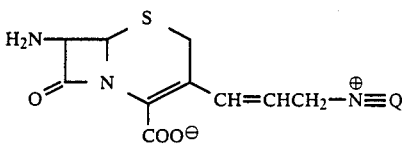

with an acid of the formula

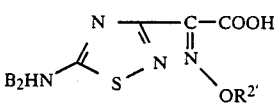

or with an acylating derivative of said acid, wherein $R^{2'}$ is the same as $R^2$ or is a group of the formula

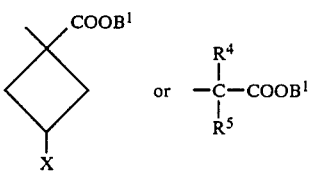

in which X, $R^4$ and $R^5$ are as defined above, $B^1$ is a conventional carboxyl-protecting group and $B^2$ is hydrogen or a conventional amino-protecting group.

The reactions are carried out in a non-aqueous organic solvent such as dimethyl sulfoxide, hexamethylphosphoramide, methylene chloride, chloroform, ethyl ether, hexane, ethyl acetate, tetrahydrofuran, acetonitrile and the like, or mixtures of such solvents. The reactions are conveniently carried out at a temperature of from about −10° C. to about +50° C.; we normally prefer to conduct the reactions at room temperature. During the quaternization step, at least one mole of the tertiary amine should be used per mole of Compound IX, XIX, XXIII or XXIV; we normally prefer to utilize from about 25% to 100% excess of the tertiary amine.

Carboxyl-protecting groups suitable for use as $B^1$ in the above reactions are well-known to those skilled in the art and include aralkyl groups such as benzyl, p-methoxybenzyl, p-nitrobenzyl and diphenylmethyl (benzhydryl); alkyl groups such as t-butyl; haloalkyl groups such as 2,2,2-trichloroethyl, and other carboxyl protecting groups described in the literature, e.g. in U.K. Pat. No. 1,399,086. We prefer to utilize carboxyl-protecting groups which are readily removed by treatment with acid. Particularly preferred carboxyl-protecting groups are the benzhydryl and t-butyl moieties.

Amino-protecting groups suitable for use as $B^2$ are also well-known in the art, and include the trityl group and acyl groups such as chloroacetyl, formyl and trichloroethoxycarbonyl. Amino-protecting groups which are readily removed by treatment with acid, e.g. the trityl group, are preferred.

When the cephalosporin nucleus is utilized in the form of the 1-oxide (m=1), the 1-oxide is prepared by known procedures such as oxidation with m-chloroperbenzoic acid, peracetic acid, sodium tungstate, etc. The 1-oxide subsequently may be reduced by known procedures, e.g. reduction of the corresponding alkoxysulfonium salt with iodide ion in an aqueous medium. The alkoxysulfonium salt itself is readily prepared by treatment of the 1-oxide with, for example, acetyl chloride.

In another aspect, this invention relates to novel intermediates of the formula

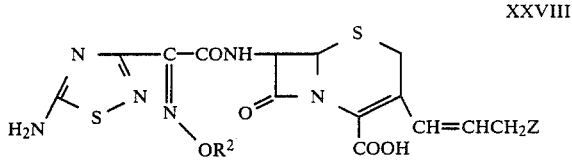

XXVIII wherein Z is chloro, bromo, or iodo, $R^2$ is hydrogen, a straight or branched chain alkyl group containing from 1 to 4 carbon atoms, a cycloalkyl or cycloalkenyl ring containing from 3 to 6 carbon atoms, or a group of the formula

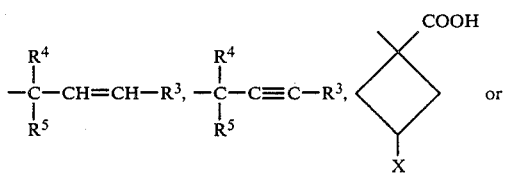

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and salts and esters thereof. Also included are compounds of Formula XXVIII in which the amino and/or carboxyl groups are protected by conventional amino-protecting or carboxyl-protecting groups.

In still another aspect, this invention relates to novel intermediates of the formula

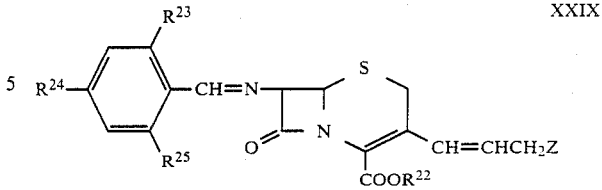

XXIX wherein $R^{22}$ is hydrogen or a conventional carboxyl-protecting group, and $R^{23}$, $R^{24}$ and $R^{25}$ are the same or different and are hydrogen, hydroxy, (lower)alkyl or (lower)alkoxy; or a salt, solvate, hydrate or ester thereof.

In still another aspect, this invention relates to novel intermediates of the formula

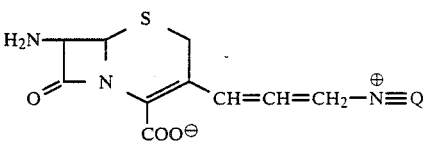

XXII wherein $-\overset{\oplus}{N}\equiv Q$ is a quaternary ammonio group; or a salt, ester, solvate or hydrate thereof.

As used herein, the terms acylamino and acyloxy refer to an acylated amino or acylated hydroxy group in which the acyl moiety is (lower)alkanoyl (e.g. formyl, acetyl, propionyl, butyryl, isobutyryl, isovaleryl, etc.), aroyl (e.g. benzoyl, etc.), (lower)alkanesulfonyl (e.g. mesyl, ethanesulfonyl, etc.) or arylsulfonyl (e.g. benzenesulfonyl, tosyl, etc.).

As used herein, the terms "(lower)alkyl", "(lower)alkoxy", "(lower)alkylthio" (or the like) mean straight or branched chain alkyl, alkoxy, alkylthio (or the like) groups containing from 1 to 6 carbon atoms, inclusive. Similarly, the terms (lower)alkenyl and (lower)alkynyl mean alkenyl or alkynyl groups containing from 2 to 6 carbon atoms.

EXAMPLE 1

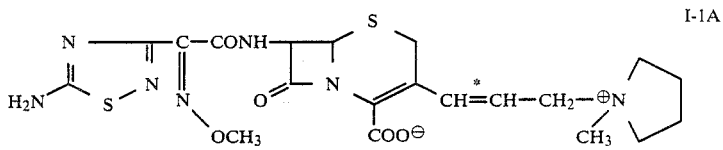

I-1A

*Z/E = 1/1

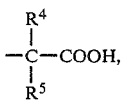

7-[2-(5-Amino-1,2,4-thiadiazol-3-yl)-2-methoxyiminoacetamido]-3-[3-(1-methylpyrrolidinio)-1-propen-1-yl]-3-cephem-4-carboxylate (I-1A)

To a solution of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (Z/E=2/1, 150 mg, 0.21 mmole) in ethyl acetate (2 ml) was added a solution of 1-methylpyrrolidine (36 mg, 0.42 mmole) in ethyl acetate (1 ml) in one portion with stirring. The mixture was stirred for 15 minutes and diluted with isopropyl ether (10 ml) to form a precipitate, which was collected by filtration. A mixture of the solid (130 mg), formic acid (1 ml) and concentrated HCl (0.1 ml) was stirred at room temperature. After 1 hour, the reaction mixture was concentrated under reduced pressure, diluted with water (20 ml) and filtered. The aqueous solution was passed through a reverse phase column (the packing of PrepPAK-500/C$_{18}$ cartridge, 100 ml), eluting with water and 10% CH$_3$OH. The desired fractions were collected, and concentrated in vacuo to a small volume and freeze-dried to give 13 mg (12%) of the title compound (I-1A) (Z/E=1/1), melting at >280° C. (dec.).

IR: $\nu_{max}^{KBr}$ cm$^{-1}$ 3400, 1760, 1660, 1610.

UV: $\lambda_{max}^{Phosphate\ buffer\ (pH\ 7)}$ nm (E$_{1\ cm}^{1\%}$) 236 (372), 288 (322).

NMR: $\delta_{ppm}^{D2O}$ 2.31 (4H, m,

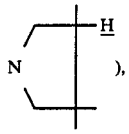), 3.12 (3H, s, N—CH$_3$), 3.6 (5H, m, 2-H &

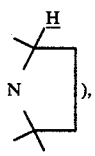), 3.79 (1H, s, 2-H), 4.1 (2H, d, J=8, CH$_2$N), 4.2 (3H, s, OCH$_3$), 5.36 (1H, d, J=4.5, 6-H), 5.95 (3H, m, 7-H & 3-CH=CH), 6.66 (½H, d, J=10, 3-CH cis), 7.0 (½H, d, J=16, 3-CH trans).

EXAMPLE 2

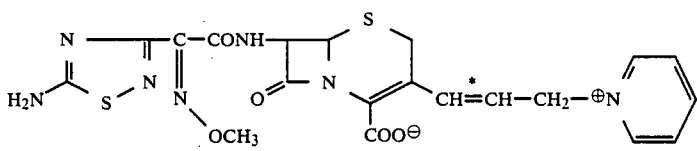

*E

7-[2-(5-Amino-1,2,4-thiadiazol-3-yl)-2-methoxyiminoacetamido]-3-[3-pyridinio-1-propen-1-yl]-3-cephem-4-carboxylate (I-1B)

A mixture of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (E, 716 mg, 1 mmole), pyridine (158 mg, 2 mmoles) in dimethylsulfoxide (DMSO) (1 ml) was stirred for 1 hour at room temperature. To the mixture was added ethyl acetate (20 ml) to precipitate a solid (620 mg), which was added to formic acid (6 ml) containing sodium bisulfite (60 mg). The mixture was stirred for 30 minutes at 40° C. and concentrated to dryness. The residue was dissolved in H$_2$O (40 ml) and some insolubles were removed. The aqueous solution was charged on a column of reverse phase (PrepPAK-500/C$_{18}$, 100 ml) eluting with H$_2$O (300 ml) and 5% aqueous CH$_3$OH (800 ml), and the eluate was monitored by uv (254 nm) and HPLC. The fractions (5% aqueous CH$_3$OH) containing the desired product were combined, concentrated to a small volume and lyophilized to yield 40 mg (8%) of the title compound (I-1B), melting at >200° C. (dec.).

IR: $\nu_{max}^{KBr}$ cm$^{-1}$ 3350, 1760, 1660, 1600.

UV: $\lambda_{max}^{Phosphate\ buffer\ (pH\ 7)}$ nm (E$_{1\ cm}^{1\%}$) 240 (352), 258 (366), 267 (279), 290 (469).

NMR: $\delta_{ppm}^{D2O+DMSO-d6}$ 3.74 (2H, br-s, 2-H), 4.20 (3H, s, OCH$_3$), 5.92 (1H, d, J=4.5, 7-H), 6.15 (1H, m, 3-CH=CH), 7.04 (1H, d, J=16, 3-CH trans), 8.2 (2H, m, Py-H$_{3,5}$), 8.62 (1H, m, Py-H$_4$), 8.97 (2H, m, Py-H$_{2,6}$).

EXAMPLE 3

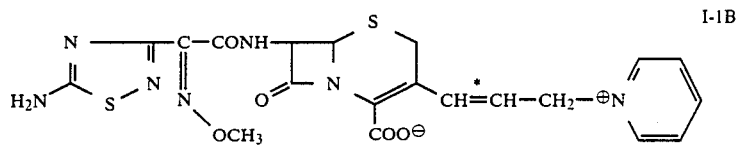

*Z/E = 4/1

7-[2-(5-Amino-1,2,4-thiadiazol-3-yl)-2-methoxyiminoacetamido]-3-[3-pyridinio-1-propen-1-yl]-3-cephem-4-carboxylate (I-1B)

The chloropropenyl compound, diphenylmethyl 7-[2-(5-amino-1,2,4-thiadiazol-3-yl)-2-methoxyiminoacetamido]-3-(3-chloro-1-propen-1-yl)-3-cephem-4-carboxylate (VIII-1) (Z, 937 mg, 1.5 mmoles) was added to a stirred solution of pyridine (237 mg, 3 mmoles) in DMSO (3 ml) containing NaI (11 mg, 0.075 mmole). The mixture was allowed to stand overnight at room temperature in the dark. The mixture was diluted with ethyl acetate (30 ml) to separate the precipitate which was then collected by filtration, washed with ethyl acetate (10 ml) and dried to give 350 mg of the blocked product. The precipitate was treated with formic acid (3.4 ml) containing sodium bisulfite (34 mg) for 30 minutes at 40° C. After removal of the formic acid, the residue was purified by reverse phase column chromatography (packing of PrepPAK-500/C$_{18}$ cartridge, 100 ml) by eluting with 5% aqueous CH$_3$OH. The fractions containing the desired product were combined on the basis of HPLC analysis, evaporated under reduced pressure and lyophilized to give 41 mg (5.5%) of the title compound (I-1B) (Z/E=4/1). Mp. >200° C. (dec.).

IR: $\nu_{max}^{KBr}$ cm$^{-1}$ 3300, 1760, 1660, 1600.

UV: $\lambda_{max}^{Phosphate\ buffer\ (pH\ 7)}$ nm (E$_{1\ cm}^{1\%}$) 237 (386), 250 (377), 258 (369), 265 (347), 280 (311).

NMR: $\delta_{ppm}^{D2O}$ 3.45 & 3.76 (each 1H, d, J=16, 2-H), 4.18 (3H, s, OCH$_3$), 5.34 (3H, m, CH=CH—CH$_2$ & 6-H), 5.92 (1H, d, J=4.5, 7-H), 6.58 (4/5H, d, J=11, 3-CH cis), 7.03 (1/5H, d, J=16, 3-CH trans), 8.12 (2H, m, Py-H$_{3,5}$), 8.56 (1H, m, Py-H$_4$), 8.82 (2H, m, Py-H$_{2,6}$).

EXAMPLE 4

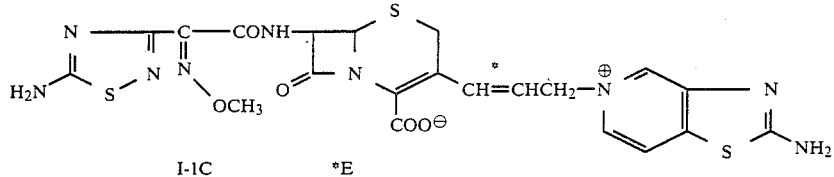

I-1C     *E

7-[2-(5-Amino-1,2,4-thiadiazol-3-yl)-2-methoxyiminoacetamido]-3-[3-(2-amino-5-thiazolo[4,5-c]pyridinio)-1-propen-1-yl]-3-cephem-4-carboxylate (I-1C)

A stirred solution of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (E isomer, 714 mg, 1 mmole), 2-aminothiazolo[4,5-c]pyridine [prepared according to the procedure of T. Takahashi et al., Pharm. Bull (Japan), 2, 34 (1954)] and dry DMSO (1 ml) was kept for 1 hour at room temperature. To the reaction mixture was added ethyl acetate (20 ml) to give a yellow powder (710 mg). Formic acid (7 ml) and sodium bisulfite (70 mg) were added to the powder (700 mg), and the mixture was stirred for 30 minutes at 40°–45° C. After evaporation, the residue was triturated with H$_2$O (40 ml). Insolubles were filtered off, and the filtrate was chromatographed over a reverse phase column (PrepPAK-500/C$_{18}$, 100 ml), with H$_2$O and 10% CH$_3$OH as eluant. The fractions containing the desired product were combined, and the solvent was removed under reduced pressure. Lyophilization gave the desired product (I-1C) as a colorless amorphous powder of the E isomer. Yield 110 mg (19%). Mp. >200° C. (dec.).

IR: $\nu_{max}^{KBr}$ cm$^{-1}$ 3300, 1760, 1660, 1630, 1600.

UV: $\nu_{max}^{Phosphate\ buffer\ (pH\ 7)}$ nm (E$_{1\ cm}^{1\%}$) 245 (499), 285 (286).

NMR: $\delta_{ppm}^{DMSO-d6+D^2O}$ 3.86 (3H, s, OCH$_3$), 4.98 (1H, d, J=4.5, 6-H), 5.2 (2H, m, CH=CH—CH$_2$), 5.57 (1H, m, 3-CH=CH), 5.96 (1H, m, 7-H), 7.16 (1H, d, J=16, 3-CH trans), 8.36 & 8.45 (each 1H, d, J=7, Py-H), 8.92 (1H, s, Py-H).

EXAMPLE 5

7-[2-(5-Amino-1,2,4-thiadiazol-3-yl)-2-methoxyiminoacetamido]-3-(3-trimethylammonio-1-propen-1-yl)-3-cephem-4-carboxylate (I-1D)

To a solution of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (Z/E=2/1, 490 mg, 0.68 mmole) in ethyl acetate (14 ml) was added a 0.1M trimethylamine solution in ether (13.6 ml) in one portion. The mixture was stirred for 10 minutes and evaporated to dryness, and the residue was triturated with ether (20 ml). The resulting solid (490 mg) was added to trifluoroacetic acid (0.2 ml) containing one drop of anisole. After 1.5 hours' stirring, the mixture was evaporated to dryness under reduced pressure and the residual oil was triturated with ether (20 ml). The resulting precipitate was collected by filtration and dissolved in H$_2$O (20 ml). Some insolubles were removed, and the aqueous solution was eluted on a C$_{18}$ reverse phase column (the packing of PrepPAK-500/C$_{18}$ cartridge, Waters' 30 ml) using water as eluant. Fractions containing the desired compound were combined and concentrated to a small volume and lyophilized to afford 30 mg (9.2%) of the title compound (I-1D) (8/E=1/1) as a colorless amorphous powder, melting at >150° C. (dec.).

IR: $\nu_{max}^{KBr}$ cm$^{-1}$ 3300, 1770, 1670, 1605.

UV: $\lambda_{max}^{Phosphate\ buffer\ (pH\ 7)}$ nm (E$_{1\ cm}^{1\%}$) 236 (389), 287 (343).

NMR: $\delta_{ppm}^{D2O}$ 3.45 & 3.7 (1H, d, J=16, 2-H), 3.81 (1H, s, 2-H), 4.1 (2H, d, J=8, —CH$_2$N$\oplus$), 4.21 (3H, s, OCH$_3$), 5.39 (1H, d, J=4.5, 6-H), 5.95 (2H, m, 3-CH=CH & 7-H), 6.61 (½H, d, J=11, 3-CH cis), 7.05 (½H, d, J=16, 3-CH trans).

EXAMPLE 6

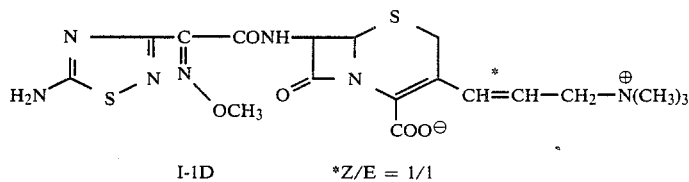

I-1D     *Z/E = 1/1

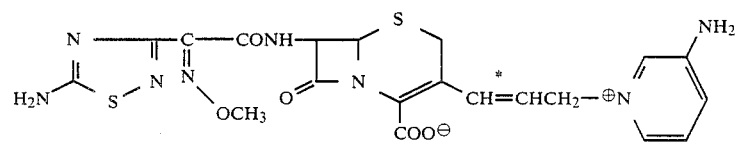

I-1E     *E

7-[2-(5-Amino-1,2,4-thiadiazol-3-yl)-2-methoxyiminoacetamido]-3-[3-(3-aminopyridinio)-1-propen-1-yl]-3-cephem-4-carboxylate (I-1E)

Diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (E, 716 mg, 1 mmole) was added to a stirred solution of 3-aminopyridine (188 mg, 2 mmoles) in DMSO (1 ml). The mixture was stirred for 1 hour and diluted with ethyl acetate (20 ml). The resulting precipitate was collected by filtration, washed with ethyl acetate and dried to give 520 mg of yellow powder. A mixture of the powder (500 mg), formic acid (5 ml) and sodium bisulfite (50 mg) was stirred for 30 minutes at 40° C. The mixture was concentrated in vacuo, dissolved in $H_2O$ (40 ml) and filtered to remove insolubles. The aqueous solution was chromatographed on a column of reverse phase (packing of PrepPAK-500/$C_{18}$, 100 ml), with 7.5% aqueous $CH_3OH$ elution. The fractions containing the desired compound were evaporated and lyophilized to give the title compound (I-1E) (7 mg, 1.4%), melting at >185° C. (dec.).

IR: $\nu_{max}^{KBr}$ cm$^{-1}$ 3400, 1765, 1675, 1620, 1600.

UV: $\lambda_{max}^{Phosphate\ buffer\ (pH\ 7)}$ nm ($E_1\ _{cm}^{1\%}$) 246 (403), 290 (468).

NMR: $\delta_{ppm}^{D_2O}$ 3.72 (2H, m, 2-H), 4.14 (3H, s, $OCH_3$), 5.35 (3H, m, 6-H & CH=CH—$CH_2$), 5.9 (1H, d, J=4.5, 7-H), 6.1 (1H, m, 3-CH=CH), 7.05 (1H, d, J=16, 3-CH, trans), 8.1 (1H, m, Py-$H_5$), 8.54 (1H, br-s, Py-$H_6$), 8.68 (1H, m, Py-$H_4$), 9.4 (1H, m, Py-$H_2$).

Treatment of IX-1 (716 mg, 1 mmole) with 3-t-butoxycarbonylaminopyridine (324 mg, 2 mmoles) by a procedure similar to that described above gave 12 mg (2.3%) of I-1E.

EXAMPLE 7

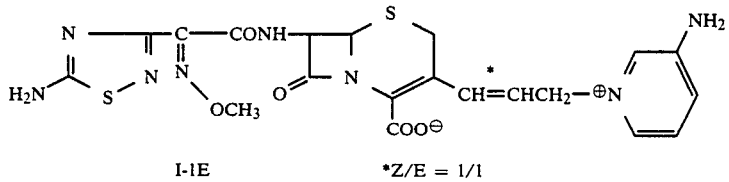

I-1E  *Z/E = 1/1

7-[2-(5-Amino-1,2,4-thiadiazol-3-yl)-2-methoxyiminoacetamido]-3-[3-(3-amino-1-pyridinio)-1-propen-1-yl]-3-cephem-4-carboxylate (I-1E)

A mixture of diphenylmethyl 7-[2-(5-amino-1,2,4-thiadiazol-3-yl)-2-methoxyiminoacetamido-3-(3-iodo-1-propen-1-yl)-3-cephem-4-carboxylate (IX-1) (Z/E=2/1, 500 mg, 0.7 mmole) and 3-aminopyridine (66 mg, 0.7 mmole) in dimethylsulfoxide (1 ml) was stirred for 20 minutes at room temperature. The mixture was diluted with ethyl acetate (10 ml) and ether (10 ml), and the resulting precipitarte was collected by filtration, washed with ether (10 ml) and dried. The quaternized salt was dissolved in formic acid (3 ml) containing concentrated HCl (0.3 ml) and stirred for 1.5 hours at room temperature. The mixture was concentrated to dryness under reduced pressure. The residue was dissolved in 2% HCl (10 ml) and filtered. The aqueous layer was chromatographed on a reverse phase column (PrepPAK-500/$C_{18}$, 100 ml). After washing with water (500 ml), the column was eluted with 5% aqueous $CH_3OH$. The fractions containing the title compound were combined, concentrated in vacuo and freeze-dried to give 15 mg (4.2%) of the title compound (I-1E) (Z/E=1/1) as a colorless amorphous powder. Mp. >160° C. (dec.).

IR: $\nu_{max}^{KBr}$ cm$^{-1}$ 3400, 1765, 1675, 1620, 1600.

UV: $\lambda_{max}^{Phosphate\ buffer\ (pH\ 7)}$ nm ($E_1\ _{cm}^{1\%}$) 244 (434), 287 (333).

NMR: $\delta_{ppm}^{DMSO-d_6}$+$D_2O$ 3.73 (2H, m), 4.14 (3H, s, $OCH_3$), 5.35 (3H, m, 6-H & CH=CH-$CH_2$), 6.0 (2H, m, 7-H & 3-CH=CH), 6.6 (½H, d, J=11, 3-CH cis), 7.05 (½H, d, J=16, 3-CH trans), 8.08 (1H, m, Py-$H_5$), 8.6 (2H, m, Py-$H_{4,6}$), 9.4 (1H, m, Py-$H_2$).

EXAMPLE 8

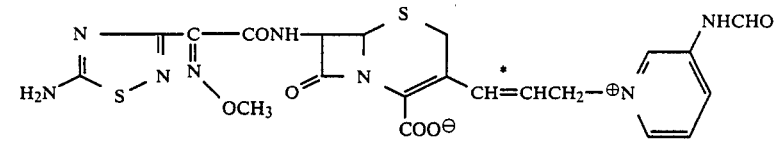

I-1F  *E

7-[2-(5-Amino-1,2,4-thiadiazol-3-yl)-2-methoxyiminoacetamido]-3-[3-(3-formylaminopyridinio)-1-propen-1-yl]-3-cephem-4-carboxylate (I-1F)

A mixture of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (E, 716 mg, 1 mmole) and 3-formylaminopyridine [prepared according to the procedure of N. Enomoto et al., Bull. Chem. Soc. Japan, 45, 2665 (1972)] (244 mg, 2 mmoles) in DMSO (2 ml) was stirred at room temperature for 1 hour, and poured into ethyl acetate (200 ml). The precipitate was collected by filtration, washed well with ethyl acetate and dried. A mixture of the quaternized salt (500 mg) and sodium bisulfite (50 mg) in HCOOH (5 ml) was stirred at 40°–50° C. for 80 minutes and evaporated to dryness in vacuo. The residue was dissolved in water (40 ml), neutralized with $NaHCO_3$ and then filtered to remove insoluble material. The clear filtrate was chromatographed on a reverse phase column, PrepPAK-500/$C_{18}$ (100 ml), with water and 5% $CH_3OH$, 10% $CH_3OH$, 20% $CH_3OH$ and 30% $CH_3OH$. The fractions containing the desired compound were combined, concentrated in vacuo and lyophilized to give 16 mg (2.9%) of the title compound (I-1F) (E) as a tan powder. Mp. >170° C. (dec.).

IR: $\nu_{max}^{KBr}$ cm$^{-1}$ 3340(br), 1760, 1670, 1620(br), 1590.

UV: $\lambda_{max}^{Phosphate\ buffer\ (pH\ 7)}$ nm (E$_{1\ cm}^{1\%}$) 218 (428), 248 (362), 290 (474).

NMR: $\delta_{ppm}^{D2O+NaHCO_3}$ 3.68 (2H, br, 2-H), 4.15 (3H, s, OCH$_3$), 5.91 (1H, d, J=4.5, 7-H), 6.25 (1H, m, CH=CH—CH$_2$), 6.98 (1H, d, J=16, 3-CH trans), 8.8–7.9 (4H, m, Py-H), 9.38 (1H, br, NHCHO).

EXAMPLE 9

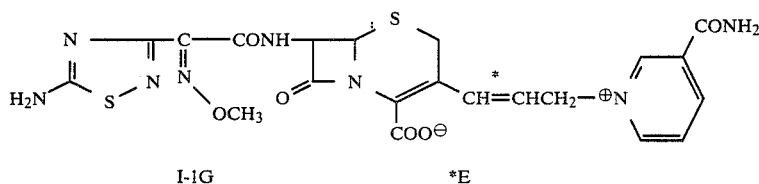

I-1G       *E

7-[2-(5-Amino-1,2,4-thiadiazol-3-yl)-2-methoxyiminoacetamido]-3-[3-(3-carbamoylpyridinio)-1-propen-1-yl]-3-cephem-4-carboxylate (I-1G)

To a solution of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (E, 716 mg, 1 mmole) in DMSO (2 ml) was added nicotinamide (244 mg, 2 mmoles), and the mixture was stirred at ambient temperature for 1.5 hours and poured into ethyl acetate (200 ml) with stirring. The resulting precipitate was collected by filtration. The quaternized salt (500 mg) was dissolved in HCOOH (5 ml) in the presence of sodium bisulfite (50 mg), and the mixture was heated at 40°–50° C. for 40 minutes, with stirring, and evaporated to dryness. The residue was dissolved in water (40 ml) and an insoluble solid was filtered off and washed with a small amount of water. The filtrate and wash were combined and chromatographed on a reverse phase column, PrepPAK-500/C$_{18}$ (100 ml). After elution with water and 5%, 10% and 20% aqueous CH$_3$OH, successively, the fractions containing the desired material were combined, concentrated in vacuo and freeze-dried to yield 21 mg (3.8%) of the title compound (I-1G) (E) as a yellow powder. Mp. >175° C. (dec.).

IR: $\nu_{max}^{KBr}$ cm$^{-1}$ 3340 (br), 1760, 1670, 1600.

UV: $\lambda_{max}^{Phosphate\ buffer\ (pH\ 7)}$ nm (E$^{1\%}$) 235 (326), 274 (sh, 405), 290 (446).

NMR: $\delta_{ppm}^{D2O+NaHCO_3}$ 3.68 (2H, br, 2-H), 4.15 (3H, s, OCH$_3$), 5.32 (1H, d, J=4.5, 6-H), 5.45 (1H, d, J=7, CH=CH—CH$_2$), 5.88 (1H, d, J=4.5, 7-H), 6.15 (1H, d-t, J=16 & 7, 3-CH=CH), 7.00 (1H, d, J=16, 3-CH trans), 8.23 (1H, m, Py-H$_5$), 9.03 (2H, m, Py-H$_{4\&6}$), 9.34 (1H, s, Py-H$_2$).

EXAMPLE 10

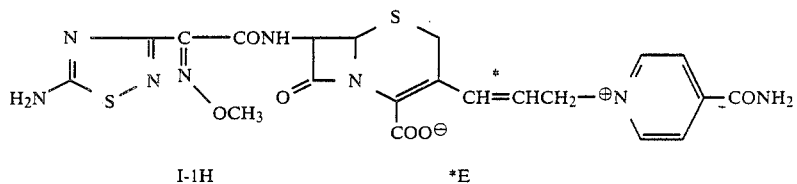

I-1H       *E

7-[2-(5-Amino-1,2,4-thiadiazol-3-yl)-2-methoxyiminoacetamido]-3-[3-(4-carbamoylpyridinio)-1-propen-1-yl]-3-cephem-4-carboxylate (I-1H)

To a stirred solution of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (E, 716 mg, 1 mmole) in dry DMSO (2 ml) was added isonicotinamide (244 mg, 2 mmoles). The mixture was stirred at room temperature for 1 hour and then poured into ethyl acetate (200 ml). The resulting precipitate was collected by filtration, washed well with ethyl acetate and dried. A stirred mixture of the quaternized material (400 mg) and sodium bisulfite (40 mg) in HCOOH (4 ml) was heated at 40°–50° C. for 1 hour, and evaporated to dryness under reduced pressure. The crude solid was dissolved in water (40 ml). After filtration of an insoluble material, the filtrate was chromatographed on a reverse phase column (packing of PrepPAK/C$_{18}$, 100 ml) using water and 5%, 10%, 20% and 30% aqueous CH$_3$OH as eluant. The fractions containing the desired compound were combined, evaporated and lyophilized to give 21 mg (3.8%) of the title compound (I-1H) (E) as a pale yellow powder. Mp. >180° C. (dec.).

IR: $\nu_{max}^{KBr}$ cm$^{-1}$ 3340 (br), 1760, 1670, 1600.

UV: $\lambda_{max}^{Phosphate\ buffer\ (pH\ 7)}$ nm (E$_{1\ cm}^{1\%}$) 222 (362), 285 (452).

NMR: $\delta_{ppm}^{D2O+NaHCO_3}$ 3.68 (2H, br, 2-H), 4.15 (3H, s, OCH$_3$), 5.33 (1H, d, J=4.5, 6-H), 5.46 (2H, d, J=7, CH=CH-CH$_2$), 5.90 (1H, d, J=4.5, 7-H), 6.17 (1H, d-t, J=16 & 7, 3-CH=CH), 7.02 (1H, d, J=16, 3-CH trans), 8.43 & 9.09 (each 2H, d, J=7, Py-H).

EXAMPLE 11

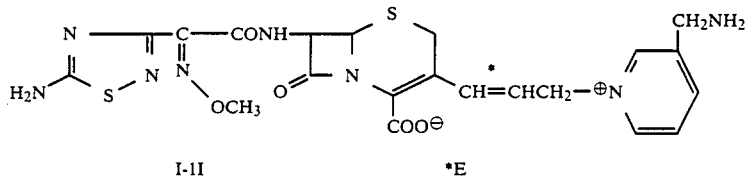

I-1I  *E

7-[2-(5-Amino-1,2,4-thiadiazol-3-yl)-2-methoxyiminoacetamido]-3-[3-(3-aminomethylpyridinio)-1-propen-1-yl]-3-cephem-4-carboxylate (I-1I)

A mixture of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (E, 716 mg, 1 mmole) and 3-(t-butyloxycarbonylaminomethyl)-pyridine (516 mg, 2 mmoles) in DMSO (2 ml) was stirred at ambient temperature for 30 minutes. The mixture was poured into ethyl acetate (200 ml), and the precipitate was collected by filtration, washed well with ethyl acetate and dried. A mixture of the quaternized salt (500 mg), sodium bisulfite (50 mg) in HCOOH (5 ml) was stirred at 40°–50° C. for 80 minutes and evaporated to dryness under reduced pressure. The residual solid was dissolved in water (40 ml), and the mixture was neutralized with $NaHCO_3$. Insoluble material was filtered off, and the filtrate was chromatographed on a reverse phase column (packing of PrepPAK-500/$C_{18}$ cartridge, 100 ml), eluting with water, 5%, 10%, 20% and 30% aqueous $CH_3OH$, successively. The fractions containing the desired compound were combined, evaporated and lyophilized to provide 10 mg (1.8%) of the title compound (I-1I) (E) as a tan powder.

IR: $\nu_{max}^{KBr}$ cm$^{-1}$ 3380 (br), 1760, 1650 (sh), 1620 (sh).

UV: $\lambda_{max}^{Phosphate\ buffer\ (pH\ 7)}$ nm ($E_{1\ cm}^{1\%}$) 235 (sh, 260), 286 (370).

NMR: $\delta_{ppm}^{D2O+NaHCO_3}$ 3.68 (2H, br, 2-H), 4.16 (3H, s, $OCH_3$), 6.98 (1H, d, J=16, 3-CH trans), 8.05 (1H, m, Py-$H_5$), 8.50 (1H, m, Py-$H_4$), 8.80 (2H, m, Py-$H_{2,6}$).

EXAMPLE 12 mer, 4.1 g, 5.7 mmoles) and isonicotinamide (1.4 g, 11 mmoles) in dry DMSO (6 ml) was stirred for 2 hours at room temperature while monitoring by TLC (silica gel plate, $CHCl_3:CH_3OH=3:1$). The reaction mixture was diluted with ethyl acetate (100 ml) to separate a yellow gum, which was treated with formic acid (40 ml) and sodium bisulfite (390 mg) at 45° C. for 30 minutes. The resulting solution was concentrated to dryness. The residue was dissolved in $H_2O$ (100 ml) and insolubles were removed by filtration. The combined filtrate and water wash was applied to the top of a column containing reverse phase packing (PrepPAK-500/$C_{18}$, 120 ml). The column was eluted with $H_2O$. The eluate was collected in 300 ml fractions and monitored by uv (254 nm) and HPLC (Lichrosorb RP-18, 4×300 mm, 0.01M ammonium phosphate buffer, pH 7.2 containing 20% $CH_3OH$). Fraction Nos. 4 and 5 were combined and concentrated to a small volume. Lyophilization gave 250 mg (8.1%) of the title compound I-1H, melting at >180° C. (dec.).

The spectra indicated that the product was identical to that obtained in Example 10.

Preparation of the hydrochloride—To a suspension of Compound I-1H (98 mg, 0.18 mmole) in $CH_3OH$ (1 ml) was added 10% HCl (0.1 ml), and the mixture was stirred for 5 minutes. To the resulting yellow solution was added acetone (100 ml) to give a precipitate, which was collected by filtration, washed with acetone (2×10 ml) and dried in vacuo to give the hydrochloride salt of I-1H as a colorless powder. Yield 88 mg (79%). Mp. >190° C. (dec.).

IR: $\nu_{max}^{KBr}$ cm$^{-1}$ 3300, 1770, 1680, 1620.

UV: $\lambda_{max}^{Phosphate\ buffer\ (pH\ 7)}$ nm ($E_{1\ cm}^{1\%}$) 227 (385), 286 (374).

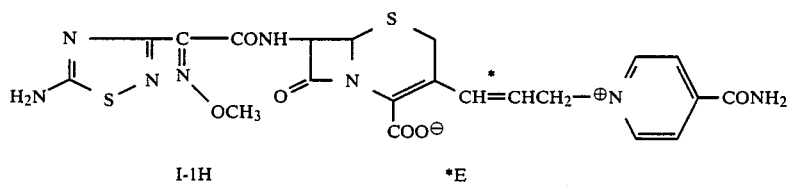

I-1H  *E

7-[2-(5-Amino-1,2,4-thiadiazol-3-yl)-2-methoxyiminoacetamido]-3-[3-(4-carbamoylpyridinio)-1-propen-1-yl]-3-cephem-4-carboxylate (I-1H)

A mixture of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (E iso- NMR: $\delta_{ppm}^{D2O}$ 2.32 (1H, s, acetone-H), 3.79 (2H, br-s, 2-H), 4.17 (3H, s, $OCH_3$), 5.34 (1H, d, J=4.5, 6-H), 5.49 (2H, d, J=7, CH=CH—$CH_2$), 5.93 (1H, d, J=4.5, 7-H), 6.28 (1H, d-t, J=16 & 7, 3-CH=CH), 7.15 (1H, d, J=16, 3-CH), 8.43 & 9.1 (each 2H, d, J=7, Py-H).

EXAMPLE 13

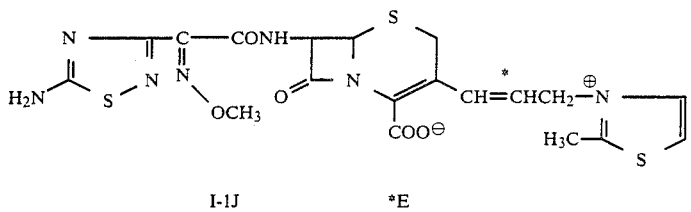

I-1J  *E

7-[2-(5-Amino-1,2,4-thiadiazol-3-yl)-2-methoxyiminoacetamido]-3-[3-(2-methylthiazolio)-1-propen-1-yl]-3-cephem-4-carboxylate (I-1J)

To a mixture of diphenylmethyl 7-[2-(5-amino-1,2,4-thiadiazol-3-yl)-2-methoxyiminoacetamido]-3-(3-iodo-1-propen-1-yl)-3-cephem-4-carboxylate (IX-1) (E, 714 mg, 1 mmole) and 2-methylthiazole [prepared according to the procedure of R. P. Kurkjy, E. V. Brown, J. Am. Chem. Soc., 74, 5778 (1952)] (198 mg, 2 mmoles) in dry $CH_2Cl_2$ (10 ml) was added $AgBF_4$ (90% pure, 217 mg, 1 mmole) at $-20°$ C. The mixture was stirred for 30 minutes at room temperature and filtered. The precipitate was extracted with 10% $CH_3OH$-$CHCl_3$ (3×20 ml). The combined extracts were washed with brine (2×5 ml), dried over $MgSO_4$ and evaporated to dryness to give a yellow residue, which was triturated with isopropyl ether and filtered to yield 350 mg of the quaternized product. A mixture of this solid, sodium bisulfite (35 mg) and formic acid (3.5 ml) was stirred at 40° C. for 30 minutes. The mixture was concentrated to remove the formic acid, and the residue was diluted with $H_2O$ (40 ml). Some insolubles were removed by filtration. The filtrate was placed on a reverse phase column (PrepPAK-500/$C_{18}$, 100 ml). The column was eluted with $H_2O$ (200 ml), 5% aqueous $CH_3OH$ (400 ml) and 10% aqueous $CH_3OH$ (300 ml), successively. The fractions containing the desired product were pooled on the basis of HPLC analysis (Lichrosorb RP-18, 4×300 mm, 0.01M ammonium phosphate buffer pH 7.2, containing 20% $CH_3OH$). The combined solution was concentrated to a small volume and lyophilized to give 40 mg (7.7%) of the title compound (I-1J) (E). Mp. >195° C. (dec.).

IR: $\nu_{max}^{KBr}$ cm$^{-1}$ 3300, 1760, 1660, 1600.

UV: $\lambda_{max}^{Phosphate\ buffer\ (pH\ 7)}$ nm ($E_{1\ cm}^{1\%}$) 238 (442), 292 (421).

NMR: $\delta_{ppm}^{D2O+DMSO-d6}$ 3.06 (3H, s, triazole-$CH_3$), 3.74 (2H, br-s, 2-H), 4.19 (3H, s, $OCH_3$), 5.92 (1H, d, J=4.5, 7-H), 6.1 (1H, m, 3-CH=CH), 6.8 (1H, d, J=16, 3-CH trans), 8.04 & 8.23 (each 1H, d, J=4, thiazole-H).

EXAMPLE 14

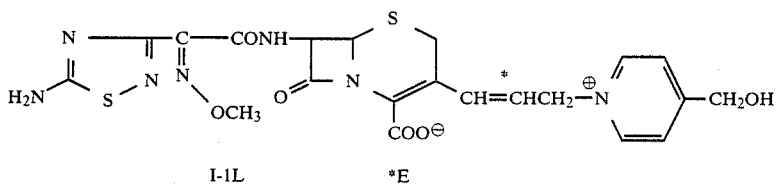

I-1L  *E

7-[2-(5-Amino-1,2,4-thiadiazol-3-yl)-2-methoxyiminoacetamido]-3-[3-(4-hydroxymethylpyridinio)-1-propen-1-yl]-3-cephem-4-carboxylate (I-1L)

A mixture of diphenyl 7-[2-(5-amino-1,2,4-thiadiazol-3-yl)-2-methoxyiminoacetamido]-3-(3-iodo-1-propen-1-yl)-3-cephem-4-carboxylate (IX-1) (E isomer, 1.07 g, 1.5 mmole), 4-hydroxymethylpyridine (818 mg, 7.5 mmole) in $CH_3CN$ (4.5 ml) and $CH_3OH$ (3 ml) was stirred at room temperature under $N_2$ atmosphere for one hour. After removal of the solvents by evaporation, the residual oil was triturated with isopropyl ether, collected by filtration, and washed with a mixture of isopropyl ether and methanol (3:1, 10 ml) to give 1.28 g of the quaternized cephem ester as a yellow powder. A solution of the quaternized ester (1.25 g) and sodium bisulfite (600 mg) in 85% HCOOH (10 ml) was stirred at room temperature under $N_2$ atmosphere for one hour. After the addition of 85% HCOOH (5 ml), the mixture was stirred under the same conditions for an additional hour. Toluene was added and the reaction mixture was evaporated azeotropically under reduced pressure. The residue was triturated with acetone to yield 1.17 g of the crude formate of the title compound. A suspension of this compound (1.15 g) in water (100 ml) was filtered to remove insolubles, which were washed with water (10 ml×2). The filtrate and the washes were combined and subjected to reverse phase column chromatography. The column, which was packed with the packing taken out of a prepPAK-500/$C_{18}$ cartridge column (Waters) 60 ml), was developed with water, 5% methanol and 10% methanol, successively. The fractions containing the desired compound were combined, concentrated under reduced pressure, and precipitated by the addition of acetone to give 100 mg of the title compound (I-1L) as a pale yellow powder. To a suspension of the powder (90 mg) in methanol (9 ml) was added 1M HCl in $CH_3OH$ (0.5 ml) and the mixture was stirred at room temperature and concentrated in vacuo. To the concentrate was added isopropanol to precipitate 77 mg of the hydrochloride of the title compound. Pale yellow powder. M.p. >190° C. (dec.).

IR: $\nu_{max}^{KBr}$ cm$^{-1}$, 1775, 1670, 1635, 1530.

UV: $\lambda_{max}^{Phosphate\ buffer\ (pH\ 7)}$ nm ($\epsilon$), 230 (22600), 264 (sh, 16300).

NMR: $\delta_{ppm}^{D2O}$ 3.83 (2H, br. 2-CH), 4.17 (3H, s, $OCH_3$), 5.06 (2H, s,

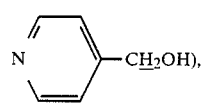

$CH_2OH$), 5.36 (1H, d, J=4.5 Hz, 6-H), 5.41 (2H, d, J=7 Hz, CH=CH—CH₂), 5.94 (1H, d, J=4.5 Hz, 7-H), 6.36 (1H, d-t, J=16 and 7 Hz, CH=CHCH₂), 7.13 (1H, d, J=16 Hz, CH=CH—CH₂), 8.08 and 8.83 (each 2H, d, J=7 Hz, Py-H).

EXAMPLE 15

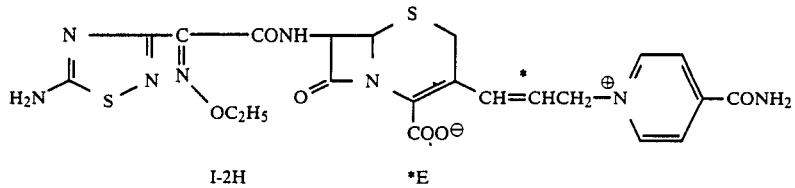

I-2H      *E

7-[2-(5-Amino-1,2,4-thiadiazol-3-yl)-2-ethoxyiminoacetamido]-3-[3-(4-carbamoylpyridinio)-1-propen-1-yl]-3-cephem-4-carboxylate (I-2H)

To a solution of 200 mg of 7-amino-3-[3-(4-carbamoylpyridinio)-1-propen-1-yl]-3-cephem-4-carboxylate hydrochloride (E isomer) in 5 ml of 50% aqueous acetone was added portionwise 190 mg of 2-ethoxyimino-2-(5-amino-1,2,4-thiadiazol-3-yl)acetyl chloride hydrochloride [prepared according to the procedure described in published Japan patent application (Kokai) No. 57-24389 (2/8/82)], and the mixture was adjusted to pH 6.5-7.0 with 2N Na₂CO₃ (about 1 ml). The reaction mixture was stirred at 10° C. for an hour, acidified to pH 2 with 1N HCl and evaporated in vacuo. The residue was filtered and the filtrate was chromatographed on a column of HP-20, which was eluted with 500 ml of water and 25% aqueous isopropanol, successively. Fractions containing the desired product were combined and evaporated under reduced pressure. The oily residue was treated with isopropanol (20 ml) to give 263 mg (93%) of the title compound (I-2H). M.p. 170° C. (dec.).

To a stirred suspension of 225 mg (0.40 mmole) of the above zwitterion in 10 ml of methanol was added 1 ml of 1N HCl in CH₃OH and the mixture was stirred at room temperature for 30 minutes. The solution was filtered and concentrated under reduced pressure. To the residue was added 15 ml of isopropyl alcohol, and the resulting precipitate was collected by filtration and dried in vacuo to give the title compound as its hydrochloride. Yield 146 mg (57%). M.p. 160° C. (dec.). Estimated purity 65%.

IR: $\nu_{max}^{KBr}$ cm⁻¹, 3300, 1780, 1680, 1620.

UV: $\lambda_{max}^{Phosphate\ buffer\ (pH\ 7)}$ nm (ε), 227 (22300), 288 (22800).

NMR: $\delta_{ppm}^{D_2O}$ 1.44 (3H, t, J=7 Hz, OCH₂—CH₃), 3.74 (2H, br. s, 2-H) 4.45 (2H, q, J=7 Hz, OCH₂—CH₃), 5.36 (1H, d, J=4.5 Hz, 6-H), 5.46 (2H, d, J=7 Hz, 3-CH=CH—CH₂), 5.92 (1H, d, J=4.5 Hz, 7-H), 6.20 (1H, m, 3-CH=CH), 7.04 (1H, d, J=16 Hz, 3-CH=CH), 8.43 (2H, d, J=7 Hz), Py-H_A), 9.10 (2H, d, J=7 Hz, Py-H_B).

EXAMPLE 16

7-[2-(5-Amino-1,2,4-thiadiazol-3-yl)-2-methoxyiminoacetamido]-3-[3-(4-carbamoylpyridinio)-1-propen-1-yl]-3-cephem-4-carboxylate (I-1H) (E isomer)

This Example shows the preparation of Compound I-1H via the last few steps of Reaction Scheme 1a or 1b, wherein the intermediate benzhydryl 7-[2-(5-amino-1,2,4-thiadiazol-3-yl)-2-methoxyiminoacetamido]-3-[3-(4-carbamoylpyridinio)-1-propen-1-yl]-3-cephem-4-carboxylate formate (XXVII-1H) is isolated.

A. Benzhydryl 7-[2-(5-Amino-1,2,4-thiadiazol-3-yl)-2-methoxyiminoacetamido]-3-[3-(4-carbamoyl-1-pyridinio)-1-propen-1-yl]-3-cephem-4-carboxylate Formate (E isomer) (XXVII-1H)

A solution of XII-1H (Y⊖=I⊖, E isomer) (34 g, 75% pure) in a mixture of acetone and CH₃OH (1/1, 200 ml) was placed on a column of Amberlite IRA-410 (formate form 340 ml). The column was eluted with the same solvent system. The first fraction (1 L) was evaporated to about 100 ml of the volume and the brown residue was triturated with isopropyl ether (400 ml). The resulting powder was collected by filtration and dried under vacuum to afford 29 g (75% pure by HPLC) of the title compound XXVII-1H (E isomer) as a brown powder melting at >150° C. (dec.).

IR: $\nu_{max}^{KBr}$ cm⁻¹ 3300, 1780, 1680, 1630, 1600.

UV: $\lambda_{max}^{EtOH}$ nm (E₁ cm 1%) 282 (186).

NMR: $\delta_{ppm}^{acetone\ -d6/CH_3OH-d_4(1/1)}$ 4.0 (3H, s, OCH₃), 5.26, (1H, d, J=4.5 Hz, 6-H), 5.43 (2H, d, J=7 Hz, CH₂N⁺), 5.99 (1H, d, J=4.5 Hz, 7-H), 6.5 (1H, m, 3-CH=CH), 6.92 (1H, s, CHPh₂), 7.1 (1H, d, J=16 Hz, 3-CH), 7.35 (10H, m, Ph-H), 8.36 (1H, s, HCOO), 8.46 & 9.12 (2H each, d, J=8 Hz, Py-H).

B. 7-[2-(5-Amino-1,2,4-thiadiazol-3-yl)-2-methoxyiminoacetamido]-3-[3-(4-carbamoyl-1-pyridinio)-1-propen-1-yl]-3-cephem-4-carboxylate (I-1H) (E isomer)

A mixture of XXVII-1H (E isomer) from Step A (29 g, 75% pure) and 85% formic acid (290 ml) was stirred for 2 hours at room temperature. Evaporation of the mixture gave a brown oil which was triturated with acetone (500 ml). The powder was collected by filtration, washed with acetone (2×100 ml) and dried in vacuo to give 24 g (50% pure by HPLC) of the crude title compound. The brown solid was treated twice with 2N HCl (1 L and 0.5 L). The aqueous extracts were combined and placed on a column packed with Diaion HP-20 (1.5 L). The column was washed with water (8 L) and eluted with 30% CH₃OH (5 L). The fraction containing the desired product was evaporated to about 30 ml. The concentrate was treated with acetone (200 ml) to give a precipitate, which was collected by filtration and dried in vacuo to give 10.1 g (85% pure) of the title compound (zwitterion form) as a yellow powder. To a suspension of this product in CH₃OH (100 ml) was added N HCl in CH₃OH (55 ml) at room temperature and the mixture was stirred for 30 minutes. The resulting clear solution was filtered to remove insolubles, concentrated to about 50 ml of the volume and precipitated with isopropanol (200 ml). The resulting powder was collected, washed with isopropanol (50 ml) and dried in vacuo to give 10.5 g (85% pure) of the title compound I-1H (E isomer) (HCl salt), melting at >180° C. (dec.). Pale yellow powder.

EXAMPLE 17

7-[2-(5-Amino-1,2,4-thiadiazol-3-yl)-2-methoxyiminoacetamido]-3-[3-(4-carbamoylpyridinio)-1-propen-1-yl]-3-cephem-4-carboxylate (I-1H) (E isomer)

This example shows the preparation of Compound I-1H via the last few steps of Reaction Scheme 1a or 1b, wherein intermediate XXVII-1H (the formate) is not isolated.

A solution of IX-1 (E isomer) (27.6 g, 38.5 mmole) and isonicotinamide (22.8 g, 187 mmole) in a mixture of $CH_3CN$ (120 ml) and $CH_3OH$ (100 ml) was stirred at room temperature for 1 hour under a nitrogen atmosphere. After evaporation of the organic solvents, the oily residue was triturated with isopropyl ether to give 50.5 g of a mixture of the quaternized salt and isonicotinamide. A solution of the mixture (50.3 g) and sodium bisulfite (16 g) in 85% HCOOH (160 ml) was stirred at room temperature for 40 minutes and subsequently at 40° C. for 1 hour under $N_2$. The mixture was evaporated in vacuo. The residual oil was mixed with toluene (50 ml), evaporated azeotropically and triturated with acetone (400 ml) to give 27.8 g of the crude title compound. This material was treated twice with 2N HCl (1 L and 0.5 L). The acid extracts were combined and placed on a column of HP-20 resin (1.5 L). The column was eluted with water (9 L) and 30% methanol (10 L). The fractions containing the desired compound were combined and concentrated to give a yellow oil, which was triturated with acetone (300 ml) to yield 9.35 g of the zwitterion form of the title compound.

To a suspension of the product (9.3 g) in $CH_3OH$ (180 ml) was added 1N HCl in $CH_3OH$ (55 ml) to obtain a clear solution. The solution was concentrated to about 100 ml and diluted with isopropanol to precipitate 9.50 g (purity 75%) of the title compound I-1H (E isomer) as its hydrochloride. Pale yellow amorphous powder. M.p. >195° C. (dec.).

EXAMPLE 18

7-[2-(5-Amino-1,2,4-thiadiazol-3-yl)-2-methoxyiminoacetamido]-3-[3-(4-carbamoylpyridinio)-1-propen-1-yl]-3-cephem-4-carboxylate (I-1H) (E isomer)

This example shows the preparation of Compound I-1H via the last step (7-N-acylation) of Reaction Scheme 1c.

To an ice-chilled suspension of the 7-amino-cephem hydrochloride XXII-H (E isomer) (5.0 g, 12.6 mmole) in 50% aqueous acetone (100 ml) was added sodium bicarbonate in small portions. The pH of the mixture was monitored by a pH meter throughout the reaction. To the cold neutralized solution (pH about 7) was added 2-(5-amino-1,2,4-thiadiazol-3-yl)-2-methoxyiminoacetyl chloride hydrochloride (4.02 g, 15.6 mmole) in small portions over a period of an hour, and the pH of the reaction mixture was maintained in the range of 6.8–7.5 by occasional additions of sodium bicarbonate. The reaction was also monitored by tlc. After all of Compound XXII-H had been consumed, the mixture was acidified to pH 3 by the addition of 2N hydrochloric acid. The mixture was filtered, and the filtrate was concentrated under reduced pressure. The residue was diluted with acetone (400 ml) to separate the precipitate, which was collected by filtration to afford 9.59 g of the crude title compound as a light yellow powder. Estimated purity 40% by HPLC. A suspension of the crude product (9.5 g) in 2N hydrochloric acid (150 ml) was filtered, and the filtrate was adsorbed on a column of HP-20 resin (500 ml). After washing with water (1.5 L), the column was eluted with 25% aqueous isopropyl alcohol and the eluate was collected in 100-ml fractions. The desired fractions were pooled, acidified with 2N hydrochloric acid (10 ml) and concentrated. The residual oil was triturated with isopropyl alcohol (200 ml), and the precipitate was collected by filtration. After drying over phosphorus pentoxide, 5.18 g of the title compound I-1H (E isomer) hydrochloride was obtained as a yellow amorphous powder. M.p. >190° C. (dec.). Estimated purity 75%.

EXAMPLE 19

Purification and crystallization of Compound I-1H (E isomer)

Compound I-1H hydrochloride obtained in Example 16 was a pale yellow amorphous powder of 85% purity.

Procedure 1

Six grams of the 85% purity hydrochloride was dissolved in 20 ml of $H_2O$ and filtered through a celite pad. The ambercolored filtrate (pH 2) was passed through a reverse phase column (the packing of prepPAK-500/$C_{18}$ cartridge, Waters; 120 ml), which was eluted with water. The eluate was collected in 120-ml fractions with monitoring by HPLC*. Fraction No. 3 through fraction No. 5 were combined and concentrated to about 10 ml, and precipitated by acetone (100 ml) to give 3.3 g of the zwitterion form of I-1H (pale yellow amorphous powder; estimated purity 95%).

*Column, Lichrosorb RP-18, 4×300 mm: Mobile phase, 0.01M phosphate buffer (pH 7.2)/$CH_3OH$=85/15: Detection, uv (254 nm).

To a suspension of the 95% purity powder (3.2 g) in $CH_3OH$ (32 ml) was added N HCl in $CH_3OH$ (18 ml), and the mixture was stirred at room temperature until a clear solution was obtained. The solution was filtered and the filtrate was concentrated to about 10 ml. To the concentrate was added isopropanol (100 ml) to separate a pale yellow precipitate, which was collected by filtration, washed with isopropanol (5 ml) and dried to yield 2.6 g of the HCl salt (amorphous powder; estimated purity 95%).

A solution of the 95% purity hydrochloride (1 g) in water (4 ml) was adjusted to pH 6.5 with $NaHCO_3$ (200 mg) and stirred for 30 minutes. The crystals which separated during stirring were collected by filtration, washed with water (2×5 ml) and dried in vacuo to give 710 mg of I-1H (zwitterion form) as pale yellow prisms. M.p. >185° C. (dec.). Microanalysis showed it to be the trihydrate.

IR: $\nu_{max}^{KBr}$ cm$^{-1}$ 1780, 1695, 1660, 1630, 1610.

UV: $\lambda_{max}^{Phosphate\ buffer\ (pH7)}$ nm ($\epsilon$) 227 (22000), 290 (23000).

NMR: $\delta_{ppm}^{DMSO-d6+D2O}$ 3.45 (2H, br, s, 2-H), 3.9 (3H, s, OC$\underline{H}_3$), 4.99 (1H, d, J=4.5 Hz, 6-H), 5.16 (2H, d, J=7 Hz, C$\underline{H}_2$N$^+$), 5.61 (1H, d, J=4.5 Hz, 7-H), 5.8 (1H, d-t, J=16 & 7 Hz, 3-CH=C$\underline{H}$), 6.93 (1H, d, J=16 Hz, 3-C$\underline{H}$), 8.18 & 8.89 (each 2H, d, J=7 Hz, Py-H).

Anal. Calc'd for $C_{21}H_{20}N_8O_6S_2\cdot 3H_2O$: C, 42.14; H, 4.38; N, 18.72; S, 10.71. Found: C, 42.41; H, 4.35; N, 18.86; S, 11.00.

Procedure 2

Once crystalline I-1H had been obtained from Procedure 1, it was possible to obtain the crystalline zwitterion form of I-1H directly from the crude I-1H hydrochloride by seeding with a few crystals of the pure I-1H.

A solution of the 85% pure hydrochloride (250 mg) in water (1 ml) was treated with charcoal. The solution was adjusted to pH 6.5 with NaHCO$_3$ (60 mg) and decolorized with charcoal. The filtrate was seeded with a few pieces of the crystals obtained from Procedure 1 and stirred overnight at room temperature. The separated crystals were collected by filtration, washed with water (2×2 ml) and dried under reduced pressure to give 170 mg (80% recovery) of pale yellow prisms of I-1H (zwitterion form), melting at >185° C. (dec.), which was identical with that obtained by Procedure 1, (as shown by IR, UV, NMR).

The crystalline zwitterion form of Compound I-1H was slightly soluble in water (6 mg/ml) in saline at 23° C.).

EXAMPLE 20

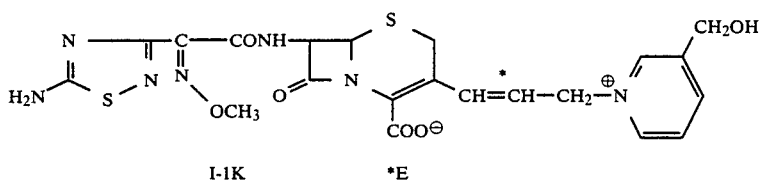

I-1K  *E

7-[2-(5-Amino-1,2,4-thiadiazol-3-yl)-2-methoxyiminoactamido]-3-[3-(3-hydroxymethylpyridinio)-1-propenyl]-3-cephem-4-carboxylate (I-1K) (E isomer)

A. Diphenylmethyl 7-[2-(5-Amino-1,2,4-thiadiazol-3-yl)-2-methoxyiminoacetamido]-3-[3-(3-hydroxymethylpyridinio)-1-propenyl]-3-cephem-4-carboxylate iodide (E-isomer) (XII-1K)

To a solution of IX-1 (E-isomer, 1.79, g, 2.5 mmoles) in 2.5 ml of CH$_3$OH and 7.5 ml of CH$_3$OH was added 3-hydroxymethylpyridine (545 mg, 5 mmoles), and the mixture was stirred at room temperature for 3 hours. The reaction mixture was poured into ethyl acetate (100 ml) with vigorous stirring. The resulting precipitate was collected by filtration, washed with a small volume of ethyl acetate and dried to give 2.06 g (100%) of the title compound XII-1K as a tan powder. Mp. 170°–180° C. (dec.).

IR: $\lambda_{max}$ (KBr) in cm$^{-1}$ 1780, 1725, 1675, 1615, 1530, 1385, 1225, 1040, 750, 700.

UV: $\lambda_{max}$ (C$_2$H$_5$OH) in nm (E$_{1\ cm}$$^{1\%}$) 290 (196).

NMR: δ (DMSO+D$_2$O) in ppm 3.7 (2H, br.s, 2-H), 3.91 (3H, s, OCH$_3$), 4.70 (2H, s, Py-CH$_2$-OH), 5.28 (2H, m, CH$_2$-N$^+$), 5.23 (1H, d, J=5 Hz, 6-H), 5.90 (1H, d, J=5 Hz, 7-H), 6.34 (1H, m, 3-CH=CH), 6.86 (1H, d, J=16 Hz, 3-CH), 6.89 (1H, s, CHPh$_2$), 7.35 (10H, m, Ph-H), 7.9–8.9 (4H, m, Py-H).

B. 7-[2-(5-Amino-1,2,4-thiadiazol-3-yl)-2-methoxyiminoacetamido]-3-[3-(3-hydroxymethylpyridinio)-1-propenyl]-3-cephem-4-carboxylate (I-1K) (E isomer)

A mixture of XII-1K (E isomer, 2.0 g, 2.4 mmoles) and sodium bisulfite (1 g) in 85% HCOOH (10 ml) was stirred for 2 hours at room temperature. The reaction mixture was concentrated to ca. 5 ml under reduced pressure. The oily residue was poured into acetone (100 ml) with vigorous stirring. The precipitate was collected by filtration, washed with a small amount of acetone and dried to give 1.1 g of a tan powder, which was purified by column chromatography [using the packing of a PrepPAK-500/C$_{18}$ cartridge (Waters)] to give 283 mg (22%) of I-1K as an amorphous powder. The powder was crystallized from 4N H$_2$SO$_4$ and acetone to give 144 mg of the title compound I-1K as colorless needles. Mp. 185°–188° C. (dec.).

IR: $\lambda_{max}$ (KBr) in cm$^{-1}$ 1775, 1680sh, 1660, 1630, 1225, 1045, 850.

UV: $\lambda_{max}$ (Phosphate buffer, pH 7) in nm (E$_{1\ cm}$$^{1\%}$) 236.5 (283), 275 sh (280), 292.5 (330).

NMR: δ (D$_2$O) in ppm 3.75 (2H, s, 2-H), 4.18 (3H, s, OCH$_3$), 4.97 (2H, s, Py-CH$_2$OH), 5.35 (1H, d, J=4 Hz, 6-H), 5.43 (2H, d, J=6.5 Hz, CH$_2$-N$^+$), 5.92 (1H, d, J=4 Hz, 7-H), 6.18 (1H, d-t, J=16 Hz, J=6.5 Hz, 3-CH=CH—), 6.97 (1H, d, J=16 Hz, 3-CH), 8.13 (1H, d-d, J=8 Hz, J=6 Hz, Py-H), 8.60 (1H, d, J=8 Hz, Py-H), 8.84 (1H, d, J=6 Hz, Py-H), 8.90 (1H, s, Py-H).

EXAMPLE 21

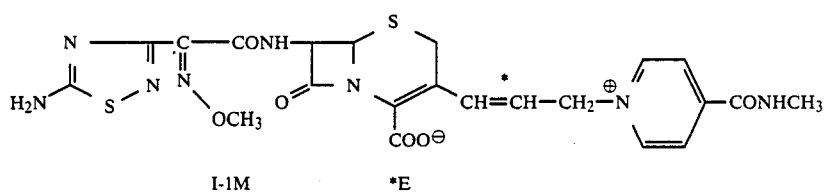

I-1M  *E

7-[2-(5-Amino-1,2,4-thiadiazol-3-yl)-2-(Z)-methoxyiminoacetamido]-3-[3-(4-N-methylcarbamoylpyridinio)-1-propenyl]-3-cephem-4-carboxylate (I-1M) (E isomer)

A mixture of diphenylmethyl 7-[2-(5-amino-1,2,4-thiadiazol-3-yl)-2-methoxyaminoacetamido]-3-(3-iodo-1-propenyl)-3-cephem-4-carboxylate (IX-1) (E isomer, 450 mg, 0.62 mmole) and 4-N-methylcarbamoylpyridine [prepared according to the procedure of M. Samejima, Yakugaku Zasshi, 80, 1706 (1960)] (215 mg, 1.58 mmoles) in acetonitrile (2 ml) was stirred under nitrogen atmosphere for 5 hours at room temperature. The mixture was evaporated under reduced pressure and the residue was triturated with ether to give 530 mg of the quaternary salt. A mixture of the solid and sodium bisulfite (150 mg) in 85% formic acid (2 ml) was stirred for 4 hours and then heated at 40° C. for 30 minutes. The mixture was evaporated under reduced pressure. The residue was triturated with acetone and the crude product was collected by filtration. The crude product was chromatographed on a column of HP-20 (1.5×18 cm) and the column was eluted with water and 30% aqueous methanol. The methanolic eluate was evaporated under reduced pressure and the residue was freeze-dried to give 140 mg of an amorphous powder, which was further purified by HPLC (Column: Lichrosorb RP-18, Solvent: 15% CH$_3$OH) and the eluate of HPLC was freeze-dried to give 60 mg (18%) of the title product I-1M. Mp. 180°–183° C. (dec.). Estimated purity: 80%.

IR: $\nu_{max}$ (KBr) in cm$^{-1}$ 1760, 1660, 1600.

UV: $\lambda_{max}$ (Phosphate buffer, pH 7) in nm ($\epsilon$) 230 (22100), 286 (22100).

NMR: δ (D$_2$O) in ppm 3.08 (3H, s, CONHCH$_3$), 3.72 (2H, s, 2-H), 4.16 (3H, s, OCH$_3$), 5.35 (1H, d, J=4.5 Hz, 6-H), 5.95 (1H, d, J=4.5 Hz, 7-H), 7.00 (1H, d, J=16 Hz, 3-CH), 8.35 (2H, d, J=6 Hz, pyridine-H), 9.05 (2H, d, J=16 Hz, pyridine-H).

precipitate was isolated by filtration to afford 421 mg of a yellow powder. This crude powder (400 mg) was suspended in water (2 ml) and to the suspension was added sodium bicarbonate. The resulting dark solution was adsorbed on a column of the packing (50 ml) of a PrepPAK/C$_{18}$ cartridge (Water's System 500), and the column was eluted by water (200 ml). The eluent was fractionated into 10 fractions (20 ml of each), and the desired fractions (Fractions Nos. 4–7) were combined, acidified to pH 3 with 2N hydrochloric acid, and concentrated. The residue was triturated with acetone (30 ml) and the precipitate was collected by filtration to give 201 mg (37%) of the title compound I-1N as a yellow powder. E/Z=7/1; 80% pure. Mp. >189° C. (dec.).

IR: $\nu_{max}$ (KBr) in cm$^{-1}$ 1770, 1665, 1600.

UV: $\lambda_{max}$ (Phosphate buffer, pH 7) in nm ($\epsilon$) 227 (22500), 290 (22100).

NMR: δ (D$_2$O+NaHCO$_3$) in ppm 3.7 (2H, br.s), 4.15 (3H, s), 5.32 (1H, d, J=4 Hz), 5.39 (2H, d, J=6 Hz), 6.14 (1H, d-t, J=15.5 and 6 Hz), 7.03 (1H, d, J=15.5 Hz), 8.31 (2H, d, J=7 Hz), 8.94 (2H, d, J=7 Hz).

EXAMPLE 23

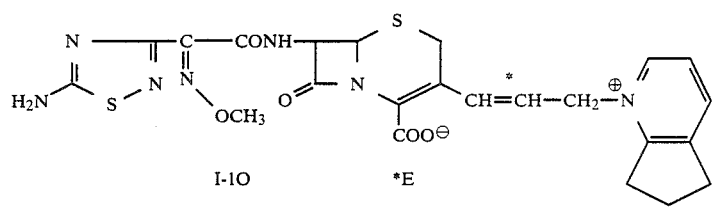

I-10     *E

7-[2-(5-Amino-1,2,4-thiadiazol-3-yl)-2-(Z)-methox-

EXAMPLE 22

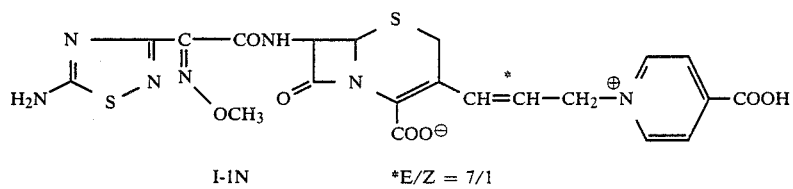

I-1N     *E/Z = 7/1

7-[2-(5-Amino-1,2,4-thiadiazol-3-yl)-2-methoxyiminoacetamido]-3-[3-(4-carboxypyridinio)-1-propenyl]-3-cephem-4-carboxylate (I-1N)

To a stirred suspension of isonicotinic acid (340 mg, 2.8 mmoles) in dry DMF (3.5 ml) was added N,O-bis(-trimethylsilyl)acetamide (0.7 ml, 2.8 mmoles) under nitrogen atmosphere. To the resulting clear solution was added diphenylmethyl 7-[2-(5-amino-1,2,4-thiadiazol-3-yl)-2-methoxyiminoacetamido]-3-(3-iodo-1-propenyl)-3-cephem-4-carboxylate (IX-1) (E isomer, 720 mg, 1 mmole) in one portion, and the red solution was stirred for 1.5 hours at room temperature. The reaction mixture was added dropwise to a stirred saturated sodium chloride solution (50 ml) containing sodium thiosulfate (150 mg). The yellow precipitate was collected by filtration, washed with water, and dried to obtain 722 mg of a pale yellow powder. The powder (700 mg) and sodium bisulfite (70 mg) were dissolved in 85% formic acid (5 ml), and the solution was allowed to stand at room temperature for 1.5 hours. The mixture was suspended in toluene (50 ml) and concentrated. The residue was triturated with acetone (70 ml), and the yiminoacetamido]-3-[3-(2,3-cyclopentenopyridinio)-1-propenyl]-3-cephem-4-carboxylate (I-10) (E isomer)

A mixture of diphenylmethyl 7-[2-(5-amino-1,2,4-thiadiazol-3-yl)-2-methoxyiminoacetamido]-3-(3-iodo-1-propenyl)-3-cephem-4-carboxylate (IX-1) (E isomer, 450 mg, 0.62 mmole) and 2,3-cyclopentenopyridine (217 mg, 1.83 mmole) in acetonitrile (2 ml) was stirred under nitrogen atmosphere for 4 hours at room temperature. After evaporation under reduced pressure, the mixture was triturated with ether to give 560 mg of the quaternary salt. A mixture of the solid and 85% formic acid (2 ml) was stirred under nitrogen for 3 hours at room temperature and then heated at 40° C. for 30 minutes. The mixture was evaporated under reduced pressure and trituration of the residue afforded 391 mg of the crude product, which was purified by chromatography on a column of HP-20 (1.5×18 cm). The column was eluted with water and 30% aqueous methanol. Evaporation of the methanolic eluate under reduced pressure, followed by freeze-drying afforded 160 mg of an amorphous powder, which was further purified by HPLC (Column: Lichrosorb, Solvent: 10% CH$_3$OH). The eluate of HPLC was freeze-dried to give 50 mg (15%) of the title product I-10. Mp. >190° C. (dec.). Estimated purity: 75%.

IR: $\nu_{max}$ (KBr) in cm$^{-1}$ 1765, 1670, 1600.

UV: $\lambda_{max}$ (Phosphate buffer, pH 7) in nm ($\epsilon$) 235 (20000), 283 (25000).

NMR: δ (D$_2$O+NaHCO$_3$) in ppm 2.2-2.6 (2H, m, —CH$_2$—), 3.1-3.6 (4H, m, —CH$_2$—), 3.72 (2H, s, 2-H), 4.17 (3H, OCH$_3$), 5.33 (1H, d, J=4.5 Hz, 6-H), 5.90 (1H, d, J=4.5 Hz, 7-H), 6.75 (1H, d, J=16 Hz, 3-CH), 7.65-8.2 (3H, m, pyridine-H).

EXAMPLE 24

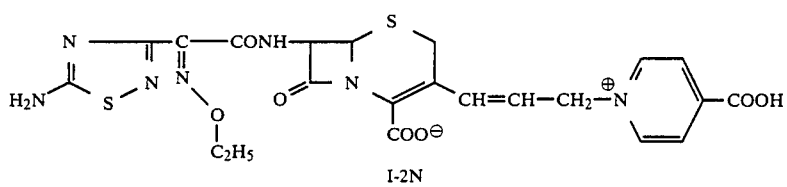

7-[2-(5-Amino-1,2,4-thiadiazol-3-yl)-2-(Z)-ethoxyiminoacetamido]-3-[3-(4-carboxypyridinio)-1-propenyl]-3-cephem-4-carboxylate (I-2N, E isomer) and 7-[2-(5-Amino-1,2,4-thiadiazol-3-yl)-2-(Z)-ethoxyiminoacetamido]-3-[3-(4-carboxypyridinio)-1-propenyl]-3-cephem-4-carboxylate (I-2N, Z isomer)

To a chilled mixture of BSA (1.0 ml, 4.12 mmoles) and isonicotinic acid (506 mg, 4.12 mmoles) was added IX-2 (from Preparation No. 21) (1.0 g, 1.37 mmoles), and the mixture was stirred under nitrogen at room temperature for 2 hours. The mixture was poured into 10% Na$_2$S$_2$O$_3$ (20 ml) to precipitate 1.3 g of the quaternary salt, which was collected by filtration, washed with water and dried. A mixture of the solid and sodium bisulfite (0.3 g) in formic acid (98%, 5 ml) was heated at 40° C. for 1 hour and evaporated under reduced pressure. The residue was triturated with acetone and filtered to give 900 mg of the crude product (E-propenyl isomer:Z-propenyl isomer=2:1). Separation of the isomers was carried out by HPLC (Column: Lichrosorb, Solvent: 15% CH$_3$OH). The faster moving fractions of HPLC were collected, evaporated under reduced pressure and freeze-dried to give the E-propenyl isomer of I-2N (44 mg, yield 6%). The slower moving fractions gave the Z-propenyl isomer of I-2N (32 mg, yield 4%) in a similar procedure.

I-2N, E isomer

Mp.: >200° C. (dec.).

IR: $\nu_{max}$ (KBr) in cm$^{-1}$ 1765, 1660, 1620, 1380.

UV: $\lambda_{max}$ (Water) in nm ($\epsilon$) 228 (22200), 291 (23600).

NMR: δ (D$_2$O) in ppm 1.45 (3H, t, J=6 Hz, CH$_2$CH$_3$), 3.72 (2H, s, 2-H), 4.45 (2H, q, CH$_2$CH$_3$), 5.40 (1H, d, J=4 Hz, 6-H), 5.90 (1H, d, J=4 Hz, 7-H), 7.05 (1H, d, J=15 Hz, 3-CH), 8.30 (2H, d, J=6 Hz, Py-H), 8.95 (2H, d, J=6 Hz, Py-H).

I-2N, Z isomer

Mp.: >200° C. (dec.).

IR: $\nu_{max}$ (KBr) in cm$^{-1}$ 1760, 1660 (sh), 1620, 1370.

UV: $\lambda_{max}$ (Phosphate buffer, pH 7) in nm ($\epsilon$) 225 (22400), 275 (sh, 16000).

NMR: δ (D$_2$O) in ppm 1.45 (3H, t, J=7 Hz, CH$_2$CH$_3$), 3.50 (1H, d, J=17 Hz, 2-H), 3.75 (1H, d, J=17 Hz, 2-H), 5.38 (1H, d, J=4 Hz, 6-H), 5.95 (1H, d, J=4 Hz, 7-H), 6.62 (1H, d, J=11 Hz, 3-CH), 8.35 (2H, d, J=6 Hz, Py-H), 8.92 (2H, d, J=6 Hz, Py-H).

EXAMPLE 25

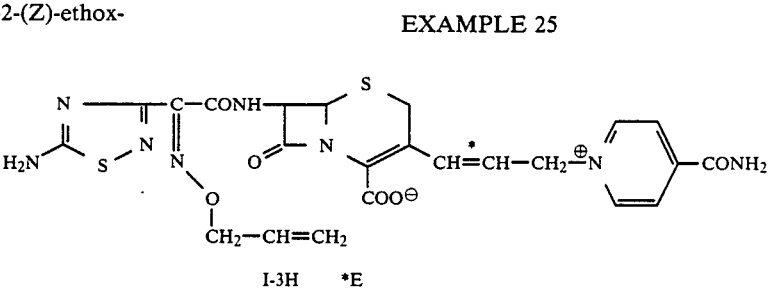

7-[2-(Amino-1,2,4-thiadiazol-3-yl)-2-(propen-3-yloxyimino)acetamido]-3-[3-(4-carbamoylpyridinio)-1-propenyl]-3-cephem-4-carboxylate (I-3H) (E isomer)

To a solution of 35 mg (0.08 mole) of 7-amino-3-[3-(4-carbamoylpyridinio)-1-(E)-propenyl]-3-cephem-4-carboxylate hydrochloride in 2 ml of 50% aqueous acetone was added 52 mg of 2-[5-amino-1,2,4-thiadiazol-3-yl)]-2-(propen-3-yloxyimino)acetyl chloride hydrochloride (from Preparation No. 25) and the mixture was adjusted to pH 6.5-7.0 with 2N Na$_2$CO$_3$. The mixture was stirred at room temperature for 1 hour, acidified to pH 2 with 1N HCl and concentrated under reduced pressure. The residue was chromatographed on a column of HP-20 resin which was eluted with 300 ml of water and 30% CH$_3$OH—H$_2$O. Fractions containing the product were combined and evaporated under reduced pressure. The residue, 73 mg, was purified by a column of reverse phase carrier which was taken out of a PrepPAK-500/C$_{18}$ cartridge (Waters, 30 ml). The column was eluted with water, 5% CH$_3$OH, 10% CH$_3$OH and 20% CH$_3$OH, successively. Fractions containing the product were combined and lyophilized to afford 26 mg (62%) of the title product I-3H. Mp. 160° C. (dec.).

IR: $\nu_{max}$ (KBr) in cm$^{-1}$ 3400, 1765, 1680, 1605, 1400.

UV: $\lambda_{max}$ (Phosphate buffer, pH 7 ) in nm ($\epsilon$) 226 (24600), 288 (22800).

NMR: δ (D$_2$O) in ppm 3.75 (2H, s, 2-H), 5.41 (1H, d, J=5 Hz, 6-H), 5.50 (4H, m, CH$_2$N$^+$ & CH=CH$_2$), 5.98 (1H, d, J=5 Hz, 7-H), 6.20 (1H, m, 3-CH=CH), 7.09 (1H, d, J=17 Hz, 3-CH), 8.50 (2H, d, J=7 Hz, Py-H), 9.16 (2H, d, J=7 Hz, Py-H).

EXAMPLE 26

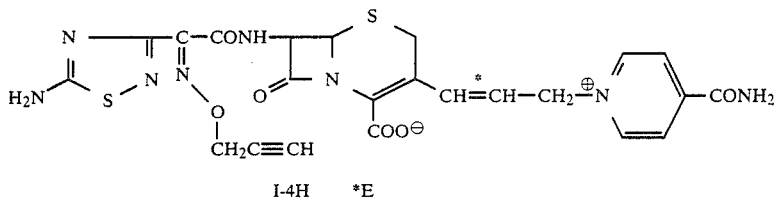

I-4H  *E

7-[2-(5-Amino-1,2,4-thiadiazol-3-yl)-2-propargyloxyiminoacetamido]-3-[3-(4-carbamoylpyridinio)-1-propenyl]-3-cephem-4-carboxylate (I-4H) (E isomer)

To a solution of 86 mg (0.19 mmole) of 7-amino-3-[3-(4-carbamoylpyridinio)-1-(E)-propenyl]-3-cephem-4-carboxylate hydrochloride (XXII-H) in 2 ml of 50% aqueous acetone was added 63 mg of 2-propargyloxyimino-2-(5-amino-1,2,4-thiadiazol-3-yl)acetyl chloride hydrochloride (from Preparation No. 26). The suspension was maintained at pH 6.5–7.0 with 2N Na$_2$CO$_3$ and then stirred at room temperature for 1 hour. The reaction mixture was acidified to pH 2 with 1N HCl and concentrated in vacuo. The residue was diluted with 30 ml of water, neutralized with NaHCO$_3$ and filtered. The filtrate was transferred on the top of a column which was packed with reverse phase carrier (30 ml) taken from a PrepPAK-500/C$_{18}$ cartridge (Waters). The column was eluted with water, 5% CH$_3$OH, 10% CH$_3$OH and 20% CH$_3$OH, successively. Fractions containing the product were combined and lyophilized to afford 13 mg (12%) of the title product I-4H. Estimated purity 70%. Mp. 160° C.

IR: $\nu_{max}$ (KBr) in cm$^{-1}$ 3400, 2120, 1765, 1680, 1610.

UV: $\lambda_{max}$ (Phosphate buffer, pH 7) in nm ($\epsilon$) 229 (24000), 288 (21200).

NMR: δ (D$_2$O) in ppm 3.78 (2H, s, 2-H), 5.15 (2H, d, J=1 Hz, —CH$_2$—C≡CH), 5.40 (1H, d, J=5 Hz, 6-H), 5.50 (2H, m, $\overline{\text{CH}}$-N$^+$), 5.98 (1H, d, J=5 Hz, 7-H), 6.20 (1H, m, 3-CH=CH), 7.05 (1H, d, J=17 Hz, 3-C$\underline{\text{H}}$), 8.50 (2H, d, J=7 Hz, $\overline{\text{Py}}$-H), 9.16 (2H, d, J=7 Hz, $\overline{\text{Py}}$-H).

EXAMPLE 27

7-[2-(5-Amino-1,2,4-thiadiazol-3-yl)-2-cyclopentyloxyiminoacetamido]-3-[3-(4-carbamoylpyridinio)-1-propenyl]-3-cephem-4-carboxylate (I-5H) (E isomer)

To a stirred solution of 139 mg (0.31 mmole) of 7-amino-3-[3-(4-carbamoylpyridinio)-1-propenyl]-3-cephem-4-carboxylate hydrochloride in 3.5 ml of 50% aqueous acetone in an ice-cooling bath was added portionwise 120 mg (0.44 mmole) of 2-(5-amino-1,2,4-thiadiazol-3-yl)-2-cyclopentyloxyiminoacetyl chloride hydrochloride (from Preparation No. 27). The mixture was adjusted to pH 6.5–7.0 with 2N Na$_2$CO$_3$ (0.9 ml) and stirred for 1 hour at 10° C. The reaction mixture was acidified to pH 2 with 1N HCl and evaporated under reduced pressure. The residue was chromatographed on a column of HP-20 resin (20 ml) and was eluted with 300 ml of water and 30% CH$_3$OH-H$_2$O, successively. Fractions containing the product were combined and concentrated in vacuo. The residue was treated with 60 ml of acetone to give 111 mg (83%) of the title compound I-5H. Mp. 160° C. (dec.). Estimated purity 70%.

IR: $\nu_{max}$ (KBr) cm$^{-1}$ 3400, 1770, 1680, 1605, 1530.

UV: $\lambda_{max}$ (Phosphate buffer, pH 7) in nm ($\epsilon$) 224 (23300), 286 (24600).

NMR: δ (DMSO-d$_6$) in ppm 1.70 (8H, br.s,

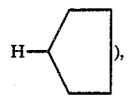

), 4.68 (1H, br.s,

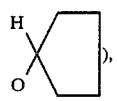

), 5.05 (1H, d, J=5 Hz, 6-H), 5.30 (2H, m, CH$_2$N$^+$), 5.67 (1H, d-d, J=5 Hz & 7 Hz, 7-H), 6.20 (1H, m, 3-CH=CH), 7.08 (1H, d, J=17 Hz, 3-CH), 8.34 (2H, d, J=7 Hz, $\overline{\text{Py}}$-H), 9.11 (2H, d, J=7 Hz, $\overline{\text{Py}}$-H), 9.38 (1H, d, J=7 Hz, 7-NH).

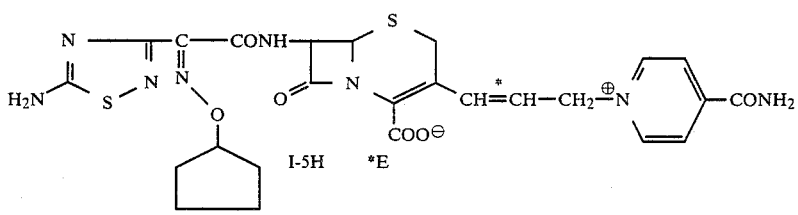

I-5H  *E

EXAMPLE 28

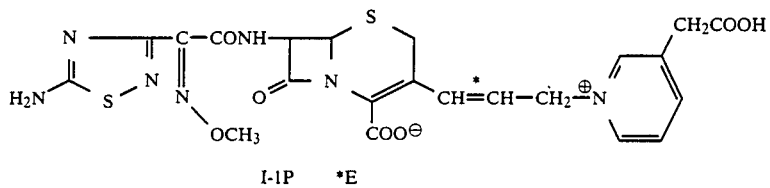

I-1P  *E

7-[2-(5-Amino-1,2,4-thiadiazol-3-yl)-2-methoxyiminoacetamido]-3-[3-(3-carboxymethylpyridinio)-1-propenyl]-3-cephem-4-carboxylate (I-1P) (E isomer)

A. Diphenylmethyl 7-[2-(5-Amino-1,2,4-thiadiazol-3-yl)-2-methoxyiminoacetamido]-3-[3-(3-carboxymethylpyridinio)-1-propenyl]-3-cephem-4-carboxylate (XII-1P, iodide, E isomer)

To a suspension of 3-carboxymethylpyridine hydrochloride (0.89 g, 5 mmoles) in 10 ml of $CH_2Cl_2$ was added N,O-bis(trimethylsilyl)acetamide (4.97 ml, 18 mmoles), and the mixture was stirred at room temperature until a clear solution was obtained. To the solution was added IX-1 (1.79 g, 2.5 mmoles), and the mixture was allowed to stand at room temperature. After 3 hours, 3 ml of $CH_3OH$ was added to the cooled mixture and the solution was evaporated in vacuo to give an oil which was triturated with ethyl acetate to afford 2.28 g of the title compound XII-1P as a tan powder. Mp. 161° C. (dec.).

IR: $\nu_{max}$ (KBr) in cm$^{-1}$ 1780, 1720, 1675, 1630, 1530, 1385, 1225, 1045, 755, 700.

UV: $\lambda_{max}$ ($C_2H_5OH$) in nm ($E_{1\ cm}^{1\%}$) 295 (188).

NMR: δ (DMSO+$D_2O$) in ppm 3.70 (2H, br.s, 2-H), 3.90 (5H, s, $OCH_3$ & Py-$CH_2$CO), 5.25 (3H, m, —$CH_2N^+$ & 6-H), 5.92 (1H, d, J=4.5 Hz, 7-H), 6.35 (1H, m, 3-CH=CH—), 6.90 (1H, d, J=16 Hz, 3-CH), 6.92 (1H, s, $CHPh_2$), 7.35 (10H, m, Ph-H), 8.8–9.0 (4H, m, Py-H).

B. 7-[2-(5-Amino-1,2,4-thiadiazol-3-yl)-2-methoxyiminoacetamido]-3-[3-(3-carboxymethylpyridinio)-1-propenyl]-3-cephem-4-carboxylate (I-1P) (E isomer)

A mixture of XII-1P (iodide) (2.28 g) and sodium bisulfite (1.1 g) in 85% HCOOH (10 ml) was stirred at room temperature for 2 hours. The reaction mixture was concentrated to ca. 5 ml under reduced pressure. The oily residue was triturated with acetone (100 ml) to give 1.22 g of the crude product, which was purified by column chromatography (HP-20, 420 ml) to afford 533 mg of the title compound I-1P (38%, from IX-1) as pale yellow amorphous powder. Mp. 165° C. (dec.).

IR: $\nu_{max}$ (KBr) in cm$^{-1}$ 1770, 1670, 1600, 1530, 1385, 1140, 1040.

UV: $\lambda_{max}$ (Phosphate buffer, pH 6.2) in nm ($E_{1\ cm}^{1\%}$) 234 (374), 277sh (390), 290 (402).

NMR: δ ($D_2O$+NaHCO$_3$) in ppm 3.78 (2H, s, 2-H), 3.92 (2H, s, Py-$CH_2$CO), 4.22 (3H, s, $OCH_3$), 5.40 (1H, d, J=4 Hz, 6-H), 5.44 (2H, d, J=6.5 Hz, —$CH_2$—N$^+$), 5.97 (1H, d, J=4 Hz, 7-H), 6.20 (1H, d-t, J=16 & 6.5 Hz, 3-CH=CH), 7.08 (1H, d, J=16 Hz, 3-CH), 8.11 (1H, d-d, J=8 & 7 Hz, Py-H$_5$), 8.53 (1H, d, J=8 Hz, Py-H$_4$), 8.82 (1H, d, J=7 Hz, Py-H$_6$), 8.86 (1H, s, Py-H$_2$).

EXAMPLE 29

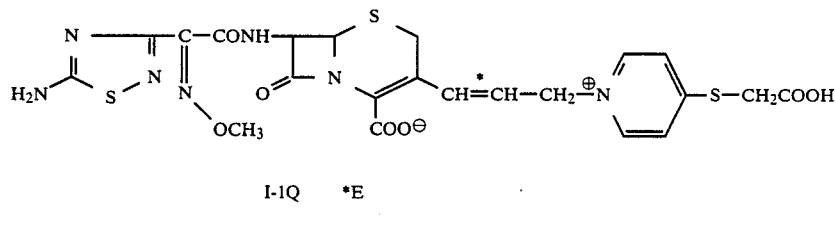

I-1Q  *E

7-[2-(5-Amino-1,2,4-thiadiazol-3-yl)-2-methoxyiminoacetamido]-3-[3-(4-carboxymethylthiopyridinio)-1-propenyl]-3-cephem-4-carboxylate (I-1Q) (E isomer)

A. Diphenylmethyl 7-[2-(5-Amino-1,2,4-thiadiazol-3-yl)-2-methoxyiminoacetamido]-3-[3-(4-carboxymethylthiopyridinio)-1-propenyl]-3-cephem-4-carboxylate (XII-1Q, iodide, E isomer)

To a suspension of 4-carboxymethylthiopyridine (0.88 g, 5 mmoles) in 10 ml of $CH_2Cl_2$ was added N,O-bis(trimethylsilyl)acetamide (5 ml, 18 mmoles), and the mixture was stirred at room temperature until a clear solution was obtained. To the solution was added IX-1 (E isomer 1.79 g, 2.5 mmoles), and the mixture was allowed to stand at room temperature. After 3 hours, 3 ml of $CH_3OH$ was added to the cold mixture and the solution was evaporated in vacuo to give oily residue which was triturated with ethyl acetate to give 2.43 g of the title compound XII-1Q (iodide) as a tan powder. Mp. 155° C. (dec.).

IR: $\nu_{max}$ (KBr) in cm$^{-1}$ 1780, 1720, 1670, 1625, 1525, 1385, 1225, 1115, 1040, 755, 700.

UV: $\lambda_{max}$ ($C_2H_5OH$) in nm ($E_{1\ cm}^{1\%}$) 312 (299).

NMR: δ (DMSO-$d_6$+$D_2O$) in ppm 3.70 (2H, br.s, 2-H), 3.93 (3H, s, $OCH_3$), 5.07 (2H, m, $CH_2$-N$^+$), 5.23 (1H, d, J=5 Hz, 6-H), 5.90 (1H, d, J=5 Hz, 7-H), 6.29 (1H, m, 3-CH=CH), 6.87 (1H, d, J=16 Hz, 3-CH), 6.91 (1H, s, $CHPh_2$), 7.35 (10H, m, Ph-H), 7.88 & 8.58 (each 2H, d, J=6 Hz, Py-H).

B. 7-[2-(5-Amino-1,2,4-thiadiazol-3-yl)-2-methoxyiminoacetamido]-3-[3-(4-carboxymethylthiopyridinio)-1-propenyl]-3-cephem-4-carboxylate (I-1Q) (E isomer)

A mixture of XII-1Q (iodide, 2.43 g) and sodium bisulfite (1.1 g) 85% HCOOH (10 ml) was stirred at room temperature for 2 hours. The reaction mixture was concentrated to ca. 5 ml under reduced pressure. The oily residue was triturated with acetone (100 ml), filtered and dried to give a crude product (1.39 g), which was purified by column chromatography (HP-20, 20 ml) to afford 577 mg of the title compound I-1Q (39% from IX-1) as a pale yellow amorphous powder. Mp. 188° C. (dec.).

IR: $\nu_{max}$ (KBr) in cm$^{-1}$ 1765, 1670, 1625, 1530, 1380, 1110, 1035.

UV: $\lambda_{max}$ (Phosphate buffer, pH 6.2) in nm (E$_{1\ cm}$1%) 234 (459), 310 (678).

NMR: δ (D$_2$O+NaHCO$_3$) in ppm 3.79 (2H, br.s, 2-H), 4.10 (2H, s, S-CH$_2$), 4.23 (3H, s, OCH$_3$), 5.25 (2H, d, J=6.5 Hz, CH$_2$-N$^+$), 5.39 (1H, d, J=4.0 Hz, 6-H), 5.97 (1H, d, J=4 Hz, 7-H), 6.18 (1H, d-t, J=15.5 Hz & 6.5 Hz, 3-CH=CH), 7.05 (1H, d, J=15.5 Hz, 3-CH), 7.84 & 8.55 (each 2H, d, J=7 Hz, Py-H).

EXAMPLE 30

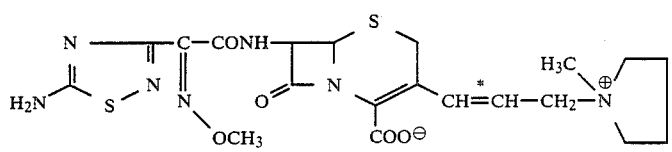

I-1A   *E/Z = 7/1

7-[2-(5-Amino-1,2,4-thiadiazol-3-yl)-2-methoxyiminoacetamido]-3-[3-(1-methylpyrrolidinio)-1-propenyl]-3-cephem-4-carboxylate sulfate (I-1A, sulfate)

A. Diphenylmethyl 7-[2-(5-Amino-1,2,4-thidiazol-3-yl)-2-methoxyiminoacetamido]-3-[3-(1-methylpyrrolidinio)-1-propenyl]-3-cephem-4-carboxylate (XII-1A, iodide)

To a cold solution of diphenylmethyl 7-[2-(5-amino-1,2,4-thiadiazol-3-yl)-2-methoxyiminoacetamido]-3-(3-iodopropenyl)-3-cephem-4-carboxylate (IX-1) (from Preparation No. 14) (21.5 g, 30 mmoles) in ethyl acetate (300 ml) was added dropwise a solution of 1-methylpyrrolidine (2.55 g, 30 mmoles) in ethyl acetate (30 ml) over a period of 1 hour at −5° to 0° C., with stirring. After stirring for an additional 10 minutes, the resulting precipitate was collected by filtration and washed with chloroform (200 ml) to give 23.0 g (95.8%) of the title compound (XII-1A, iodide), melting at >175° C. (dec.).

IR: $\nu_{max}$ (KBr) in cm$^{-1}$ 3300, 1780, 1730, 1685, 1615.

UV: $\lambda_{max}$ (C$_2$H$_5$OH) in nm (E$_{1\ cm}$1%) 218 (435), 295 (188).

B. Diphenylmethyl 7-[2-(5-Amino-1,2,4-thiadiazol-3-yl)-2-methoxyiminoacetamido]-3-[3-(1-methylpyrrolidinio)-1-propenyl]-3-cephem-4-carboxylate (XII-1A, chloride)

The compound (XII-1A, iodide) (23 g, 28.7 mmoles) was dissolved in a mixture of acetone and methanol (1:1, 230 ml) and applied on an Amberlite IRA-410 (chloride form, 230 ml) column which was pretreated with the same mixed solvent. The column was developed with the solvent and the fractions containing the desired compound were combined and concentrated to an oily residue, which was triturated with ethyl acetate (300 ml) to yield 17.9 g (87.7%) of the title compound (XII-1A, chloride), melting at 190° C. (dec.).

IR: $\nu_{max}$ (KBr) in cm$^{-1}$ 3380, 1780, 1680, 1620.

UV: $\lambda_{max}$ (C$_2$H$_5$OH) in nm (E$_{1\ cm}$1%) 220 (369), 290 (232).

C. 7-[2-(5-Amino-1,2,4-thiadiazol-3-yl)-2-methoxyiminoacetamido]-3-[3-(1-methylpyrrolidinio)-1-propenyl]-3-cephem-4-carboxylate sulfate (I-1A, sulfate)

A mixture of the compound (XII-1A, chloride) (17.8 g, 25 mmoles) in 85% formic acid (178 ml) was stirred at room temperature for 2 hours under a nitrogen atmosphere. The mixture was evaporated in vacuo and the oily residue was triturated with acetone to give 9.80 g of crude I-1A. Concentration of the filtrate and the acetone washings yielded additional 2.95 g of crude I-1A. Two crops of the crude material were combined and extracted with 2N HCl (1 L and 0.5 L). The combined extracts were adsorbed on a Diaion HP-20 resin (1.5 L column), which was eluted with water and 30% aqueous methanol. The desired fractions were collected and evaporated in vacuo to an oily residue, which was triturated with isopropanol (200 ml) and acetone (200 ml), successively, to yield 7.09 g of a light yellow powder. This material (6.80 g) was dissolved in water (20 ml) and then subjected to column chromatography over the packing of PrepPAK-500/C$_{18}$ cartridge (90 ml), using water and 10% aqueous methanol as an eluent. The eluate was collected in 20-ml fractions with monitoring by HPLC. [Column, Nucleocil SSC-ODS-262, 8×100 mm; Mobile phase, 0.01M phosphate buffer (pH 7.2)/CH$_3$OH=90:10; Detection, UV (254 nm)]. Fraction No. 4 through Fraction No. 10 were combined, evaporated under reduced pressure and lyophilized to give 2.28 g of a yellow powder (E/Z=7/1, 70% pure) [Crop 1]. Fraction No. 11 through Fraction No. 85 were worked up in the same manner as described above to give 3.27 g of yellow powder (E/Z=5/1, 70% pure) [Crop 2]. A portion of Crop 1 (1.0 g) was purified by rechromatography on the packing of PrepPAK-500/C$_{18}$ cartridge (90 ml). The column was eluted with water and 5% aqueous methanol, successively. The eluate containing the desired compound was concentrated and lyophilized to yield 638 mg (E/Z=7/1, 80% pure) of yellow powder. Another portion of Crop 1 (1.14 g) was worked up the same way to give 880 mg (E/Z=7/1, 80% pure) of yellow powder. The two purified samples were combined and a portion (1.45 g) dissolved in 1N sulfuric acid (5 ml). The solution was diluted with acetone (315 ml), with stirring. The creamy precipitate was collected by filtration to obtain 1.48 g of the title compound (I-1A, sulfate) (E/Z=7/1, 80% pure), melting at >185° C. (dec.).

IR: $\nu_{max}$ (KBr) in cm$^{-1}$ 3380, 3000, 1765, 1675, 1630, 1535, 1390, 1115.

UV: $\lambda_{max}$ (Phosphate buffer, pH 7) in nm ($\epsilon$) 236 (19900), 291.5 (22500).

NMR: δ (D$_2$O+NaHCO$_3$) in ppm 2.36 (4H, br.,

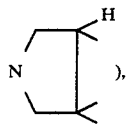

), 3.15 (3H, s,

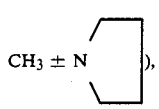

), 3.62 (5H, br., 2-H and

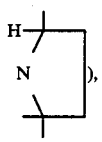

), 3.83 (1H, br., 2-H), 4.13 (2H, d, J=8 Hz, CH$_2$N+), 4.22 (3H, s, OCH$_3$), 5.39 (1H, d, J=4.5 Hz, 6-H), 5.96 (1H, d, J=4.5 Hz, 7-H), 6.00 (1H, m, 3-CH=CH), 6.67 (½H, d, J=10 Hz, 3-CH, cis), 7.04 (½H, d, J=16 Hz, 3-CH, trans).

EXAMPLE 31

7-[2-(5-Amino-1,2,4-thiadiazol-3-yl)-2-methoxyiminoacetamido]-3-[3-trimethylammonio-1-propenyl]-3-cephem-4-carboxylate (I-1D)

A. Diphenylmethyl 7-[2-(5-amino-1,2,4-thiadiazol-3-yl)-2-methoxyiminoacetamido]-3-(3-trimethylammonio-1-propenyl)-3-cephem-4-carboxylate (XII-1D, iodide)

To a solution of 13.0 g (19 mmoles) of diphenylmethyl 7-[2-(5-amino-1,2,4-thiadiazol-3-yl)-2-methoxyiminoacetamido]-3-(3-iodopropenyl)-3-cephem-4-carboxylate (IX-1, from Preparation No. 10) in 38 ml of dry ethyl acetate was added 1.75 ml (19.1 mmoles) of 1.1N trimethylamine in ethyl acetate at −5° C., and the mixture was stirred for 1 hour at −5° C. The resulting precipitate was filtered off, washed well with CHCl$_3$ and dried to give 12.5 g (88%) of the title compound (XII-1D) as the iodide.

IR: $\nu_{max}$ (KBr) in cm$^{-1}$ 3300, 1765, 1720, 1665.
UV: $\lambda_{max}$ (C$_2$H$_5$OH) in nm ($\epsilon$) 300 (18400).

B. Diphenylmethyl 7-[2-(5-Amino-1,2,4-thiadiazol-3-yl)-2-methoxyiminoacetamido]-3-(3-trimethylammonio-1-propenyl)-3-cephem-4-carboxylate (XII-1D, chloride)

The iodide (XII-1D, 12.5 g) was dissolved in 60 ml of CH$_3$OH-acetone (1:1) and passed through a column of ion-exchange resin [IRA-410 (Cl−), 125 ml]. The column was eluted with 300 ml of CH$_3$OH-acetone (1:1), and the eluate was evaporated in vacuo and triturated with 300 ml of isopropyl-ether to afford 10.4 g (91%) of the quaternary salt (XII-1D, chloride).

IR: $\nu_{max}$ (KBr) in cm$^{-1}$ 3300, 1765, 1710, 1665.
UV: $\lambda_{max}$ (C$_2$H$_5$OH) in nm ($\epsilon$) 298 (15100).

C. 7-[2-(5-Amino-1,2,4-thiadiazol-3-yl)-2-methoxyiminoacetamido]-3-[3-trimethylammonio-1-propenyl]-3-cephem-4-carboxylate (I-1D, sulfate, E isomer)

A solution of 10.4 g (16.0 mmoles) of XII-1D (chloride) in 20.8 ml of 85% formic acid was allowed to stand for 3 hours at room temperature and concentrated in vacuo. The residue was treated with 210 ml of isopropanol and the precipitate was filtered off. The solid (10.1 g) was triturated with 210 ml of water and neutralized with sodium bicarbonate. The suspension was filtered off and the filtrate was chromatographed on a column of HP-20 (300 ml) which was eluted with water (1000 ml), 10% CH$_3$OH (200 ml) and 30% CH$_3$OH (150 ml), successively. Fractions containing the desired product were combined and concentrated under reduced pressure. The residue was purified by reverse phase chromatography. The column was packed with a packing obtained from a PrepPAK-500/C$_{18}$ cartridge (Waters, 200 ml). Elution with water (600 ml) and 30% CH$_3$OH

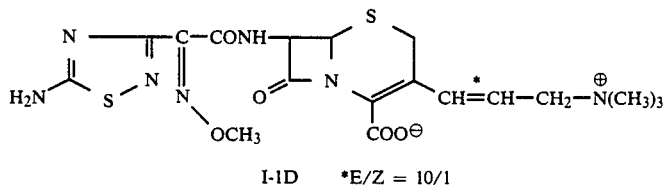

I-1D   *E/Z = 10/1

(200 ml), successively, followed by concentration of fractions containing the desired product gave 2.52 g (18%) of the title compound. A solution of the zwitterionic product (1.5 g) in 1N H$_2$SO$_4$ (5 ml) was added portionwise to 300 ml of acetone and the resulting precipitate was filtered and dried. Yield of I-1D sulfate was 1.42 g (80%). The ratio of E/Z was approximately 10/1 based on HPLC.

IR: $\nu_{max}$ (KBr) in cm$^{-1}$ 3380, 1765, 1665.
UV: $\lambda_{max}$ (Phosphate buffer, pH 7) in nm ($\epsilon$) 237 (19500), 293 (22400).

NMR: δ (D$_2$O) in ppm 3.25 (9H, s, N+—CH$_3$), 3.94 (2H, s, 2-H), 4.14 (2H, d, J=7 Hz, CH$_2$N+), 4.23 (3H, s, O—CH$_3$), 5.42 (1H, d, J=4.5 Hz, 6-H), 6.00 (1H, d, J=4.5 Hz, 7-H), 6.23 (1H, d-t, J=7 & 16 Hz, 3-CH=CH), 7.23 (1H, d, J=16 Hz, 3-CH).

EXAMPLE 32

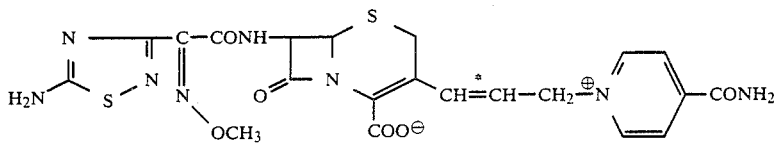

I-1H  *E

7-[2-(5-Amino-1,2,4-thiadiazol-3-yl)-2-methoxyiminoacetamido]-3-[3-(4-carbamoylpyridinio)-1-propenyl]-3-cephem-4-carboxylate (I-1H, E isomer)

To a mixture of 7-amino-3-[3-(4-carbamoylpyridinio)-1-(E)-propenyl]-3-cephem-4-carboxylic acid hydrochloride (XXII-H, 397 mg, 1 mmole) and NaHCO$_3$ (168 mg, 2 mmoles) in aqueous DMF (water, 3.5 ml and DMF, 7.5 ml) was added benzotriazol-1-yl-2-(5-amino-1,2,4-thiadiazol-3-yl)-2-methoxyiminoacetate (479 mg, 1.5 mmoles) (from Preparation No. 28). The mixture was stirred at room temperature for 3.5 hours. The reaction mixture was adjusted to pH 3-4 with 3N HCl and diluted with 200 ml of acetone to give a precipitate, which was collected by filtration. The crude product was dissolved in a small volume of aqueous THF and the solution was adjusted to pH 6.8 with NaHCO$_3$, treated with decolorizing carbon, concentrated to ca. 1 ml and seeded with a few pieces of crystalline I-1H. After stirring overnight, the crystalline precipitate was collected by filtration to afford the title compound I-1H (zwitterion form). Yield 83 mg (16%). Mp. >185° C. (dec.). Physico-chemical data of this product were identical to those of the compound in Example 10.

Preparation No. 1

Diphenylmethyl 7-[2-(5-Amino-1,2,4-thiadiazol-3-yl)-2-methoxyiminoacetamido]-3-chloromethyl-3-cephem-4-carboxylate (IV-1)

To a stirred suspension of 2-(5-amino-1,2,4-thiadiazol-3-yl)-2-methoxyiminoacetic acid (III-1), (2.1 g, 10 mmole) in dry CH$_2$Cl$_2$ (50 ml) was added PCl$_5$ (2.09 g, 10 mmole) at −30° C., and the mixture was stirred for 20 minutes at −15° to −20° C. To the above acid chloride solution was added a solution of diphenylmethyl 7-amino-3-chloromethyl-3-cephem-4-carboxylate hydrochloride (II) (4.5 g, 10 mmole) in CH$_2$Cl$_2$ (50 ml) containing N,O-bis-(trimethylsilyl)acetamide (10 g, 50 mmole) at −30° C. After stirring at −10° C. for 1 hour, the mixture was concentrated to remove the CH$_2$Cl$_2$ and diluted with ethyl acetate (200 ml). The mixture was washed with 10% aqueous NaHCO$_3$ (2×40 ml), H$_2$O (2×20 ml) and brine (10 ml), successively, and dried over MgSO$_4$. The solvent was evaporated in vacuo and the resulting oily residue (10 g) was dissolved in CHCl$_3$ (20 ml) and chromatographed on a silica gel (Wako gel C-200, 100 g containing 10 ml of 1/1.5M pH 7 phosphate buffer) using 1-3% CH$_3$OH—CHCl$_3$. Fractions containing the title compound were evaporated to give 5.7 g (95%) of IV-1 as a yellow amorphous powder. M.p. >140° C. (dec.).

IR: $\nu_{max}^{KBr}$ cm$^{-1}$ 3300, 1780, 1720, 1680, 1620.
UV: $\lambda_{max}^{EtOH}$ nm ($\epsilon$) 245 (1800), 280 (9900).
NMR: $\delta_{ppm}^{DMSO-d6}$ 3.53 (2H, ABq, 2-H), 3.94 (3H, s, OCH$_3$), 4.42 (2H, s, 3-CH$_2$), 5.22 (1H, d, J=4.5, 6-H), 5.92 (1H, d-d, J=4.5 & 6, 7-H), 6.93 (1H, s, CHPh$_2$), 7.36 (10H, m, Ph-H), 8.1 (2H, br-s, NH$_2$), 9.58 (1H, d, J=6, 7-NH).

Preparation No. 2

Diphenylmethyl 7-[2-(5-Amino-1,2,4-thiadiazol-3-yl)-2-methoxyiminoacetamido]-3-iodomethyl-3-cephem-4-carboxylate (V-1)

A mixture of IV-1 from Preparation No. 1 (5.7 g, 9.5 mmole) and NaI (4.3 g 29 mmole) in dry acetone (50 ml) was stirred for 5 minutes at room temperature. The mixture was concentrated under reduced pressure and the resulting oil was skaken with a mixture of ethyl acetate (100 ml) and H$_2$O (10 ml). The organic layer was separated and washed with 10% w/v sodium thiosulfate and brine, successively. After drying, the ethyl acetate was removed in vacuo to give 6.1 g (93%) of the title compound (V-1) as a yellow amorphous powder melting at >120° C. (dec.).

IR: $\nu_{max}^{KBr}$ cm$^{-1}$ 3300, 1780, 1725, 1680, 1620.
UV: $\lambda_{max}^{EtOH}$ nm ($\epsilon$) 245 (17000), 282 (12000).
NMR: $\delta_{ppm}^{DMSO-d6}$ 3.72 (2H, ABq, 2-H), 3.94 (3H, s, OCH$_3$), 4.23 (2H, s, 3-CH$_2$), 5.21 (1H, d, J=4.5, 6-H), 5.89 (1H, d-d, J=4.5 & 6, 7-H), 6.94 (1H, s, CHPh$_2$), 7.35 (10H, m, Ph-H), 8.12 (2H, br-s, NH$_2$), 9.65 (1H, d, J=6, 7-NH).

Preparation No. 3

Diphenylmethyl 7-[2-(5-Amino-1,2,4-thiadiazol-3-yl)-2-methoxyiminoacetamido]-3-triphenylphosphoniomethyl-3-cephem-4-carboxylate iodide (VI-1)

A mixture of V-1 from Preparation No. 2 (690 mg, 1 mmole) and triphenylphosphine (786 mg, 3 mmole) in ethyl acetate (20 ml) was stirred overnight at room temperature. The solid which separated was collected, washed with ethyl acetate (2×10 ml) and dried to give 950 mg (100%) of the phosphonium iodide VI-1. M.p. 186° C. (dec.).

IR: $\nu_{max}^{KBr}$ cm$^{-1}$ 3300, 1780, 1710, 1680, 1610.
UV: $\lambda_{max}^{EtOH}$ nm ($\epsilon$) 268 (15000), 275 (13000), 300 (7300).
NMR: $\delta_{ppm}^{DMSO-d6}$ 3.52 (2H, br-s, 2H), 3.94 (3H, s, OCH$_3$), 5.34 (1H, d, J=4.5, 6-H), 5.9 (1H, m, 7-H), 6.3 (1H, s), 7.3 (10H, m, Ph-H), 7.8 (15H, m, Ph-H).

Preparation No. 4

Diphenylmethyl 7-[2-(5-Amino-1,2,4-thiadiazol-3-yl)-2-methoxyiminoacetamido]-3-[(triphenylphosphoranylidene)methyl]-3-cephem-4-carboxylate (VII-1)

A mixture of VI-1 from Preparation No. 3 (952 mg, 1 mmole), Amberlite IRA-410 (OH$^-$ form, 500 mg) and N NaOH (4 ml) in CH$_2$Cl$_2$ (10 ml) was stirred for 1 hour at room temperature. The mixture was filtered and the separated organic layer was dried over MgSO$_4$ and concentrated under diminished pressure. The resulting oil was triturated with ethyl acetate and the resulting yellow precipitate was collected by filtration to give 740 mg (90%) of the title compound VII-1. M.p. >180° C. (dec.).

IR: $\nu_{max}^{KBr}$ cm$^{-1}$ 3400, 1750, 1630.

UV: $\lambda_{max}^{EtOH}$ nm ($\epsilon$) 268 (12000), 276 (10000), 384 (23000).

Preparation No. 5

Diphenylmethyl 7-[2-(5-Amino-1,2,4-thiadiazol-3-yl)-2-methoxyiminoacetamido]-3-(3-chloro-1-propen-1-yl)-3-cephem-4-carboxylate (VIII-1)

To a solution of VII-1 from Preparation No. 4 (6.9 g, 8.4 mmole) were added MgSO$_4$ (3 g) and 40% chloroacetaldehyde (810 mg, 8.4 mmole). The mixture was stirred for 1.5 hours at room temperature and then filtered. The filtrate was eluted on silica gel (Wakogel C-200, 100 g containing 10 ml of 1/1.5M phosphate buffer) column by using CHCl$_3$, and CHCl$_3$ containing CH$_3$OH. Fractions containing the desired product (0.5–1% CH$_3$OH-CHCl$_3$) were evaporated in vacuo to give 1.6 g (30%) of the title compound VIII-1 as a yellow amorphous powder, which was a mixture of the Z and E isomers with respect to the chloropropenyl moiety (Z/E=2/1, by nmr). M.p. >130° C. (dec.).

IR: $\nu_{max}^{KBr}$ cm$^{-1}$ 3300, 1780, 1725, 1680, 1620.

UV: $\lambda_{max}^{EtOH}$ nm ($\epsilon$) 240 (20000), 286 (12000).

NMR: $\delta_{ppm}^{DMSO-d6}+D^{2O}$ 3.56 & 3.8 (m, 2-H), 3.94 (3H, s, OCH$_3$), 4.16 (d, J=7.5, CH$_2$Cl), 5.26 (1H, d, J=4.5, 6-H), 5.87 (1H, d, J=4.5, 7-H), 6.28 (⅔H, d, J=11, 3-CH cis-H), 6.72 (⅓H, d, J=16, 3-CH trans-H), 6.81 (⅔H, s, CHPh$_2$), 6.92 (⅓H, s, CHPh$_2$), 7.4 (10H, m, Ph-H).

Preparation No. 6

Diphenylmethyl 7-Benzylideneamino-3-[(triphenylphosphoranylidene)methyl]-3-cephem-4-carboxylate (XVI)

To a solution of diphenylmethyl 7-benzylideneamino-3-[(triphenylphosphonio)methyl]-3-cephem-4-carboxylate iodide (XV) [prepared according to the procedure of Japan published patent application (Kokai) No. 56-86187 (7/31/81)] (60 g, 70 mmole) in CH$_2$Cl$_2$ (350 ml) were added N NaOH (140 ml) and Amberlite IRA-410 (OH$^-$ form, 35 g) at 5° C. The mixture was stirred for 1 hour at 5° C. and filtered. The organic layer was separated, dried over MgSO$_4$, concentrated to ca. 100 ml of volume and precipitated with ethyl acetate (500 ml). The resulting yellow solid was collected by filtration and dried in vacuo to afford 48 g (94%) of the title compound XVI, melting at 195°–8° C. (dec.).

IR: $\nu_{max}^{KBr}$ cm$^{-1}$ 1770, 1620.

Preparation No. 7

Diphenylmethyl 7-Benzylideneamino-3-(3-chloro-1-propen-1-yl)-3-cephem-4-carboxylate (XVII)

To a stirred solution of XVI from Preparation No. 6 (2.9 g, 4 mmole) in a mixture of CH$_2$Cl$_2$ (40 ml) and H$_2$O (10 ml), was added anhydrous chloroacetaldehyde (800 mg) at room temperature. To the mixture was added additional 800 mg of chloroacetaldehyde in three portions over a period of 1 hour, while the pH of the mixture was kept between 6 to 9 by addition of N NaOH. After 15 minutes, the aqueous layer was removed and the organic layer was dried over MgSO$_4$. Evaporation of the solvent gave a red oil which was dissolved in a mixture of ethyl acetate and isopropyl ether (½, 80 ml). The solution was washed with saturated aqueous NaHCO$_3$ (10 ml) and H$_2$O (10 ml), successively. After drying over MgSO$_4$, removal of the solvent afforded 3.3 g of yellow oil. A solution of the oil in CH$_2$Cl$_2$ (50 ml) was filtered with aid of silica gel (12 g, Wakogel C-200) containing 1/1.5M phosphate buffer (1.2 ml, pH 6.4) and the silica gel was washed with CH$_2$Cl$_2$ (50 ml). The filtrate and washing were combined and evaporated to dryness. The residue was triturated with n-hexane to give 1.7 g (80%) of the title compound (XVII) as a yellow powder. The nmr spectrum indicated that the chloropropenyl moiety had the Z configuration. M.p. >50° C. (dec.).

IR: $\nu_{max}^{KBr}$ cm$^{-1}$ 3400, 1775, 1720, 1630.

UV: $\lambda_{max}^{EtOH}$ nm ($\epsilon$) 253 (11000), 258 (11000), 265 (10000), 273 (8300), 281 (7000), 290 (6300).

NMR: $\delta_{ppm}^{DMSO-d6}$ 3.63 (2H, br-s, 2-H), 4.0 (2H, m, CH$_2$-Cl), 5.42 (2H, m, 6-H & 3-CH=CH), 5.72 (1H, d, J=4.5, 7-H), 6.27 (1H, d, J=11, 3-CH), 6.85 (1H, s, CHPh$_2$), 7.33 (10H, m, Ph-H).

Preparation of anhydrous chloroacetaldehyde

Anhydrous calcium chloride was added to a chilled solution of 50% aqueous chloroacetaldehyde (50 ml), with stirring, to separate it into two layers. The chloroacetaldehyde hydrate layer[1] (the upper layer) was separated with diluted with CHCl$_3$ (100 ml), mixed with MgSO$_4$ (20 g), heated to reflux for 5 minutes, and filtered. The solvent and water were removed azeotropically (b.p. 56°–64° C.)[2], and the residue was distilled to give anhydrous chloroacetaldehyde[3], b.p. 70°–82° C./760 mm.

IR: $\nu_{max}^{film}$ cm$^{-1}$ 1720.

(1) R. P. Kurkjy, E. V. Brown, J. Amer. Chem. Soc., 74; 5778 (1952).
(2) S. Trippett, D. M. Walker, J. Chem. Soc., 1961 1266.
(3) H. O. House, V. K. Jones, G. A. Frank, J. Org. Chem., 29, 3327 (1964).

IR: $\nu_{max}^{film}$ cm$^{-1}$ 1720.

Preparation No. 8

Diphenylmethyl 7-Amino-3-(3-chloro-1-propen-1-yl)-3-cephem-4-carboxylate (XVIII)

A solution of XVII from Preparation No. 7 (180 mg, 0.34 mmole) in ethyl acetate (10 ml) was added to a solution of Girard Reagent T [(carboxymethyl)trimethylammonium chloride hydrazide] (251 mg, 1.5 mmole) in CH$_3$OH (10 ml) containing acetic acid (0.25 ml), at 5° C. After stirring for 30 minutes at 5° C., the mixture was concentrated to remove the CH$_3$OH and then ethyl acetate (20 ml) was added. The ethyl acetate solution was washed with H$_2$O (2×5 ml), saturated aqueous NaHCO$_3$ (5 ml) and brine (5 ml), successively and dried over MgSO$_4$. Evaporation of the solvent gave 145 mg (97%) of the title compound XVIII (Z isomer) as a yellow powder. M.p. >100° C. (dec.).

IR: $\nu_{max}^{KBr}$ cm$^{-1}$ 3400, 1770, 1720.

UV: $\lambda_{max}^{EtOH}$ nm ($\epsilon$) 252 (3700), 258 (3800), 260 (4000), 274 (4000), 285 (4000).

Preparation No. 9

Diphenylmethyl 7-[2-(5-Amino-1,2,4-thiadiazol-3-yl)-2-methoxyiminoacetamido]-3-(3-chloro-1-propen-1-yl)-3-cephem-4-carboxylate (VIII-1)

A mixture of 2-(5-amino-1,2,4-thiadiazol-3-yl)-2-methoxyiminoacetic acid (III-1) (10.1 g, 50 mmole) and $PCl_5$ (10.4 g, 50 mmole) in dry $CH_2Cl_2$ (100 ml) was stirred at $-7°$ to $-15°$ C. for 2 hours. The clear solution was poured into n-hexane (500 ml) to give a precipitate. The organic layer was discarded by decantation and the remaining solid was triturated with n-hexane (100 ml). The yellow precipitate was collected by filtration and dried in vacuo to give 12.5 g (99%) of the acid chloride, melting at 80° C. (dec.).

IR: $\nu_{max}^{nujol}$ cm$^{-1}$ 1770.

The acid chloride (25 mg, 0.1 mmole) was added to a solution of XVIII (Z isomer) from Preparation No. 8 (44 mg, 0.1 mmole) in dry $CH_2Cl_2$ (5 ml) at room temperature, with stirring. After 30 minutes, the mixture was concentrated under reduced pressure and diluted with ethyl acetate (20 ml) and saturated aqueous $NaHCO_3$ (5 ml). The organic layer was washed with saturated aqueous $NaHCO_3$ (5 ml), brine (5 ml), 10% HCl (5 ml) and brine (5 ml). The solvent was dried over $MgSO_4$ and then evaporated to dryness to give the product as a yellow foam. The foam was purified by silica gel (Wakogel C-200, 1 g, containing 0.1 ml of 1/1.5M phosphate buffer pH 6.4) column chromatography by elution with $CH_2Cl_2$—$CH_3OH$ (100:1), to give 31 mg (50%) of the title compound VIII-1 (Z isomer) as a yellow powder. M.p. >150° C. (dec.).

IR: $\nu_{max}^{KBr}$ cm$^{-1}$ 3400, 1775, 1720, 1675, 1630.

UV: $\lambda_{max}^{EtOH}$ nm ($\epsilon$) 240 (17000), 280 (10000).

NMR: $\delta_{ppm}^{DMSO-d6}$ 3.6 (2H, m, 2-H), 3.92 (3H, s, O—CH$_3$), 4.0 (2H, m, CH$_2$Cl), 5.27 (2H, m, 6-H & CH=CH), 5.83 (1H, d-d, $\overline{J}$=4.5 & 10, 7-H), 6.25 (1H, d, J=11, 3-C$\underline{H}$), 6.83 (1H, s, C$\underline{H}$Ph$_2$), 7.33 (10H, m, Ph-H), 8.0 (2H, br-s, NH$_2$), 9.57 (1$\overline{H}$, d, J=10, 7-NH).

Preparation No. 10

Diphenylmethyl 7-[2-(5-Amino-1,2,4-thiadiazol-3-yl)-2-methoxyiminoacetamido]-3-(3-iodo-1-propen-1-yl)-3-cephem-4-carboxylate (IX-1)

A solution of VIII-1 from Preparation No. 5 (Z/E=2/1, 480 mg, 0.77 mmole) in dry acetone (10 ml) containing NaI (346 mg, 2.3 mmole) was stirred for 30 minutes at ambient temperature. The reaction mixture was evaporated under reduced pressure. The resulting oil was partitioned between ethyl acetate (50 ml) and water (10 ml). The upper layer was washed with 10% w/v aqueous sodium thiosulfate solution (10 ml) and brine (10 ml) successively, and dried over $MgSO_4$. Evaporation of the solvent gave 540 mg (98%) of the title compound IX-1 (Z/E=1/1) as a reddish amorphous solid, melting at >120° C. (dec.).

IR: $\nu_{max}^{KBr}$ cm$^{-1}$ 3300, 1780, 1720, 1680, 1620.

UV: $\lambda_{max}^{EtOH}$ nm ($\epsilon$) 240 (21000), 290 (12000).

NMR: $\delta_{ppm}^{DMSO+D2O}$ 3.67 (2H, m, 2-H), 5.29 (1H, d, J=4.5, 6-H), 5.95 (1H, d, J=4.5, 7-H), 6.27 ($\frac{1}{2}$H, d, J=11, 3-CH cis), 6.72 ($\frac{1}{2}$H, d, J=16, 3-CH trans), 6.87 & 6.96 (each $\frac{1}{2}$H, s, C$\underline{H}$Ph$_2$), 7.4 (10H, m, Ph-H).

Preparation No. 11

Diphenylmethyl 7-[2-(5-Amino-1,2,4-thiadiazol-3-yl)-2-methoxyiminoacetamido]-3-(3-iodo-1-propen-1-yl)-3-cephem-4-carboxylate (IX-1)

A mixture of VIII-1 (Z isomer) from Preparation No. 9 (5.6 g, 9 mmole) and NaI (4 g, 27 mmole) in dry acetone (100 ml) was stirred for 1.5 hours at room temperature. The mixture was evaporated and the resulting oil was diluted with ethyl acetate (90 ml). The ethyl acetate layer was washed with 10% w/v aqueous sodium thiosulfate solution (10 ml) and H$_2$O (10 ml). Removal of the dried (MgSO$_4$) solvent gave a yellow oil, which was solidified by trituration with isopropyl ether. Filtration of the precipitate gave 4.3 g (67%) of the title compound IX-1 as the E isomer. M.p. >165° C. (dec.).

IR: $\nu_{max}^{KBr}$ cm$^{-1}$ 3400, 1780, 1725, 1680, 1610.

UV: $\lambda_{max}^{EtOH}$ nm ($\epsilon$) 240 (18000), 297 (11000).

NMR: $\delta_{ppm}^{DMSO-d6}+D_2O$ 3.90 (3H, s, OCH$_3$), 5.25 (1H, m, 6-H), 5.95 (1H, m, 7-H), 6.72 (d, J=16, 3-CH trans), 6.96 (1H, s, C$\underline{H}$-Ph$_2$), 7.4 (10H, m, Ph-H).

Preparation No. 12

Benzhydryl 7-Amino-3-[3-chloro-1-propen-1-yl]-3-cephem-4-carboxylate (Z-isomer) (XVIII)

Compound XVIII is the common intermediate utilized in Reaction Schemes 1b and 1c.

A. Benzhydryl 7-Benzylideneamino-3-triphenylphosphoniomethyl-3-cephem-4-carboxylate chloride (XV)

To a suspension of benzhydryl 7-amino-3-chloromethyl-3-cephem-4-carboxylate hydrochloride (II hydrochloride) (200 g, 0.44 mole) in CH$_2$Cl$_2$ (940 ml) was added 1N NaOH (440 ml) at room temperature. The mixture was shaken for 10 minutes and the organic layer was separated. To the organic layer were added MgSO$_4$ (75 g) and benzaldehyde (51 g, 0.48 mole) and the mixture was allowed to stand for 3 hours. The reaction mixture was filtered and the insolubles were washed with CH$_2$Cl$_2$ (200 ml). To the combined filtrate and washings was added triphenylphosphine (126 g, 0.48 mole). The mixture was concentrated to about 400 ml and allowed to stand for 4 days. The resulting viscous oil was diluted with ethyl acetate (1 L) and triturated to separate the title compound XV a pale yellow crystalline powder which was collected by filtration and dried in vacuo. Yield 322 g (96%). M.p. 185°–190° C. (dec.).

IR: $\nu_{max}^{KBr}$ cm$^{-1}$ 1780, 1720, 1630.

UV: $\lambda_{max}^{CH2Cl2}$ nm ($\epsilon$) 260 (24100).

B. Benzhydryl 7-Benzylideneamino-3-[(triphenylphosphoranylidene)methyl]-3-cephem-4-carboxylate (XVI)

A mixture of XV (322 g, 0.42 mole) and 5N Na$_2$CO$_3$ (252 ml) in CH$_2$Cl$_2$ (1.6 L) was stirred vigorously for 15 minutes at room temperature. The organic layer was separated, dried over MgSO$_4$ and concentrated to about 500 ml of volume. The concentrate was added to acetone (1 L), with stirring, to give a light yellow crystalline powder which was collected by filtration to yield 237 g (78%) of XVI, melting at 195°–198° C. (dec.).

IR: $\nu_{max}^{KBr}$ cm$^{-1}$ 1770, 1620.

UV: $\lambda_{max}^{CH2Cl2}$ nm ($\epsilon$) 254 (23000), 389 (22000).

NMR: $\delta_{ppm}^{CDCl_3}$ 2.56 & 3.16 (2H, ABq), 5.00 (1H, d, J=4 Hz), 5.23 (1H, d, J=4 Hz), 5.47 (1H, d, J=22 Hz), 6.95 (1H, s), 7.2–7.8 (30H, m), 8.55 (1H, s).

C. Benzhydryl 7-Amino-3-[chloro-1-propen-1-yl]-3-cephem-4-carboxylate hydrochloride (Z isomer) (XVIII Hydrochloride)

To a refluxing solution of XVI (214 g, 0.294 mole) and N,O-bis-(trimethylsilyl)acetamide (40 ml, 0.15 mole) in dry $CH_2Cl_2$ (2.9 L) was added dropwise, with stirring, a 50% solution of chloroacetaldehyde (93 g, 0.59 mole) in $CHCl_3$ over a period of 15 minutes. After standing for 30 minutes, the mixture was concentrated to dryness. To the residual oil were added $CH_2Cl_2$ (1.5 L), Girard Reagent T (99 g, 0.59 mole) and 10% aqueous HCl (300 ml), and the mixture was stirred for 1 hour at room temperature. The organic layer was washed with water (200 ml) and a saturated NaCl solution (200 ml), dried over $MgSO_4$, treated with charcoal (5 g) and filtered. The filtrate was cooled to $-10°$ C. and treated with 1N HCl in $CH_3OH$ (300 ml). The mixture was stirred for 30 minutes at room temperature and concentrated to about 300 ml. The concentrate was diluted with ethyl acetate (400 ml) and seeded with a few crystals of XVIII hydrochloride. After 2 hours the separated crystals were collected by filtration, washed with ethyl acetate (200 ml) and dried in vacuo to give 74 g (53%) of the title compound XVIII as its hydrochloride, melting at $>185°$ C. (dec.). Pale yellow needles.

IR: $\nu_{max}^{KBr}$ cm$^{-1}$ 2830, 1780, 1720.

UV: $\lambda_{max}^{EtOH}$ nm ($\epsilon$) 286 (8800).

NMR: $\delta_{ppm}^{DMSO-d6}$ 3.73 (2H, br, s, 2-H), 3.97 (2H, m, C$\underline{H}_2$Cl), 5.22 (1H, d, J=4.5 Hz, 6-H), 5.37 (1H, d, J=4.5 Hz, 7-H), 5.77 (1H, m, 3-CH=C$\underline{H}$), 6.45 (1H, d, J=11 Hz, 3-C$\underline{H}$), 6.88 (1H, s, CHPh$_2$), 7.33 (10H, br, s, Ph-$\underline{H}$).

Anal. Calc'd for $C_{23}H_{21}N_2O_3SCl\cdot HCl$: C, 57.87; H, 4.65; N, 5.87; S, 6.72; Cl, 14.85. Found: C, 57.62; H, 4.53; N, 5.70; S, 6.64; Cl, 14.89.

Preparation No. 13

Benzhydryl 7-[2-(5-Amino-1,2,4-thiadiazol-3-yl)-2-methoxyiminoacetamido]-3-[3-chloro-1-propen-1-yl]-3-cephem-4-carboxylate (Z isomer) (VIII-1)

To a stirred solution of XVIII (Z isomer) (20 g, 42 mmole) in $CH_2Cl_2$ (420 ml) containing N,O-bis(trimethylsilyl)acetamide (34 ml, 125 mmole) was added 2-(5-amino-1,2,4-thiadiazol-3-yl)-2-methoxyiminoacetyl chloride hydrochloride (15.2 g, 59 mmole) in three portions over a period of 30 minutes at $-10°$ to $0°$ C. The mixture was stirred for 30 minutes at $0°$–$5°$ C. and concentrated under reduced pressure. The residual brown oil was dissolved in ethyl acetate (420 ml) and the solution was washed successively with saturated aqueous NaHCO$_3$ (3×15 ml), saturated aqueous NaCl (15 ml), 10% HCl (15 ml) and saturated aqueous NaCl (15 ml), and concentrated to about 50 ml of the volume. To the concentrate was added n-heptane (200 ml) to give 28.5 g (90% pure) of the title compound VIII-1 (Z-isomer) as a colorless powder. M.p. $>150°$ C. (dec.).

IR: $\nu_{max}^{KBr}$ cm$^{-1}$ 3400, 1780, 1720, 1680, 1620.

UV: $\lambda_{max}^{EtOH}$ nm ($\epsilon$) 240 (20000), 283 (12000).

NMR: $\delta_{ppm}^{acetone-d6}$ 3.6 (2H, m, 2-H), 3.95 (3H, s, OC$\underline{H}_3$), 4.0 (2H, m, C$\underline{H}_2$Cl), 5.32 (1H, d, J=4.5 Hz, 6-$\underline{H}$), 5.62 (1H, m, 3-CH=C$\underline{H}$), 6.03 (1H, d, J=4.5 Hz, 7-H), 6.32 (1H, d, J=11 Hz, 3-C$\underline{H}$), 6.87 (1H, s, C$\underline{H}$Ph$_2$), 7.33 (10H, br, s, Ph-H).

Preparation No. 14

Benzhydryl 7-[2-(5-Amino-1,2,4-thiadiazol-3-yl)-2-methoxyiminoacetamido]-3-[3-iodo-1-propen-1-yl]-3-cephem-4-carboxylate (E isomer) (IX-1)

A mixture of VIII-1 (Z isomer) (28.5 g, 90% pure) and sodium iodide (19 g) in dry acetone (420 ml) was stirred for 10 minutes at room temperature and allowed to stand at 5° C. for 2 hours. The mixture was concentrated under reduced pressure. To the residue were added ethyl acetate (420 ml) and 10% w/v aqueous sodium thiosulfate solution (30 ml), and the mixture was shaken. The organic layer was washed with water (30 ml), dried over $MgSO_4$ and evaporated to about 50 ml of volume. The concentrate was diluted with n-heptane (200 ml) to yield 30.6 g (95% pure) of the title compound IX-1 (E isomer) as a yellow powder, melting at $>120°$ C. (dec.).

IR: $\nu_{max}^{KBr}$ cm$^{-1}$ 3400, 1780, 1725, 1680, 1620.

UV: $\lambda_{max}^{EtOH}$ nm ($\epsilon$) 306 (15000).

NMR: $\delta_{ppm}^{acetone-d6}$ 3.71 (2H, m, 2-H), 3.97 (3H, s, OC$\underline{H}_3$), 4.0 (2H, d, J=8 Hz, C$\underline{H}_2$I), 5.26 (1H, d, J=4.5 Hz, 6-H), 6.03 (1H, d-d, J=4.5 & 8 Hz, changed to doublet J=4.5 Hz by $D_2O$, 7-H), 6.32 (1H, d-t, J=15 & 8 Hz, 3-CH=C$\underline{H}$), 6.79 (1H, d, J=15 Hz, 3-C$\underline{H}$), 6.98 (1H, s, C$\underline{H}$Ph$_2$), 7.35 (10H, m, Ph-H), 7.63 (2$\underline{H}$, br, s, disappeared by $D_2O$, N$\underline{H}_2$) 8.52 (1H, d, J=8 Hz, disappeared by $D_2O$, 7-N$\underline{H}$).

Preparation No. 15

Benzhydryl 7-[2-(5-Amino-1,2,4-thiadiazol-3-yl)-2-methoxyiminoacetamido]-3-[3-(4-carbamoyl-1-pyridinio)-1-propen-1-yl]-3-cephem-4-carboxylate Iodide (E isomer) (XII-1H)

To a suspension of IX-1 (E isomer) (30.5 g) and isonicotinamide (26 g, 212 mmole) in $CH_3CN$ (120 ml) was added $CH_3OH$ (100 ml) until the mixture became clear. The solution was stirred for 2 hours under nitrogen atmosphere at room temperature and concentrated to about 100 ml under reduced pressure. The residual semi-solid was triturated with isopropyl ether (200 ml). The solvent was removed by decantation and the residual yellow powder was washed with a mixture of isopropyl ether and $CH_3OH$ (3/1, 120 ml). The powder was collected by filtration and dried in vacuo to give 36 g (75% pure estimated by HPLC) of the title compound XII-1H (E isomer) as a light yellow powder melting at $>150°$ C. (dec.).

IR: $\nu_{max}^{KBr}$ cm$^{-1}$ 3300, 1780, 1720, 1680, 1620.

UV: $\lambda_{max}^{EtOH}$ nm (E$_1$ $_{cm}^{1\%H}$) 282 (170).

NMR: $\delta_{ppm}^{DMSO-d6}$ 3.72 (2H, m, 2-H), 3.90 (3H, s, OC$\underline{H}_3$), 5.25 (3H, m, 6-H & C$\underline{H}_2$N$^+$), 5.9 (1H, d-d, J=4.5 & 8 Hz, changed to a doublet J=4.5 Hz by $D_2O$ addition, 7-H), 6.35 (1H, m, 3-CH=C$\underline{H}$), 6.89 (1H, s, C$\underline{H}$Ph$_2$), 6.9 (1H, d, J=16 Hz, 3-C$\underline{H}$), 7.35 (10H, m, Ph-H), 8.06 (2H, br, s, disappeared by $D_2O$, N$\underline{H}_2$), 8.21 (2H, br, s, disappeared by $D_2O$ addition, N$\underline{H}_2$), 8.36 & 9.07 (each 2H, d, J=6 Hz, Py-$\underline{H}$), 9.57 (1H, d, J=8 Hz, disappeared by $D_2O$ addition, 7-N$\underline{H}$).

Preparation No. 16

Benzhydryl 7-Benzylideneamino-3-[3-chloro-1-propen-1-yl]-3-cephem-4-carboxylate (XVII) (Z isomer)

To an ice-cooled mixture of the crystalline 7-aminocephem intermediate XVIII (Z isomer) (13.4 g, 28 mmole) and benzaldehye (3.3 g, 31 mmole) in ethyl acetate (150 ml) was added dropwise 0.5N sodium hydroxide (56 ml, 28 mmole) over a period of 20 minutes, to maintain the temperature of the reaction mixture below 10° C. The mixture was stirred with cooling for another 15 minutes, and the organic layer was separated, washed with saturated aqueous sodium bicarbonate (100 ml×2) and dried over magnesium sulfate. To the dried solution was added a small amount of charcoal and the mixture was filtered. The filtrate was concentrated to dryness. The residual oil was dissolved in carbon tetrachloride (50 ml), and concentrated again. This procedure was repeated 3 times, and the mixture was monitored by reverse phase tlc to confirm that all of the starting 7-aminocephalosporin was converted to the Schiff's base. Removing the solvent in vacuo gave 16.45 g of the title compound XVII (Z isomer) as a pale yellow powder (estimated purity 85%; M.p. 74° C. (dec.), which was used for the next step without purification.

IR: $\nu_{max}^{KBr}$ cm$^{-1}$ 1780, 1725, 1635.
UV: $\lambda_{max}^{CH2Cl2}$ nm (E$_{1\,cm}^{1\%}$) 257 (400).
NMR: $\delta_{ppm}^{CDCl3}$ 6.18 (1H, d, J=11 Hz).

Preparation No. 17

Benzhydryl 7-Benzylideneamino-3-[3-(4-carbamoyl-1-pyridinio)-1-propen-1-yl]-3-cephem-4-carboxylate Iodide (XXI-H) (E isomer)

To a chilled mixture of the 3-chloropropenylcephem XVII (Z isomer) (16.4 g) in acetone (5 ml), was added dropwise a solution of sodium iodide (6.3 g, 42 mmole) in acetone (30 ml) over 10 minutes under nitrogen atmosphere, and the mixture was stirred at room temperature. The reaction was monitored by the ratio of uv absorption [E$_{1\,cm}^{1\%}$ (255 nm)/E$_{1\,cm}^{1\%}$ (320 nm)]. When the ratio reached below 1.30 (after 45 minutes), the mixture was diluted with carbon tetrachloride (400 ml), and allowed to stand at room temperature. When the ratio came to below 1.10 (after 3 hours), the mixture was concentrated to a half its volume. The concentrate was treated with a small amount of charcoal and diatomaceous earth, and filtered. The filter cake was washed with a 1:1 mixture (100 ml) of methylene chloride and carbon tetrachloride. To the combined solution of the filtrate and washings, was added a solution of isonicotinamide (3.5 g, 28.7 mmole) in dimethylformamide (20 ml) and the mixture was concentrated under reduced pressure. The concentration was allowed to stand at room temperature for 1.5 hours and washed with isopropyl ether (100 ml×3). The residual brown semi-solid was dissolved in methylene chloride (50 ml) and the solution was added dropwise, with stirring, to ethyl acetate (1.5 L). The resulting precipitate was collected by filtration and washed with ethyl acetate (200 ml). After drying over phosphorous pentoxide in vacuo, 17 g of the title compound XXI-H (E isomer) was obtained. Yellow amorphous powder. M.p. 150°–155° C. (dec.). Estimated purity 80% by nmr.

IR: $\nu_{max}^{KBr}$ cm$^{-1}$ 1775, 1725, 1690, 1635.
UV: $\lambda_{max}^{CH2Cl2}$ nm (E$_{1\,cm}^{1\%}$) 258 (335), 298 (255).
NMR: $\delta_{ppm}^{DMSO-d6}$ 3.4–3.8 (2H, br.), 5.35 (2H, br.), 5.41 (1H, d, J=4 Hz), 5.73 (1H, d, J=4 Hz), 6.93 (1H, s), 6.97 (1H, d, J=16 Hz), 7.3–7.5 (15H, br. s), 8.40 (2H, d, J=6.5 Hz), 9.15 (2H, d, J=6.5 Hz).

Preparation No. 18

7-Amino-3-[3-(4-carbamoyl-1-pyridinio)-1-propen-1-yl]-3-cephem-4-carboxylate (XXII-H) (E isomer)

To a suspension of the quaternized cephem XXI-H (17 g) in 85% formic acid (25 ml) was added dropwise concentrated hydrochloric acid (5 ml), and the mixture was stirred at room temperature for 1.5 hours and treated with a small amount of charcoal. The mixture was filtered and washed with 85% formic acid (5 ml). The filtrate was combined with the wash and poured into acetone (1 L), with stirring. The resulting precipitate was collected by filtration to give 9.52 g of yellow-colored crude product. To a suspension of the crude material (9.5 g) in water (50 ml) was added a small amount of charcoal, and the mixture was filtered. The filtrate was added dropwise, with stirring, to isopropyl alcohol (700 ml). The resulting precipitate was collected by filtration, washed with a small amount of methanol (30 ml), and dried to give 7.58 g of the title compound XXII-H (E isomer) as the hydrochloride. Light yellow powder. Estimated purity 85% by UV. M.p. 173°–188° C. (dec.).

IR: $\nu_{max}^{KBr}$ cm$^{-1}$ 1795, 1680, 1620, 1575, 1540.
UV: $\lambda_{max}^{Phosphate\,buffer\,(pH\,7)}$ nm (E$_{1\,cm}^{1\%}$) 294 (457).
NMR: $\delta_{ppm}^{D2O+DCl}$ 3.82 (2H, s), 5.17 (1H, d, J=5 Hz), 5.33 (2H, d, J=7 Hz), 5.43 (1H, d, J=5 Hz), 6.37 (1H, d-t, J=16 & 7 Hz), 7.23 (1H, d, J=16 Hz), 8.34 (2H, d, J=7 Hz), 9.00 (2H, d, J=7 Hz).

Preparation No. 19

2-(5-Amino-1,2,4-thiadiazol-3-yl)-2-methoxyiminoacetyl Chloride Hydrochloride (III-1 as its acid chloride hydrochloride)

A. 2-Cyano-2-methoxyiminoacetamide

To a stirred mixture of α-cyanoacetamide (252 g, 3 mole) and sodium nitrite (414 g, 6 mole) in water (600 ml) was added acetic acid (371 ml, 10 mole) at 5°–10° C. over 1.5 hours. The mixture was allowed to stir for another 1.5 hours and adjusted to pH 8.5 with 6N NaOH. To the mixture was added dimethyl sulfate (568 ml, 6 mole) at 15°–20° C. and the mixture was stirred at 45° C. for 1.5 hours. The reaction mixture was adjusted to pH 8.5 with 6N NaOH and allowed to stand at 5° C. overnight to separate the precipitate, which was collected by filtration, washed with cold water and air-dried to give 292 g (77%) of the title compound as brown needles melting at 170°–172° C.

IR: $\nu_{max}^{KBr}$ cm$^{-1}$ 3400, 3180, 1720(sh), 1715, 1690, 1615, 1570.
UV: $\lambda_{max}^{H2O}$ nm (ε) 238.5 (8290), 268 (sh, 3870).
NMR: $\delta_{ppm}^{DMSO-d6}$ 4.20 (3H, s, OCH$_3$), 7.85 (2H, br. NH$_2$).
Anal. Calc'd. for C$_4$H$_5$N$_3$O$_2$: C, 37.80; H, 3.97; N, 33.06. Found: C, 37.43; H, 3.75; N, 32.51.

B. 2-Methoxyiminopropanedinitrile

A stirred mixture of 2-cyano-2-methoxyiminoacetamide (88.9 g, 0.7 mole), sodium chloride (70 g) and phosporus oxychloride (97 ml, 1.05 mole) in dry 1,2-dichloroethane (350 ml) was refluxed for 16 hours. The insolubles were filtered off through a dicalite pad and washed with dichloroethane. The filtrate and the wash were combined, and poured into stirred ice-water (1.5 L) to decompose the excess of phosphorus oxychloride. The organic phase was washed with 10% NaHCO$_3$ (500 ml), water (500 ml×3) and a saturated NaCl solution (500 ml), and dried over MgSO$_4$. The filtrate was distilled under diminished pressure to give 61.5 g (81%) of the title compound boiling at 62° C./24 mm Hg. (Lit., b.p. 47°–48° C./12 mm Hg).

IR: $\nu_{max}^{Liquid\ Film}$ cm$^{-1}$ 3020, 2960, 2245, 2020, 1530, 1455, 1080.

NMR: $\delta_{ppm}^{CDCl_3}$ 4.35 (3H, s, OCH$_3$).

C. 2-Cyano-2-methoxyiminoacetamidinium Acetate

To a solution of ammonium chloride (28.4 g 0.53 mole) in 28% aqueous ammonia (355 ml) and ethanol (180 ml) was added dropwise a solution of 2-methoxyiminopropanedinitrile (58.0 g, 0.53 mole) in ethanol (120 ml) at −15° to −10° C. over a period of 30 minutes, with stirring. The mixture was stirred at −10° C. overnight and then at ambient temperature (20°–25° C.) for one day. The reaction mixture was partitioned between water (350 ml) and CH$_2$Cl$_2$ (350 ml), and the aqueous phase was saturated with sodium chloride, and extracted again with CH$_2$Cl$_2$ (300 ml). The organic extracts were combined, dried over MgSO$_4$ and evaporated in vacuo. A solution of the residue in ethyl acetate (1.6 L) was adjusted to pH 3–4 with acetic acid to precipitate the title compound as crystals, which were collected by filtration and washed with ethyl acetate. Yield 67.6 g (69%). M.p. 152°–4° C. (dec.). [Lit., m.p. 150°–155° C. (dec.)].

IR: $\nu_{max}^{KBr}$ cm$^{-1}$ 3160, 2900, 2360, 2235, 2000, 1665, 1555, 1495, 1415.

UV: $\lambda_{max}^{EtOH}$ nm ($\epsilon$) 243 (8500), 265 (sh, 5380), 305 (sh, 1400).

NMR: $\delta_{ppm}^{DMSO-d_6}$ 1.88 (3H, s, CH$_3$COOH), 4.15 (3H, s, OCH$_3$), 7.60 (4H, br.).

Anal. Calc'd for C$_4$H$_6$N$_4$O.CH$_3$COOH: C, 38.71; H, 5.41; N, 30.09. Found: C, 38.71; H, 5.59; N, 29.51.

D. 2-(5-Amino-1,2,4-thiadiazol-3-yl)-2-methoxyiminoacetonitrile

To a suspension of 2-cyano-2-methoxyiminoacetamidinium acetate (125 g, 0.672 mole) in CH$_3$OH (1.25 L) were added dropwise triethylamine (234 ml, 1.68 mole) at −10° C., and subsequently Br$_2$ (41.6 ml, 0.806 mole) over 20 minutes at −15° to −10° C., and the mixture was stirred for 20 minutes. To the mixture was added dropwise a solution of KSCN (78.3 g, 0.806 mole) in CH$_3$OH (550 ml) over 1 hour at −15° to −10° C. After stirring at 0°–5° C. for 1 hour, the mixture was poured into ice-water (12 L) to form a crystalline precipitate, which was collected by filtration, washed with water and air-dried to give 120 g (98%) of the title compound. M.p. 263°–5° C. (dec.). The m.p. of the compound prepared by us is higher by about 60° C. than that given in the literature* [m.p. 210°–15° C. (dec.)], but our spectral and microanalytical data are consistent for the structure.

IR: $\nu_{max}^{KBr}$ cm$^{-1}$ 3435, 3260, 3120, 2960, 2245, 2020, 1630, 1545, 1455, 1415.

UV: $\lambda_{max}^{EtOH}$ nm ($\epsilon$) 248 (13300), 310 (3470).

NMR: $\delta_{ppm}^{DMSO-d_6}$ 4.21 (3H, s, OCH$_3$), 8.30 (2H, br. NH$_2$).

Anal. Calc'd for C$_5$H$_5$N$_5$OS: C, 32.78; H, 2.75; N, 38.23; S, 17.50. Found: C, 32.76; H, 2.51; N, 38.02; S, 17.50.

E. 2-(5-Amino-1,2,4-thiadiazol-3-yl)-2-methoxyiminoacetic Acid (III-1)

A mixture of 2-(5-amino-1,2,4-thiadiazol-3-yl-2-methoxyiminoacetonitrile (18.3 g, 0.1 mole) in 4N NaOH (250 ml) was heated at 50°–55° C. with stirring for 3 hours. The reaction mixture was adjusted to pH 1 with H$_3$PO$_4$, and washed with ethyl acetate (100 ml), saturated with NaCl, and extracted three times with a mixture of ethyl acetate and tetrahydrofuran (3:1, 300 ml×2, and 200 ml×1). The extracts were combined, dried over MgSO$_4$ and concentrated under reduced pressure. The residue was triturated with isopropyl ether to afford pale yellow crystals of the title acid. Yield 16.8 g (83%). M.p. 184°–5° C. (dec.). [Lit.*, m.p. 180°–182° C. (dec.)].

*Japan Kokai No. 57-158769 published Sept. 30, 1982, to Fujisawa (Brit. appl., 3/6/81)

IR: $\nu_{max}^{KBr}$ cm$^{-1}$ 3460, 3260, 3140, 1725, 1620, 1605, 1545.

UV: $\lambda_{max}^{H_2O}$ nm ($\epsilon$) 234 (13200), 288 (sh, 3620).

F. 2-5-Amino-1,2,4-thiadiazol-3-yl)-2-methoxyiminoacetyl Chloride Hydrochloride To a suspension of 2-(5-amino-1,2,4-thiadiazol-3-yl)-2-methoxyiminoacetic acid (III-1) (40.4 g, 0.2 mole) in dry CH$_2$Cl$_2$ (400 ml) was added PCl$_5$ (41.6 g, 0.2 mole) in one portion at −50° C. The mixture was stirred for 4 hours at −20° to −5° C., and poured into a mixture of n-heptane and isopropyl ether (2:1, 2 L). The yellow precipitate was collected by filtration, washed with the same solvent mixture, and dried with KOH under reduced pressure to give 46.0 g (90%) of the title acid chloride.

IR: $\nu_{max}^{Nujol}$ cm$^{-1}$ 1775.

Preparation No. 20

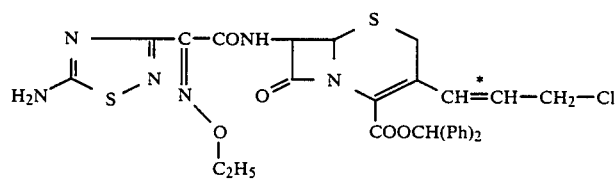

VIII-2    *Z

Diphenylmethyl 7-[2-(5-Amino-1,2,4-thiadiazol-3-yl)-2-(Z)-ethoxyiminoacetamido]-3-[3-chloro-1-propenyl]-3-cephem-4-carboxylate (VIII-2, Z isomer)

To a mixture of N,O-bis(trimethylsilyl)acetamide (2.3 ml, 9 mmoles) and crystalline diphenylmethyl 7-amino-3-[3-chloro-1-(Z)-propen-1-yl]-3-cephem-4-carboxylate hydrochloride (XVIII) (1.338 g, 2.8 mmoles) (from Preparation No. 12) in methylene chloride (10 ml) was added 2-(5-amino-1,2,4-thiadiazol-3-yl)-2-(Z)-ethoxyiminoacetyl chloride hydrochloride (800 mg, 2.95 mmoles) portionwise, with stirring, at $-10°$ C. and the mixture was allowed to stand at 0° C. for 2 hours. The mixture was diluted with ethyl acetate (200 ml), washed with water and evaporated under reduced pressure. Trituration of the residue with isopropyl ether afforded the title product VIII-2 as an amorphous powder. Yield 1.70 g (95%). Mp. >150° C. (dec.).

IR: $\nu_{max}$(KBr) in cm$^{-1}$ 3300, 1780, 1720, 1690, 1380, 1220.

UV: $\lambda_{max}$ (C$_2$H$_5$OH) in nm ($\epsilon$) 285 (11000).

NMR: $\delta$ (DMSO-d$_6$) in ppm 1.26 (3H, t, J=7 Hz, CH$_2$CH$_3$), 4.25 (2H, q, J=7 Hz, CH$_2$CH$_3$), 5.90 (1H, d-d, J=4 & 8 Hz, 7-H), 6.26 (1H, d, J=11 Hz, 3-CH), 6.85 (1H, s, CHPh$_2$), 9.53 (1H, d, J=8 Hz, 7-NH).

Preparation No. 21

Diphenylmethyl 7-Benzylideneamino-3-[(E)-3-(4-carbamoylpyridinio)-1-propenyl]-3-cephem-4-carboxylate (XXI-H iodide) (E isomer)

To a chilled solution of the 3-chloropropenylcephem (XVII, Z isomer, 42.8 g, 90 mmoles) (from Preparation No. 16) in dry DMF (80 ml), was added KI (20 g, 120 mmoles) in one portion, and the mixture was stirred at room temperature. The reaction was monitored by the ratio of UV absorption [E$_1$ $_{cm}$$^{1\%}$ (255 nm)/E$_1$ $_{cm}$$^{1\%}$ (320 nm)]. When the ratio became below 1.10 (after 45 minutes), the mixture was diluted with 800 ml of methylene chloride, treated with active carbon (4 g), and filtered. The filter cake was washed with 100 ml of CH$_2$Cl$_2$. To the combined filtrate and washings was added isonicotinamide (14.64 g), and the mixture was concentrated under reduced pressure. The concentrate was kept at room temperature for 1.5 hours and washed with a mixture of toluene and n-heptane (1:1, 600 ml). The residual brown semi-solid was dissolved in CH$_2$Cl$_2$ (100 ml) and the solution was added dropwise to ethyl acetate (3 L) with vigorous stirring. After drying over P$_2$O$_5$ in vacuo, 57.37 g (88%) of the quaternized title product XXI-H was obtained as the iodide. Yellow amorphous powder. Mp. 150°–155° C. (dec.). This product was identical to that obtained by iodination with NaI (Preparation No. 17).

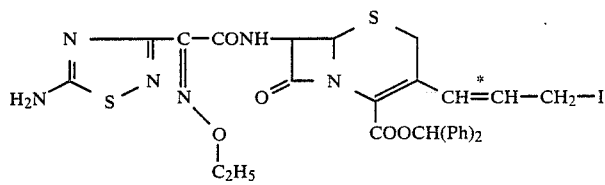

IX-2     *A mixture of E and Z isomers

Diphenylmethyl 7-[2-(5-Amino-1,2,4-thiadiazol-3-yl)-2-(Z)-ethoxyiminoacetamido]-3-[3-iodo-1-propenyl]-3-cephem-4-carboxylate (IX-2)

A mixture of VIII-2 (1.90 g, 3 mmoles) (from Preparation No. 20) and sodium iodide (1.4 g, 9 mmoles) in acetone (20 ml) was stirred for 10 minutes at room temperature and then allowed to stand at 5° C. for 3 hours. The mixture was evaporated under reduced pressure, diluted with ethyl acetate (100 ml), washed with 10% sodium thiosulfate and water, and evaporated under reduced pressure. Trituration of the residue with isopropyl ether gave 1.82 g (84%) of the title product IX-2 as a light brown amorphous powder.

IR: $\nu_{max}$(KBr) in cm$^{-1}$ 3290, 1770, 1720, 1670, 1530, 1370, 1220.

UV: $\lambda_{max}$ (C$_2$H$_5$OH) in nm (E$_1$ $_{cm}$$^{1\%}$) 304 (199).

Preparation No. 22

Preparation No. 23

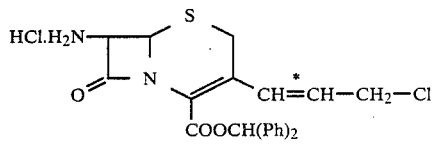

XVIII     *Z

Diphenylmethyl 7-Amino-3-(3-chloro-1-propenyl)-3-cephem-4-carboxylate hydrochloride (Z isomer) (XVIII, Hydrochloride)

A 25% solution of chloroacetaldehyde (69 g, 0.22 mmoles) in CHCl$_3$ was added to a solution of XVI (80 g, 0.11 mole) in CH$_2$Cl$_2$ (1.1 L) containing N,O-bis(trime-

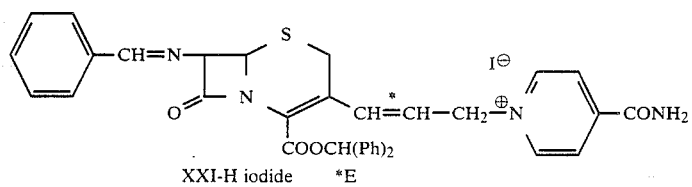

XXI-H iodide     *E thylsilyl)acetamide (16.2 ml, 0.06 mole) at −10° C. in one portion, and the mixture was allowed to stand overnight at 5° C. The mixture was concentrated to ca. 0.3 L, diluted with a mixed solvent of ethyl acetate and isopropyl ether (½, 0.6 L), treated with silica gel (Wakogel C-100, 60 g) and filtered through a dicalite pad. The filter cake was washed with the same solvent system (0.2 L). The combined filtrate and washing were concentrated to ca. 0.2 L, treated with Girard Reagent T (60 g, 0.26 mole) and 4N HCl (220 ml), and seeded with a few crystals of XVIII hydrochloride. After stirring for 3 hours, the resulting crystals were collected by filtration, washed with water (0.5 L) and ethyl acetate (0.5 L) and dried in vacuo to give 37 g (70%) of the title compound XVIII hydrochloride, melting at >185° C. (dec.). Pale yellow needles. This product was identical to that obtained in Preparation No. 12.

Preparation No. 24

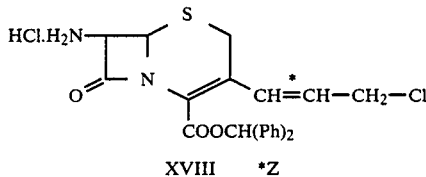

XVIII  *Z

Diphenylmethyl 7-Amino-3-(3-chloro-1-propenyl)-3-cephem-4-carboxylate hydrochloride (Z isomer) (XVIII, Hydrochloride)

To a solution of chloroacetaldehyde (25% solution in CHCl$_3$, 628 mg, 2 mmoles) in CH$_2$Cl$_2$ (10 ml) were added N,O-bis(trimethylsilyl)acetamide (0.135 ml, 0.5 mmole) and XVI (728 mg, 1 mmole), successively, at 5° C. The mixture was allowed to stand overnight at 5° C. The mixture was evaporated and diluted with a mixture of ethyl acetate and isopropyl ether (½, 10 ml). Insolubles were removed by filtration and the filtrate was concentrated to ca. 5 ml. The concentrate was treated with 4N HCl (2 ml), seeded with XVIII hydrochloride and stirred for 1 hour at room temperature. The crystals were collected by filtration, washed with ethyl acetate (10 ml) and water (10 ml) and dried in vacuo to give 384 mg (80%) of the title compound XVIII hydrochloride, melting at >185° C. (dec.). Pale yellow needles. This product was identical to that obtained by Preparation No. 12.

Preparation No. 25

2-(5-Amino-1,2,4-thiadiazol-3-yl)-2-(propen-3-yloxyimino)acetyl chloride hydrochloride (III-3 as its acid chloride hydrochloride A. Methyl 2-(5-t-butoxycarbonylamino-1,2,4-thiadiazol-3-yl)-2-(propen-3-yloxyimino)acetate A mixture of 685 mg (3.37 mmoles) of N-(propen-3-yloxy)phthalimide [prepared according to the procedure of E. Grochosaki & J. Jurczak, Synthesis 1976 682] and 175 mg (3.35 mmoles) of hydrazine hydrate in 5 ml of C$_2$H$_5$OH was stirred for 1 hour at room temperature. The resulting precipitate was filtered off and the filtrate and washings were combined. To the solution was added 967 mg (3.37 mmoles) of methyl 2-(5-t-butoxycarbonylamino-1,2,4-thiadiazol-3-yl)-2-oxoacetate, and the mixture was allowed to stand for 1 hour at room temperature and concentrated by a rotary evaporator. The residue was purified by silica gel chromatography. The column was eluted with n-hexane/ethyl acetate (4:1) and fractions containing the major product were combined and evaporated under reduced pressure. Yield 514 mg (46%). Mp. 83°–86° C.

IR: $\nu_{max}$ (KBr) in cm$^{-1}$ 3100, 1745, 1710, 1610.

UV: $\lambda_{max}$ (C$_2$H$_5$OH) in nm ($\epsilon$) 223 (9700), 242 (10000).

NMR: $\delta$ (CDCl$_3$) in ppm 1.55 (9H, s, BOC-H), 4.40 (2H, d, J=5 Hz, O—CH$_2$), 5.21 (2H, m, C$\underline{H}_2$=CH), 5.90 (1H, m, —C$\underline{H}$=CH$_2$), 9.50 (1H, br.s, NH).

B. 2-(5-t-Butoxycarbonylamino-1,2,4-thiadiazol-3-yl)-2-(propen-3-yloxyimino)acetic acid[1])

A solution of 770 mg (2.3 mmoles) of methyl 2-(5-t-butoxycarbonylamino-1,2,4-thiadiazol-3-yl)-2-(propen-3-yloxyimino)acetate and 3.5 ml of 2N NaOH solution (7.0 mmoles) in 15 ml of CH$_3$OH was refluxed for 30 minutes. The reaction mixture was concentrated in vacuo and diluted with 10 ml of ethyl acetate-H$_2$O (1:1). The water layer was separated, acidified to pH 2 with 6N HCl and extracted with ethyl acetate (10 ml×2). The ethyl acetate solution was dried over MgSO$_4$ and concentrated by a rotary evaporator to afford 596 mg (81%) of the title compound. Mp. 134°–135° C. (lit[1]): mp. 135°–136° C.

(1) I. Csendes, et al., J. Antibiotics, 36, 1020 (1983).

IR: $\nu_{max}$ (Nujol) in cm$^{-1}$ 3150, 1745, 1710, 1550.

UV: $\lambda_{max}$ (C$_2$H$_5$OH) in nm ($\epsilon$) 223 (11000), 242 (11300).

NMR: $\delta$ (DMSO-d$_6$) in ppm 1.55 (9H, s, BOC-H), 4.77 (2H, d, J=5 Hz, O—CH$_2$), 5.22 (2H, m, C$\underline{H}_2$=CH), 6.0 (1H, m, C$\underline{H}$=CH$_2$).

C. 2-(5-Amino-1,2,4-thiadiazol-3-yl)-2-(propen-3-yloxyimino)acetic acid (III-3)[1]

A solution of 570 mg (1.74 mmoles) of 2-(5-t-butoxycarbonylamino-1,2,4-thiadiazol-3-yl)-2-(propen-3-yloxyimino)acetic acid in 6 ml of trifluoroacetic acid was allowed to stand for 1 hour at ambient temperature. Evaporation followed by trituration with 30 ml of isopropyl ether gave 376 mg (95%) of the title compound. Mp. 109° C. (dec.).

(1) Japan Kokai No. 57-112396 (7/13/82, Fujisawa) Brit. appl. No. 7935538 (10/12/79).

IR: $\nu_{max}$ (Nujol) in cm$^{-1}$ 3180, 1710, 1545, 1460.

UV: $\lambda_{max}$ (C$_2$H$_5$OH) in nm ($\epsilon$) 245 (13500).

NMR: $\delta$ (DMSO-d$_6$) in ppm 4.77 (2H, d, J=5 Hz, O—CH$_2$), 5.20 (2H, m, C$\underline{H}$=CH), 6.0 (1H, m, C$\underline{H}$=CH$_2$).

D. 2-(5-Amino-1,2,4-thiadiazol-3-yl)-2-(propen-3-yloxyimino)acetyl chloride hydrochloride A solution of 350 mg (1.54 mmoles) of III-3 and 410 mg (1.97 mmoles) of phosphorous pentachloride in dichloromethane (5 ml) was stirred for 1 hour at 25° C. The reaction mixture was poured into 60 ml of n-hexane and the precipitate was filtered off. Yield 323 mg.

IR: $\nu_{max}$ (Nujol) in cm$^{-1}$ 1765.

Preparation No. 26

2-(5-Amino-1,2,4-thiadiazol-3-yl)-2-propargyloxyiminoacetyl chloride hydrochloride (III-4 as its acid chloride hydrochloride)

A. Methyl 2-(5-t-Butoxycarbonylamino-1,2,4-thiadiazol-3-yl)-2-propargyloxyiminoacetate A suspension of 870 mg (4.32 mmoles) of N-propargyloxyphthalimide[1] and 200 mg (4.0 mmoles) of hydrazine hydrate in 5 ml of ethanol was stirred at 25° C. for 1 hour and filtered. To the combined filtrate and washings was added 1.0 g (3.86 mmoles) of methyl 2-(5-t-butoxycarbonylamino-1,2,4-thiadiazol-3-yl)-2-oxoacetate[2]. The solution was allowed to stand for 1 hour and concentrated under reduced pressure. Purification by silica gel chromatography followed by evaporation afforded 319 mg (27%) of the title product. Mp. 72°–75° C.

(1) Commercially available, Aldrich.
(2) I. Csendes et al., J: Antibiotics 36, 1020 (1983).

IR: $\nu_{max}$ (KBr) in cm$^{-1}$ 3200, 2380, 1745, 1710, 1610.
UV: $\lambda_{max}$ (C$_2$H$_5$OH) in nm ($\epsilon$) 235 (12200).
NMR: $\delta$ (DMSO-d$_6$) in ppm 1.56 (9H, s, BOC-H), 3.55 (1H, t, J=2 Hz, C≡CH), 4.85 (2H, d, J=2 Hz, —CH$_2$—C≡CH), 8.9 (1H, br.s, NH).

B. 2-(5-t-Butoxycarbonylamino-1,2,4-thiadiazol-3-yl)-2-propargyloxyiminoacetic acid A solution of 490 mg (1.4 mmoles) of methyl 2-(5-t-butoxycarbonylamino-1,2,4-thiadiazol-3-yl)-2-proopargyloxyiminoacetate and 2.2 ml of 2N aqueous NaOH solution (4.4 mmoles) in 14 ml of CH$_3$OH was refluxed for 30 minutes. The reaction mixture was concentrated under reduced pressure and 10 ml of ethyl acetate-H$_2$O (1:1) was added to the solution. The separated water layer was acidified to pH 2 with 6N HCl and extracted with ethyl acetate (2×10 ml). Drying over MgSO$_4$ followed by evaporation of the organic layer gave 149 mg (89%) of the title product. Mp. 135° C. (dec.).

IR: $\nu_{max}$ (Nujol) in cm$^{-1}$ 3350, 1720, 1670, 1550.
UV: $\lambda_{max}$ (C$_2$H$_5$OH) in nm ($\epsilon$) 233 (11500).
NMR: $\delta$ (DMSO-d$_6$) in ppm 1.55 (9H, s, BOC-H), 3.55 (1H, t, J=2 Hz, C≡CH), 4.89 (2H, d, J=2 Hz, CH$_2$C≡CH), 9.0 (1H, s, NH).

C. 2-(5-Amino-1,2,4-thiadiazol-3-yl)-2-propargyloxyiminoacetic acid (III-4)[3]

A solution of 410 mg (1.26 mmoles) of 2-(5-t-butoxycarbonylamino-1,2,4-thiadiazol-3-yl)-2-propargyloxyiminoacetic acid in 5 ml of trifluoroacetic acid was allowed to stand for 1 hour at 25° C. Evaporation followed by trituration of the residue with 25 ml of isopropyl ether gave 204 mg (72%) of the title compound. Mp. 156°–158° C. (dec.).

(3) Japan Kokai No. 57-112396 (7/13/82, Fujisawa) Brit. appl. No. 7935538 (10/12/79).

IR: $\nu_{max}$ (Nujol) in cm$^{-1}$ 3300, 2480, 1730, 1610.
UV: $\lambda_{max}$ (C$_2$H$_5$OH) in nm ($\epsilon$) 234 (12000).
NMR: $\delta$ (DMSO-d$_6$) in ppm 3.52 (1H, t, J=2 Hz, C≡CH), 4.86 (2H, d, J=2 Hz, CH$_2$—C≡CH), 8.10 (2H, br.s, NH$_2$).

D. 2-(5-Amino-1,2,4-thiadiazol-3-yl)-2-propargyloxyiminoacetyl chloride hydrochloride A mixture of 175 mg (0.07 mmole) of III-4 and 182 mg (0.88 mmole) of phosphorous pentachloride in dichloromethane (2 ml) was stirred for 1 hour at −5° C. The reaction mixture was poured into 30 ml of n-hexane and the precipitate was filtered off. Yield 65 mg (34%).
IR: $\nu_{max}$ (Nujol) in cm$^{-1}$ 1770.

Preparation No. 27

2-(5-Amino-1,2,4-thiadiazol-3-yl)-2-cyclopentyloxyiminoacetyl chloride hydrochloride (III-5 as its acid chloride hydrochloride)

A. Methyl 2-(5-butoxycarbonylamino-1,2,4-thiadiazol-3-yl)-2-cyclopentyloxyiminoacetate A suspension of 860 mg (3.7 mmoles) of N-(cyclopentyloxy)phthalimide[1] and 185 mg (3.7 mmoles) of hydrazine hydrate in 5 ml of C$_2$H$_5$OH was stirred for 1 hour at ambient temperature and filtered. The filtrate and washings were combined and added to 1.06 g (3.7 mmoles) of methyl 2-(5-t-butoxycarbonylamino-1,2,4-thiadiazol-3-yl)-2-oxoacetate[2]. The solution was allowed to stand for 1 hour at room temperature and concentrated in vacuo. The residue was purified by silica gel column chromatography. Elution with n-hexane-ethyl acetate (4:1) followed by evaporation gave the title product. Yield 906 mg (81%). Mp. 115°–118° C.

(1) U.S. Pat. No. 3,971,778 (7/27/76; Glaxo), Brit. appl. No. 49255 (10/25/72).
(2) I. Csendes et al., J. Antibiotics 36, 1020 (1983).

IR: $\nu_{max}$ (KBr) in cm$^{-1}$ 3200, 1745, 1710, 1550.
UV: $\lambda_{max}$ (C$_2$H$_5$OH) in nm ($\epsilon$) 217 (1800), 252 (7600).
NMR: $\delta$ (CDCl$_3$) in ppm 1.51 (9H, s, BOC-H), 1.60 (8H, br.s,

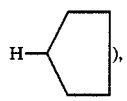

), 3.88 (3H, s, OCH$_3$), 4.90 (1H, br.s,

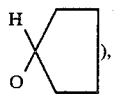

), 8.70 (1H, br.s, NH).

B. 2-(5-t-Butoxycarbonylamino-1,2,4-thiadiazol-3-yl)-2-cyclopentyloxyiminoacetic acid A solution of 500 mg (1.34 mmoles) of methyl 2-(5-t-butoxycarbonylamino-1,2,4-thiadiazol-3-yl)-2-cyclopentyloxyiminoacetate and 2N NaOH solution (2 ml, 4 mmoles) in 15 ml of CH$_3$OH was refluxed for 30 minutes. The reaction mixture was evaporated and 10 ml of ethyl acetate-H$_2$O (1:1) was added to the solution. The water layer was separated, acidified to pH 2 with 6N HCl and extracted with ethyl acetate (10 ml×2). The organic layer was washed with brine, dried over MgSO$_4$ and concentrated under reduced pressure to give 377 mg (78%) of the title compound. Mp. 185° C. (dec.).

IR: $\nu_{max}$ (KBr) in cm$^{-1}$ 3160, 1710, 1550.
UV: $\lambda_{max}$ (C$_2$H$_5$OH) in nm ($\epsilon$) 238 (13300).
NMR: $\delta$ (DMSO) in ppm 1.51 (9H, s, BOC-H), 1.70 (8H, br.s.,

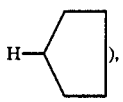), 4.82 (1H, m,

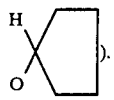).

C.
2-(5-Amino-1,2,4-thiadiazol-3-yl)-2-cyclopentyloxyiminoacetic acid (III-5, Z isomer)[3]

A solution of 348 mg (0.97 mmoles) of 2-(5-t-butoxycarbonylamino-1,2,4-thiadiazol-3-yl)-2-cyclopentyloxyiminoacetic acid in 2 ml of trifluoroacetic acid was allowed to stand for 1 hour at room temperature. The reaction mixture was concentrated under reduced pressure. The residue was triturated with 5 ml of isopropyl ether and 10 ml of hexane to give 215 mg (86%) of the title compound. Mp. 162°–165° C. (dec.) [lit[3]: mp. 160°–165° C. (dec.)].

[3] Japan Kokai No. 57-158769 (9/30/82, Fujisawa) Brit. appl. No. 8107134 (3/6/81).

IR: $\nu_{max}$ (Nujol) in cm$^{-1}$ 3290, 3200, 1710, 1615, 1600.
UV: $\lambda_{max}$ (C$_2$H$_5$OH) in nm ($\epsilon$) 238 (13300).
NMR: $\delta$ (DMSO-d$_6$) in ppm 1.17–2.10 (8H, m), 4.60–4.98 (1H, m), 8.22 (2H, s).

D.
2-(5-Amino-1,2,4-thiadiazol-3-yl)-2-cyclopentyloxyiminoacetyl chloride hydrochloride A solution of 190 mg (0.74 mmole) of III-5 and 219 mg (1.0 mmole) of phosphorous pentachloride in dichloromethane (5 ml) was stirred for 1 hour at room temperature. The reaction mixture was poured into 50 ml of n-hexane. The resulting precipitate was collected by filtration. Yield 122 mg (60%).

IR: $\nu_{max}$ (Nujol) in cm$^{-1}$ 1760.

Preparation No. 28

Benzotriazol-1-yl-2-(5-amino-1,2,4-thiadiazol-3-yl)-2-methoxyiminoacetate

A mixture of 1-hydroxybenzotriazole (2.7 g, 20 mmoles) and dicyclohexylcarbodiimide (4.12 g, 20 mmoles) in 65 ml of DMF was stirred at room temperature. After 15 minutes, III-1 (4.04 g, 20 mmoles) was added to the stirring mixture at 0° C., and stirring was continued for 3 hours. The reaction mixture was filtered to remove the insoluble urea, and the filter cake was washed with a small volume of DMF. The filtrate and washings were combined and poured into 800 ml of ice water. The precipitate was collected by filtration to give 5.24 g (82%) of the title compound as a light grey powder. Mp. 189°–192° C. (dec.).

IR: $\nu_{max}$ (KBr) in cm$^{-1}$ 1815, 1620, 1540, 1415, 1090, 1060, 1005, 945, 865, 740.
UV: $\lambda_{max}$ (C$_2$H$_5$OH) in nm (E$_{1\,cm}^{1\%}$) 246 (580), 283sh (228).

We claim:

1. The compound having the chemical name 7-[2-(5-amino-1,2,4-thiadiazol-3-yl)-2-methoxyiminoacetamido]-3-[3-(trimethylammonio)-1-propen-1-yl]-3-cephem-4-carboxylate, or a nontoxic pharmaceutically acceptable salt, solvate, hydrate or physiologically hydrolyzable ester thereof.

2. The compound of having the chemical name 7-[2-(5-amino-1,2,4-thiadiazol-3-yl)-2-methoxyiminoacetamido]-3-[3-(1-methylpyrrolidinio)-1-propen-1-yl]-3-cephem-4-carboxylate, or a nontoxic pharmaceutically acceptable salt, solvate, hydrate or physiologically hydrolyzable ester thereof.

3. The compound having the chemical name 7-[2-(5-amino-1,2,4-thiadiazol-3-yl)-2-methoxyiminoacetamido]-3-[3-pyridinio-1-propen-1-yl]-3-cephem-4-carboxylate, or a nontoxic pharmaceutically acceptable salt, solvate, hydrate or physiologically hydrolyzable ester thereof.

4. The compound having the chemical name 7-[2-(5-amino-1,2,4-thiadiazol-3-yl)-2-methoxyiminoacetamido]-3-[3-(3-aminopyridinio)-1-propen-1-yl]-3-cephem-4-carboxylate, or a nontoxic pharmaceutically acceptable salt, solvate, hydrate or physiologically hydrolyzable ester thereof.

5. The compound having the chemical name 7-[2-(5-amino-1,2,4-thiadiazol-3-yl)-2-methoxyiminoacetamido]-3-[3-(4-carbamoylpyridinio)-1-propen-1-yl]-3-cephem-4-carboxylate, or a nontoxic pharmaceutically acceptable salt, solvate, hydrate or physiologically hydrolyzable ester thereof.

6. The compound having the chemical name 7-[2-(5-amino-1,2,4-thiadiazol-3-yl)-2-methoxyiminoacetamido]-3-[3-(2-methylthiazolio)-1-propen-1-yl]-3-cephem-4-carboxylate, or a nontoxic pharmaceutically acceptable salt, solvate, hydrate or physiologically hydrolyzable ester thereof.

7. The compound having the chemical name 7-[2-(5-amino-1,2,4-thiadiazol-3-yl)-2-methoxyiminoacetamido]-3-[3-(2-amino-5-thiazolo[4,5-c]pyridinio)-1-propen-1-yl]-3-cephem-4-carboxylate, or a nontoxic pharmaceutically acceptable salt, solvate, hydrate or physiologically hydrolyzable ester thereof.

* * * * *